US008575195B2

(12) United States Patent
Halfon

(10) Patent No.: US 8,575,195 B2
(45) Date of Patent: Nov. 5, 2013

(54) TREATMENT OF HEPATITIS C VIRUS RELATED DISEASES USING HYDROXYCHLOROQUINE OR A COMBINATION OF HYDROXYCHLOROQUINE AND AN ANTI-VIRAL AGENT

(71) Applicant: Philippe Halfon, Marseilles (FR)

(72) Inventor: Philippe Halfon, Marseilles (FR)

(73) Assignees: Panmed Ltd., Beersel (BE); Genoscience Pharma SAS, Marseille (FR)

( * ) Notice: Subject to any disclaimer, the term of this patent is extended or adjusted under 35 U.S.C. 154(b) by 0 days.

(21) Appl. No.: 13/836,397

(22) Filed: Mar. 15, 2013

(65) Prior Publication Data

US 2013/0202556 A1 Aug. 8, 2013

Related U.S. Application Data

(63) Continuation of application No. 13/726,783, filed on Dec. 26, 2012, which is a continuation-in-part of application No. PCT/IB2011/052762, filed on Jun. 23, 2011.

(60) Provisional application No. 61/358,014, filed on Jun. 24, 2010.

(51) Int. Cl.
*A61K 31/47* (2006.01)

(52) U.S. Cl.
USPC ........................................................ 514/313

(58) Field of Classification Search
None
See application file for complete search history.

(56) References Cited

U.S. PATENT DOCUMENTS

| 5,624,938 A | 4/1997 | Pernis |
| 2004/0006103 A1 | 1/2004 | Valducci et al. |
| 2005/0009810 A1 | 1/2005 | Savarino |
| 2011/0003764 A1 | 1/2011 | Savarino |

FOREIGN PATENT DOCUMENTS

| WO | WO 2006/109196 | 10/2006 |
| WO | WO 2006/119061 | 11/2006 |
| WO | WO 2007/015855 | 2/2007 |
| WO | WO 2007/016441 | 2/2007 |
| WO | 2010/101649 A2 * | 9/2010 |
| WO | WO 2011/091757 | 8/2011 |
| WO | WO 2011/161644 | 12/2011 |
| WO | WO 2012/061248 | 5/2012 |
| WO | WO 2012/176149 | 12/2012 |

OTHER PUBLICATIONS

PCT International Search Report and Written Opinion, Re: PCT Application No. PCT/IB2011/052762, Dec. 7, 2011, European Patent Office, Rijswijk, The Netherlands.
Zuckerman et al., "Management of hepatitis C virus-related arthritis," *Biodrugs* (Sep. 2001) 15(9):573-84.
Kouromalis et al., "Hydroxychloroquine reduces liver related mortality in hepatitis C associated (HCV) compensated cirrhosis," *Gut* (Apr. 2002) 50 (Supp. 2): A114-A115 Abstract # 422, & Annual Meeting of the British Society of Gastroenterology, Birmingham, England, UK, Mar. 17-20, 2002.
Chandramohan et al., "Preliminary report of anti-hepatitis C virus activity of chloroquine and hydroxychloroquine in huh-5-2 cell line," *Indian Journal of Pharmaceutical Sciences* (Feb. 1, 2006) 68(4):538-40.
Mizui et al., "Inhibition of hepatitis C virus replication by chloroquine targeting virus-associated autophagy," *J. Gastroenterology.* (Sep. 17, 2009) 45(2): 195-203.
Ge et al., "Autophagy: a strategy for malignant gliomas' resistance to therapy," *Medical Hypotheses.* (Jul. 1, 2009) 73(1);45-47.
Livesey et al., "Autophagy inhibition in combination cancer treatment," Database Medline [Online], US Nat'l Library of Medicine (NLM), XP002664364, Database Accession No. NLM19943199, Dec. 2009, & *Curr. Opin. Inv. Drugs*, (Dec. 2009) 10(12): 1269-79.
Malik et al., "A pilot study of hydroxychloroquine in the treatment of chronic hepatitis C," *Gastroenterology*, (Apr. 1999) 116(4 p2): A1242-A1243, & Digestive Disease Week and the 100th Annual Meeting of the American Gastroenterological Association, Orlando, FL, USA, May 16-19, 1999.
PCT International Search Report and Written Opinion, Re: PCT Application No. PCT/IB2012/053143, Sep. 17, 2012.
International Preliminary Report on Patentability Dated Jan. 10, 2013 from the International Bureau of WIPO Re. PCT Application No. PCT/IB2011/052762.
Cholongitas et al., "Review Article: Novel Therapeutic Options for Chronic Hepatitis C," *Alimentary Pharmacology and Therapeutics*, XP002681940, 27(10): 866-884, May 2008.
Freiberg et al., "Combined chloroquine and Ribavirin treatment does not prevent death in a hamster model of Nipah and Hendra virus infection," *J. of Gen. Virology*, 91(3): 765-772 (Mar. 2010).
Halfon et al., "A new potent and selective HCV NS3 protease inhibitor with a high genetic barrier to resistance," *J. Hepatology*, XP002681937, (Mar. 2011), & 46th Annual Meeting of the European Association for the Study of the Liver (EASL), Berlin, Germany, Mar. 30-Apr. 1, 2011, 54 (Suppl. 1)L S478, Mar. 2011.
Halfon et al., GNS-227: A new potent and selective (2nd Gen) HCV NS3 protease inhibitor with a high genetic barrier to resistance, Retrieved from the Internet, XP002681938, 8 pages, Mar. 30, 2011.
Li et al., "Synthesis and SAR of acyclic HCV NS3 protease inhibitors with novel P4-Benzoxaborole moieties," *Bioorganic & Med. Chem. Lett.*, XP002681939, 21(7): 2048-54, Apr. 1, 2011.

(Continued)

*Primary Examiner* — James D Anderson
(74) *Attorney, Agent, or Firm* — Finnegan, Henderson, Farabow, Gerrett & Dunner LLP

(57) ABSTRACT

Methods of treating a hepatitis C virus (HCV) related disease, such as HCV infections in subjects non-responsive to anti-HCV therapy, are described herein, comprising administering to the subject a therapeutically effective amount of hydroxychloroquine. An antiviral agent may be co-administered with the hydroxychloroquine. Methods utilizing synergistic combinations of hydroxychloroquine and an antiviral agent are disclosed. Further disclosed are compositions comprising hydroxychloroquine and an antiviral agent, as well as hydroxychloroquine and uses thereof for the treatment of a hepatitis C virus (HCV) related disease.

12 Claims, 16 Drawing Sheets

(56) References Cited

OTHER PUBLICATIONS

Scola et al., "Discovery and SAR of tripeptide acylsulfonamides as potent inhibitors of HCV NS3 protease," Abstracts of Papers, American Chemical Society, XP008155035, 238th American Chemical Society National Meeting, Washington, DC, USA, Aug. 16-20, 2009, 238; MEDI-229, Aug. 2009.

Wang et al., "Synthesis and SAR of a series of potent and novel small molecule inhibitors of HCV NS3 protease: exploring modified P2 elements in the tripeptide acylsulfonamide series," Abstracts of Papers, American Chemical Society, XP008154980, 238th American Chemical Society National Meeting, Washington, DC, USA, Aug. 16-20, 2009, 238; MEDI-106, Aug. 2009.

* cited by examiner

TREATMENT OF HEPATITIS C VIRUS RELATED DISEASES USING HYDROXYCHLOROQUINE OR A COMBINATION OF HYDROXYCHLOROQUINE AND AN ANTI-VIRAL AGENT

RELATED APPLICATIONS

This application is a Continuation of U.S. patent application Ser. No. 13/726,783, filed Dec. 26, 2012, which is a Continuation-In-Part (CIP) of PCT Patent Application No. PCT/IB2011/052762 having an International filing date of Jun. 23, 2011, which claims the benefit of priority under 35 U.S.C. §119(e) of U.S. Provisional Patent Application No. 61/358,014 filed on Jun. 24, 2010. The contents of the above applications are all incorporated by reference as if fully set forth herein in their entirety.

FIELD AND BACKGROUND OF THE INVENTION

The present invention, in some embodiments thereof, relates to therapy and, more particularly, but not exclusively, to methods and compositions for the treatment of Hepatitis C Virus (HCV) related diseases such as chronic HCV infection.

HCV is a positive-stranded RNA virus which has been classified as a separate genus in the Flaviviridae family. All members of the Flaviviridae family have enveloped virions that contain a positive stranded RNA genome encoding all known virus-specific proteins via translation of a single, uninterrupted, open reading frame. The single strand HCV RNA genome is approximately 9500 nucleotides in length and has a single open reading frame (ORF) encoding a single large polyprotein of about 3,000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The NS3 protein also exhibits nucleoside triphosphatase and RNA helicase activities. NS5B is a RNA-dependent RNA polymerase that is involved in the replication of HCV.

Infection by hepatitis C virus (HCV) is a compelling human medical problem. HCV is recognized as the causative agent for most cases of non-A, non-B hepatitis, with an estimated human sero-prevalence of 3% globally. Nearly four million individuals may be infected in the United States alone. Upon first exposure to HCV only about 20% of infected individuals develop acute clinical hepatitis while others appear to resolve the infection spontaneously. In almost 70% of instances, however, the virus establishes a chronic infection that persists for decades. This usually results in recurrent and progressively worsening liver inflammation, which often leads to more severe disease states such as cirrhosis and hepatocellular carcinoma.

The combination of a pegylated interferon (e.g., peg-IFN alpha-2a/b) and twice-daily oral doses of ribavirin, an anti-viral agent, is the current standard of care for the treatment of chronic HCV infection. Patients who will ultimately achieve a sustained virologic response to peg-IFN and ribavirin therapy usually develop a rapid decline in HCV-RNA levels after initiation of therapy, with levels becoming undetectable within 4-24 weeks. Liver enzyme levels become normal, and histologic findings improve markedly. With the above-mentioned combination therapy, approximately 75% to 80% of patients with HCV genotype 2 or 3 infection and 40% to 50% of those with genotype 1 infection achieve a sustained virologic response (SVR) [Sherman K. E., Clinical Need and Therapeutic Targets for New HCV Agents, in The Future of HCV: Small molecules in Development for Chronic Hepatitis C, Clinical Care Options LLC, 2007].

However, success rate of this combined therapy is limited as its outcome is highly dependent on the infecting HCV genotype. This treatment is effective in fewer than 50% of patients infected with HCV genotype 1 or 4, the most represented genotypes in Europe and USA. In many cases, non-response is related to host or viral factors that impair activation of the host's innate, interferon-driven immune response.

Others may achieve viral reduction during therapy but cannot tolerate full therapeutic doses or an adequate duration of treatment because of cytopenia, fatigue, or other adverse effects of treatment. Indeed, dose modifications for these reasons are required in 35% to 42% of treated patients, and approximately one third of these patients eventually discontinue treatment altogether. These dose reductions, temporary interruptions, and aborted treatment courses reduce the chance of achieving SVR.

Finally, the combination of peg-IFN and ribavirin is contraindicated altogether in many patients who are in need of anti-HCV therapy. Contraindications for therapy include severe cytopenia, hepatic decompensation, renal insufficiency, poorly controlled autoimmune disease, severe cardiopulmonary disease, and active psychological problems. [Davis G. L., Investigational Small-Molecule Agents for the Treatment of Chronic Hepatitis C, in The Future of HCV: Small molecules in Development for Chronic Hepatitis C, Clinical Care Options LLC, 2007].

Briolant et al. [Antiviral Research 61 (2004) 111-117 teach that a combination of IFN-α2b and ribavirin has a subsynergistic anti-viral effect on CHIKV and SFV.

Alternative therapies for the treatment of HCV related diseases have been developed. U.S. Pat. No. 6,849,254 discloses a combination therapy including the administration of interferon alfa and ribavirin for a time sufficient to lower HCV-RNA, in association with an antioxidant for a time sufficient to improve ribavirin-related hemolysis.

U.S. Pat. No. 7,115,578 discloses a combination therapy comprising administering a therapeutically effective amount of ribavirin derivatives and a therapeutically effective amount of interferon-alfa. U.S. Pat. No. 7,410,979 discloses a synergistically effective combination therapy of dihaloacetamide compounds and interferon or ribavirin against HCV infection. U.S. Pat. No. 7,671,017 discloses the use of cyclosporine and pegylated interferon for treating HCV.

Chloroquine is a well known lysosomotropic agent, currently attracting many hopes in terms of antiviral therapy as well as in antitumoral effect because of its pH-dependent inhibiting action on the degradation of cargo delivered to the lysosome, thus effectively disabling this final step of the autophagy pathway.

Hydroxychloroquine (HCQ) is a chemical derivative of chloroquine (CQ) which features a hydroxyethyl group instead of an ethyl group.

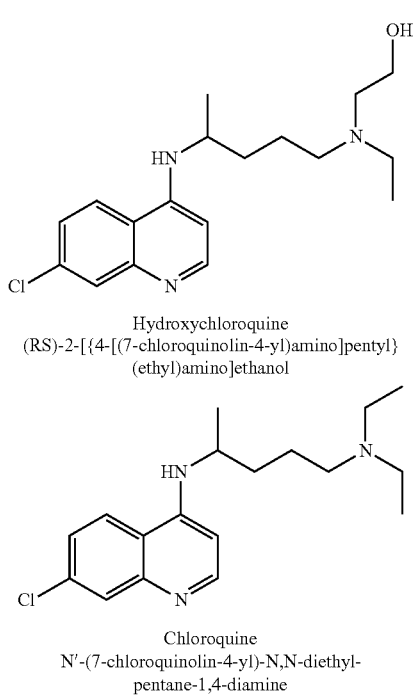

Hydroxychloroquine
(RS)-2-[{4-[(7-chloroquinolin-4-yl)amino]pentyl}(ethyl)amino]ethanol Chloroquine
N'-(7-chloroquinolin-4-yl)-N,N-diethyl-pentane-1,4-diamine HCQ has been classified as an effective anti-malarial medication, and has shown efficacy in treating systemic lupus erythematosus as well as rheumatoid arthritis and Sjögren's Syndrome. While HCQ has been known for some time to increase lysosomal pH in antigen presenting cells, its mechanism of action in inflammatory conditions has been only recently elucidated and involves blocking the activation of toll-like receptors on plasmacytoid dendritic cells (PDCs).

A direct comparison of the therapeutic effect of CQ and HCQ is quite difficult but it has been suggested that hydroxychloroquine was one-half to two-thirds as effective as chloroquine in treating rheumatologic diseases and one-half as toxic [Scherbel A L et al., Cleve Clin Q, 1958, 25:95]. Since chloroquine appears to be much more retinotoxic frequent use of hydroxychloroquine is increasing [Rynes R. I., British Journal of Rheumatology, 1997; 36:799-805].

Chandramohan M. et al. [Indian J Pharm Sci 2006; 68:538-40] have reported the screening of chloroquine and hydroxychloroquine for potential in vitro antiviral activity against HCV in Huh 5-2 cells, and showed that chloroquine was able to reduce the viral RNA to below 7% and promoted cell growth to more than 91% with respect to the untreated control at the concentration of 10.75 µM, and that hydroxychloroquine was able to reduce the viral RNA to below 7% and promoted cell growth to more than 81% with respect to the untreated control at the concentration of 6.6 µM. Chandramohan M. et al. neither demonstrate that HCQ may be used in combination with an antiviral agent to treat HCV related diseases, nor characterize the effect of such a combination (antagonist, additive, or synergistic).

Freiberg et al. [Journal of General Virology (2010), 91, 765-772] have evaluated the antiviral efficacy of chloroquine, individually and in combination with ribavirin, in the treatment of NiV and HeV infection in in vivo experiments, using a golden hamster model, and have reported that while both drugs exhibit a strong antiviral activity in inhibiting viral spread in vitro, they did not prove to be protective in the in vivo model. Ribavirin delayed death from viral disease in NiV-infected hamsters by approximately 5 days, but no significant effect in HeV-infected hamsters was observed. Chloroquine did not protect hamsters when administered either individually or in combination with ribavirin, the latter indicating the lack of a favorable drug-drug interaction.

Zuckerman et al. [BioDrugs 2001; 15(9), pp. 574-584] suggest that oral administration of drugs such as HCQ, corticosteroids and other anti-inflammatory agents can be combined with anti-viral therapy for controlling HCV-related arthritis.

Mizui et al. [J Gastroenterol. 2010 February; 45(2):195-203. Epub 2009 Sep. 17] have later reported that treatment of cells transfected with HCV replicon with chloroquine suppressed the replication of the HCV replicon in a dose-dependent manner. It was shown that a treatment with chloroquine, a known inhibitor of autophagy, and interferon-alfa enhanced the antiviral effect of the interferon, thereby preventing re-propagation of HCV replicon. Mizui et al. did not demonstrate any synergistic or additive effect of the combination of CQ/interferon alfa, and did not relate to HCQ as a putative drug for HCV combination therapy.

A recent approach of gene expression profiling of JFH1 HCV infected Huh7 cells showed that infection clearly modulates expression of host genes involved in several cellular processes such as ER stress response, apoptosis, p53 signaling, detoxification, intracellular lipid metabolism, protein synthesis and degradation, post translational processes or cytoskeleton organization.

The link between autophagy, a mechanism for cell survival in response to cellular stress role in cell death, and viral replication, including in cases of HCV infection, is currently being investigated.

Autophagy, a cellular pathway leading to components self-degradation, is known to be activated in response to stress, including ER stress initiated after viral infection. Although autophagy provides protection against various infections, and has been described as a component of the innate immune response, several bacteria and viruses, including HCV, have developed strategies to subvert autophagic processes to facilitate their own replication [Schmid & Munz, Immunity 2007, 27:11-21; Wileman, Science 2006, 312:875-878]. It was found that silencing autophagy-related genes significantly blunts the replication of HCV [Mizui et al., 2010 supra] and decreases the production of infectious HCV particles. It has been suggested that induction of autophagy by HCV impairs the innate immune response, and disruption of autophagy in HCV-infected hepatocytes activates the interferon signaling pathway and enhances the innate immune response [Shrivastava et al., Hepatology 2011, 53:406-414].

HCV infection, in vitro and in vivo, induces ER stress and triggers autophagy through the induction of unfolded protein response (UPR) including the downstream IRE1, ATF6, and EIF2AK3/PERK signaling pathways [Sir et al., Hepatology 2008, 48:1054-1061]. However, HCV-induced autophagic process was thought to be incomplete since it does not lead to protein degradation [Sir et al., Hepatology 2008, 48:1054-1061].

Ke P Y. et al. have reported that a completed autophagic process totally suppresses innate antiviral immunity, through a blockade of the endogenous IFN response, allowing HCV RNA replication.

Although the main autophagy proteins seem to be proviral factors required for the translation of incoming HCV RNA, and thereby for the initiation of HCV replication, it has been suggested that autophagy is not required once infection is established [see, for example, Dreux et al., PNAS 2009, 106:14046-14051].

However, neither the host molecular mechanisms involved in response to HCV infection, nor the molecular basis of the antiviral activity of CQ and its interplay with autophagy have been clearly elucidated heretofore.

Recently, it has been suggested that autophagy is involved also in cancer therapy, as being induced by chemotherapy such as DNA-damaging chemotherapy, radiation therapy, and molecularly targeted therapies, and that chloroquine derivatives such as HCQ may be used to prevent the chemotherapy-induced autophagy [Ravi K. Amaravadi, J Clin Invest. 2008; 118(12):3837-3840].

Additional background art includes Jackson et al. [PLoS Biol 2005, 3:e156], Wong et al. [J Virol 2008, 82:9143-9153], Khakpoor et al. [J Gen Virol 2009, 90:1093-1103]. Lee et al. [Virology 2008, 378:240-248], Prentice et al. [J Bio Chem 2004, 279:10136-10141], and Kroemer et al. [Nat Rev Mol Cell Biol 2008, 9:1004-1010].

SUMMARY OF THE INVENTION

According to an aspect of some embodiments of the invention, there is provided a method of treating an HCV infection, the method comprising:

(a) identifying an HCV-infected subject non-responsive to an anti-HCV therapy; and (b) administering to the HCV-infected subject a therapeutically effective amount of hydroxychloroquine or a pharmaceutically acceptable salt thereof, thereby treating the HCV infection.

According to an aspect of some embodiments of the present invention, there is provided a method of treating a hepatitis C virus (HCV) related disease in a subject in need thereof, the method comprising administering to the subject a therapeutically effective amount of hydroxychloroquine or a pharmaceutically acceptable salt thereof, the therapeutically effective amount being an amount sufficient to inhibit HCV-induced autophagy in the subject, thereby treating the HCV related disease.

According to an aspect of some embodiments of the present invention, there is provided hydroxychloroquine identified for use in the treatment of a hepatitis C virus (HCV) related disease in an amount sufficient to inhibit HCV-induced autophagy.

According to an aspect of some embodiments of the present invention, there is provided a use of a hydroxychloroquine in the manufacture of a medicament for use in the treatment of a hepatitis C virus (HCV) related disease, the treatment comprising administering to a subject in need thereof hydroxychloroquine in an amount sufficient to inhibit HCV-induced autophagy.

According to an aspect of some embodiments of the present invention, there is provided a method of treating an hepatitis C virus (HCV) related disease in a subject in need thereof, the method comprising co-administering to the subject a therapeutically effective amount of hydroxychloroquine or a pharmaceutically acceptable salt thereof and a therapeutically effective amount of an antiviral agent, wherein the anti-viral agent does not inhibit HCV-induced autophagy, thereby treating the HCV infection.

According to an aspect of some embodiments of the present invention, there is provided hydroxychloroquine for use in the treatment of a hepatitis C virus (HCV) related disease in combination with an antiviral agent that does not inhibit HCV-induced autophagy.

According to an aspect of some embodiments of the present invention, there is provided a use of hydroxychloroquine in the manufacture of a medicament for use in the treatment of a hepatitis C virus (HCV) related disease in combination with an anti-viral agent that does not inhibit HCV-induced autophagy.

According to an aspect of some embodiments of the present invention, there is provided a method of treating an HCV related disease caused by a hepatitis C virus (HCV) genotype resistant to an antiviral agent in a subject in need thereof, the method comprising co-administering to the subject a therapeutically effective amount of hydroxychloroquine or a pharmaceutically acceptable salt thereof and a therapeutically effective amount of the antiviral agent, thereby treating the HCV related disease.

According to an aspect of some embodiments of the present invention, there is provided hydroxychloroquine, for use in combination with an antiviral agent in the treatment of an HCV-related disease caused by a hepatitis C virus (HCV) genotype resistant to the antiviral agent.

According to an aspect of some embodiments of the present invention, there is provided a use of hydroxychloroquine in the manufacture of a medicament for use in combination with an antiviral agent in the treatment of an HCV-related disease caused by a hepatitis C virus (HCV) genotype resistant to the antiviral agent.

According to an aspect of some embodiments of the present invention, there is provided a method of treating a hepatitis C virus (HCV) related disease in a subject in need thereof, the method comprising co-administering to the subject a therapeutically effective amount of hydroxychloroquine or a pharmaceutically acceptable salt thereof in combination with a therapeutically effective amount of an antiviral agent, wherein the therapeutically effective amount of hydroxychloroquine and the therapeutically effective amount of the antiviral agent are selected such that hydroxychloroquine and the anti-viral agent act in synergy, thereby treating the HCV related disease.

According to an aspect of some embodiments of the present invention, there is provided a method of treating a hepatitis C virus (HCV) related disease in a subject in need thereof, the method comprising co-administering to the subject from 400 to 2000 mg per day of hydroxychloroquine or a pharmaceutically acceptable salt thereof in combination with from 50 to 250 μg per week of an interferon, wherein the hydroxychloroquine and the interferon act in synergy, thereby treating the HCV related disease.

According to an aspect of some embodiments of the present invention, there is provided a method of treating a hepatitis C virus (HCV) related disease in a subject in need thereof, the method comprising co-administering to the subject from 400 to 2000 mg per day of hydroxychloroquine or a pharmaceutically acceptable salt thereof in combination with a therapeutically effective amount of a viral protease inhibitor, wherein the hydroxychloroquine and the viral protease inhibitor act in synergy, thereby treating the HCV related disease.

According to an aspect of some embodiments of the present invention, there is provided a method of treating a hepatitis C virus (HCV) related disease in a subject in need thereof, the method comprising co-administering to the subject from 400 to 2000 mg per day of hydroxychloroquine or a pharmaceutically acceptable salt thereof in combination with a therapeutically effective amount of a viral polymerase inhibitor, wherein the hydroxychloroquine and the viral polymerase inhibitor act in synergy, thereby treating the HCV related disease.

According to an aspect of some embodiments of the present invention, there is provided hydroxychloroquine, identified for use in combination with an antiviral agent in the treatment of a hepatitis C virus (HCV) related disease, wherein the hydroxychloroquine and the antiviral agent act in synergy.

According to an aspect of some embodiments of the present invention, there is provided a use of hydroxychloroquine in the manufacture of a medicament identified for use in combination with an antiviral agent in the treatment of a hepatitis C virus (HCV) related disease, wherein the hydroxychloroquine and the antiviral agent act in synergy.

According to an aspect of some embodiments of the present invention, there is provided a pharmaceutical composition comprising hydroxychloroquine or a pharmaceutically acceptable salt thereof, an antiviral agent, and a pharmaceutically acceptable carrier.

According to an aspect of some embodiments of the present invention, there is provided a pharmaceutical composition unit dosage form comprising hydroxychloroquine or a pharmaceutically acceptable salt thereof, an antiviral agent, and a pharmaceutically acceptable carrier.

According to some embodiments of the invention, the antiviral agent is ribavirin.

According to some embodiments of the invention, the pharmaceutical composition or pharmaceutical composition unit dosage form is identified for use in the treatment of a hepatitis C virus (HCV) infection in an HCV-infected subject non-responsive to an anti-HCV therapy.

According to some embodiments of the invention, the abovementioned anti-HCV therapy comprises a treatment with PEGylated interferon α-2a or PEGylated interferon α-2b, in combination with ribavirin.

According to some embodiments of the invention, the HCV-infected subject is lacking a sustained virological response (SVR).

According to some embodiments of the invention, the pharmaceutically acceptable salt is hydroxychloroquine sulfate.

According to some embodiments of the invention, the unit dosage form comprises an amount of hydroxychloroquine sulfate in a range of from about 400 to about 600 mg.

According to some embodiments of the invention, the therapeutically effective amount of hydroxychloroquine or a pharmaceutically acceptable salt thereof is in a range of from about 400 to about 2000 mg per day.

According to some embodiments of the invention, the therapeutically effective amount of hydroxychloroquine or a pharmaceutically acceptable salt thereof is in a range of from about 500 to about 1000 mg per day.

According to some embodiments of the invention, the method further comprises administering to the HCV-infected subject a therapeutically effective amount of at least one antiviral agent.

According to some embodiments of the invention, the method further comprises administering to the HCV-infected subject a therapeutically effective amount of an interferon.

According to some embodiments of the invention, the interferon is PEGylated interferon α-2a.

According to some embodiments of the invention, the HCV-induced autophagy is characterized by an increase in a level of a protein selected from the group consisting of ULK1, AMBRA1, ATG2A, GABARAPL1, FOX03, SQSTM1, PIK3C3 and MAP1 LC3B.

According to some embodiments of the invention, the disease is caused by an anti-viral resistant HCV genotype.

According to some embodiments of the invention, the HCV is selected from the group consisting of genotype 1 HCV and genotype 4 HCV.

According to some embodiments of the invention, the HCV-infected subject is infected by genotype 1 HCV.

According to some embodiments of the invention, the HCV-infected subject is infected by genotype 1b HCV.

According to some embodiments of the invention, the method further comprises co-administering to the subject a therapeutically effective amount of an antiviral agent.

According to some embodiments of the invention, the antiviral agent is selected from the group consisting of ribavirin, viramidine, an interferon, a viral protease inhibitor, an NS4A inhibitor, an NS5A inhibitor, a viral polymerase inhibitor, a cyclophilin inhibitor, a helicase inhibitor, a glycosylation inhibitor, and an antiphospholipid antibody, and any combination thereof.

According to some embodiments of the invention, the antiviral agent is selected from the group consisting of ribavirin, a viral protease inhibitor, an NS4A inhibitor, an NS5A inhibitor, and a viral polymerase inhibitor, and any combination thereof.

According to some embodiments of the invention, the antiviral agent is selected from the group consisting of an interferon-α, ribavirin, viramidine, boceprevir, telaprevir, NM-107, valopicitabine, and alisporivir, and any combination thereof.

According to some embodiments of the invention, the antiviral agent does not inhibit HCV-induced autophagy.

According to some embodiments of the invention, the antiviral agent is selected from the group consisting of ribavirin, viramidine, boceprevir, telaprevir, NM-107, valopicitabine, and alisporivir, and any combination thereof.

According to some embodiments of the invention, the method further comprises co-administering to the subject a therapeutically effective amount of an interferon-α.

According to some embodiments of the invention, the amount of hydroxychloroquine sufficient to inhibit HCV-induced autophagy is in a range of from 400 to 2000 mg per day.

According to some embodiments of the invention, the treatment further comprises co-administering a therapeutically effective amount of an antiviral agent.

According to some embodiments of the invention, the therapeutically effective amount of hydroxychloroquine is sufficient to inhibit HCV-induced autophagy in the subject.

According to some embodiments of the invention, the therapeutically effective amount of hydroxychloroquine is in a range of from 500 to 1000 mg per day.

According to some embodiments of the invention, the method further comprises co-administering to the subject a therapeutically effective amount of an additional anti-viral agent.

According to some embodiments of the invention, the additional antiviral agent is selected from the group consisting of an interferon, a viral protease inhibitor, an NS4A inhibitor, an NS5A inhibitor, a viral polymerase inhibitor, a cyclophilin inhibitor, a helicase inhibitor, a glycosylation inhibitor, and an antiphospholipid antibody.

According to some embodiments of the invention, the therapeutically effective amount of ribavirin is in a range of from 50 to 1200 mg per day.

According to some embodiments of the invention, the disease is caused by an HCV genotype that is resistant to the antiviral agent.

According to some embodiments of the invention, the method further comprises co-administering to the subject an additional anti-viral agent.

According to some embodiments of the invention, the additional antiviral agent is selected from the group consisting of an interferon, a viral protease inhibitor, an NS4A inhibitor, an NS5A inhibitor, a viral polymerase inhibitor, a cyclophilin inhibitor, a helicase inhibitor, a glycosylation inhibitor, and an antiphospholipid antibody, and any combination thereof.

According to some embodiments of the invention, the treatment comprises administration of hydroxychloroquine in an amount sufficient to inhibit HCV-induced autophagy.

According to some embodiments of the invention, the treatment comprises administration of from 400 to 2000 mg per day of hydroxychloroquine.

According to some embodiments of the invention, the treatment comprises administration of from 500 to 1000 mg per day of hydroxychloroquine.

According to some embodiments of the invention, the antiviral agent is a viral protease inhibitor.

According to some embodiments of the invention, the viral protease inhibitor is boceprevir.

According to some embodiments of the invention, the antiviral agent is a viral polymerase inhibitor.

According to some embodiments of the invention, the viral polymerase inhibitor is selected from the group consisting of NM-107 and valopicitabine.

According to some embodiments of the invention, the antiviral agent is an interferon.

According to some embodiments of the invention, the interferon is an interferon-α.

According to some embodiments of the invention, the interferon-α is a PEGylated interferon-α.

According to some embodiments of the invention, the therapeutically effective amount of an interferon is in a range of from 50 to 250 µg per week.

According to some embodiments of the invention, the treatment comprises administration of hydroxychloroquine at a dosage of from 400 to 2000 mg per day.

According to some embodiments of the invention, the treatment comprises administration of the interferon at a dosage in a range of from 50 to 250 µg per week.

According to some embodiments of the invention, the treatment further comprises co-administration of a therapeutically effective amount of an additional antiviral agent.

According to some embodiments of the invention, the composition is identified for use in the treatment of a hepatitis C virus (HCV) related disease.

According to some embodiments of the invention, the composition is formulated for oral administration.

According to some embodiments of the invention, the composition is in a solid form.

According to some embodiments of the invention, the composition is a unit dosage form of the composition.

According to some embodiments of the invention, the unit dosage form is identified for use in the treatment of a hepatitis C virus (HCV) related disease.

According to some embodiments of the invention, the unit dosage form is formulated for oral administration.

According to some embodiments of the invention, the unit dosage form is in a solid form.

According to some embodiments of the invention, the unit dosage form comprises an amount of hydroxychloroquine sufficient to inhibit HCV-induced autophagy.

According to some embodiments of the invention, the amount of hydroxychloroquine is sufficient to sensitize hepatitis C virus (HCV) to the antiviral agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to therapy and, more particularly, but not exclusively, to methods and compositions for the treatment of Hepatitis C Virus (HCV) related diseases such as chronic HCV infection.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for a novel methodology for treating HCV related diseases, and chronic HCV infection in particular, which would obviate the non-responsiveness and/or non-tolerance associated with the current methodologies, the present inventors have surprisingly uncovered that hydroxychloroquine (HCQ) can be used as an agent for treating HCV-related diseases, either alone or in combination with one or more anti-viral agents.

As demonstrated in the Examples section that follows, the present inventors have shown that HCQ acts in synergy with anti-viral agents such as interferon-α (IFNα), boceprevir and NM-107, thus providing for an improved therapeutic effect of these agents and/or allowing using lower doses of the antiviral agent(s).

Figure 2:
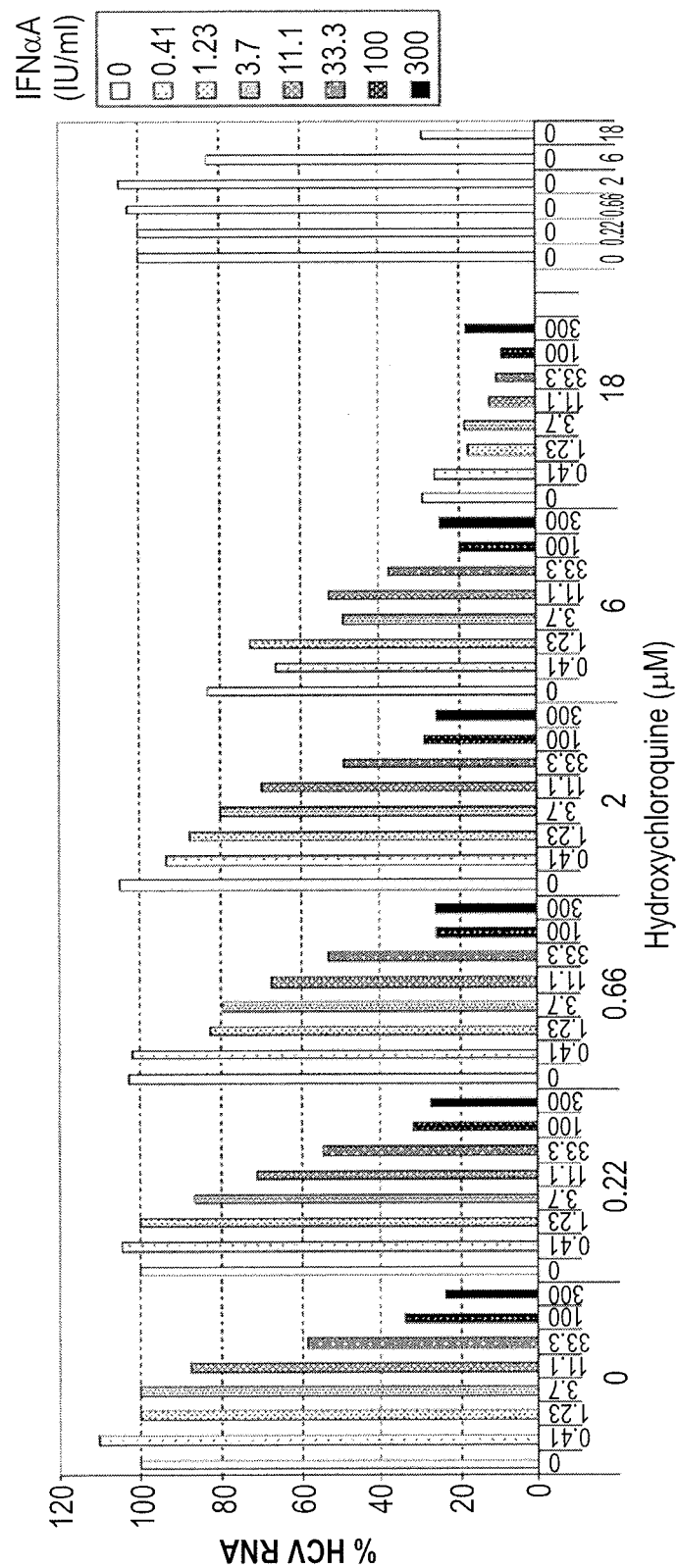
FIG. 2 is a graph showing the level of HCV RNA in replicon cells following treatment for 72 hours with a combination of 0, 0.22, 0.66, 2, 6 or 18 µM hydroxychloroquine with 0, 0.41, 1.23, 3.7, 11.1, 33.3, 100 or 300 IU/ml interferon-α (IFNαA)
Figure 3A:
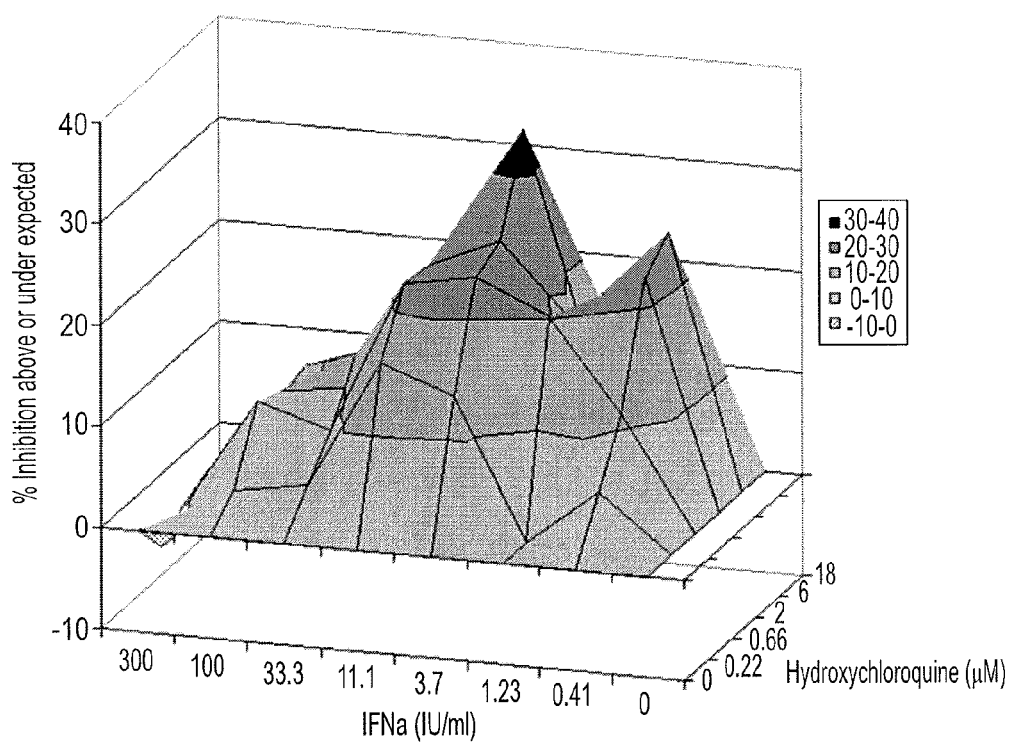
FIGS. 3A and 3B are graphs showing the difference between a measured antiviral effect of a combination of 0, 0.22, 0.66, 2, 6 or 18 µM hydroxychloroquine with 0, 0.41, 1.23, 3.7, 11.1, 33.3, 100 or 300 IU/ml interferon-α (IFNα) and the theoretical antiviral effect expected according to a Prichard-Shipman model of an additive effect (positive values indicate synergy, negative values indicate antagonism); the data is presented in 3-dimensional (FIG. 3A) and 2-dimensional (FIG. 3B) schemes.
Figure 3B:
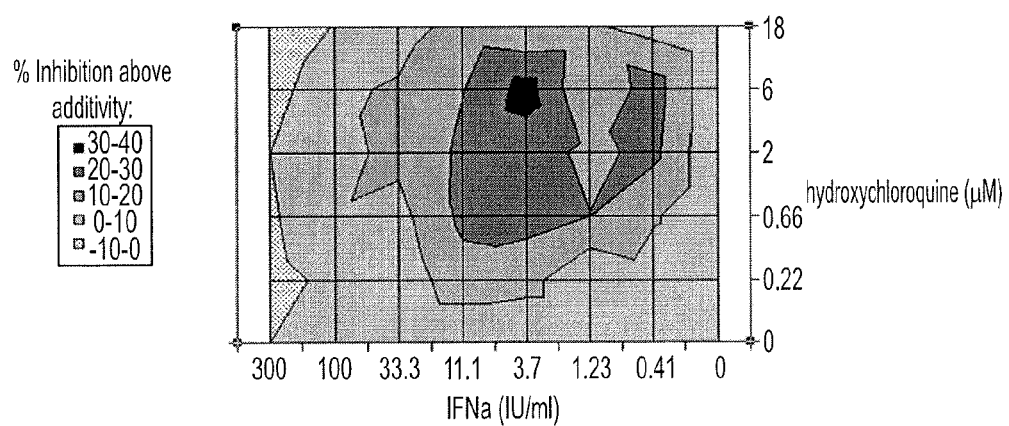
Figure 4:
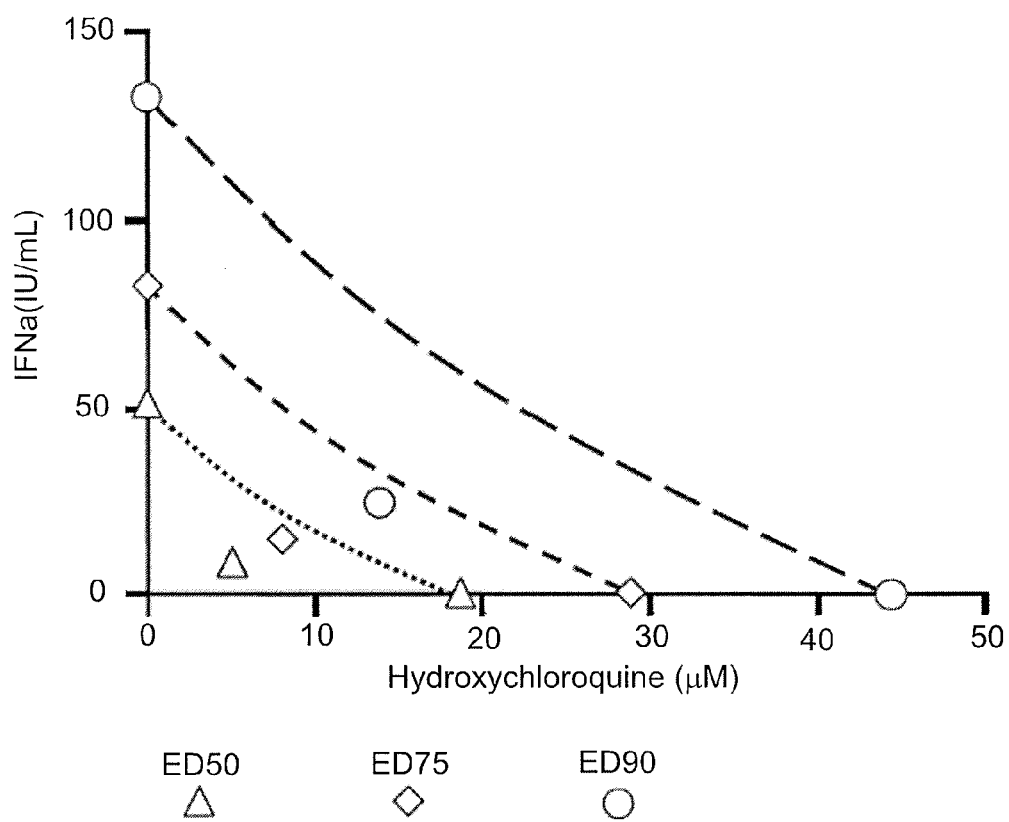
FIG. 4 presents an isobologram showing the concentrations of interferon-α (IFNa) and hydroxychloroquine which provide 50% (ED50), 75% (ED75) and 90% (ED90) antiviral inhibition, as determined experimentally (data points) and as calculated by a theoretical model for an additive effect (dotted lines)
Figure 5:
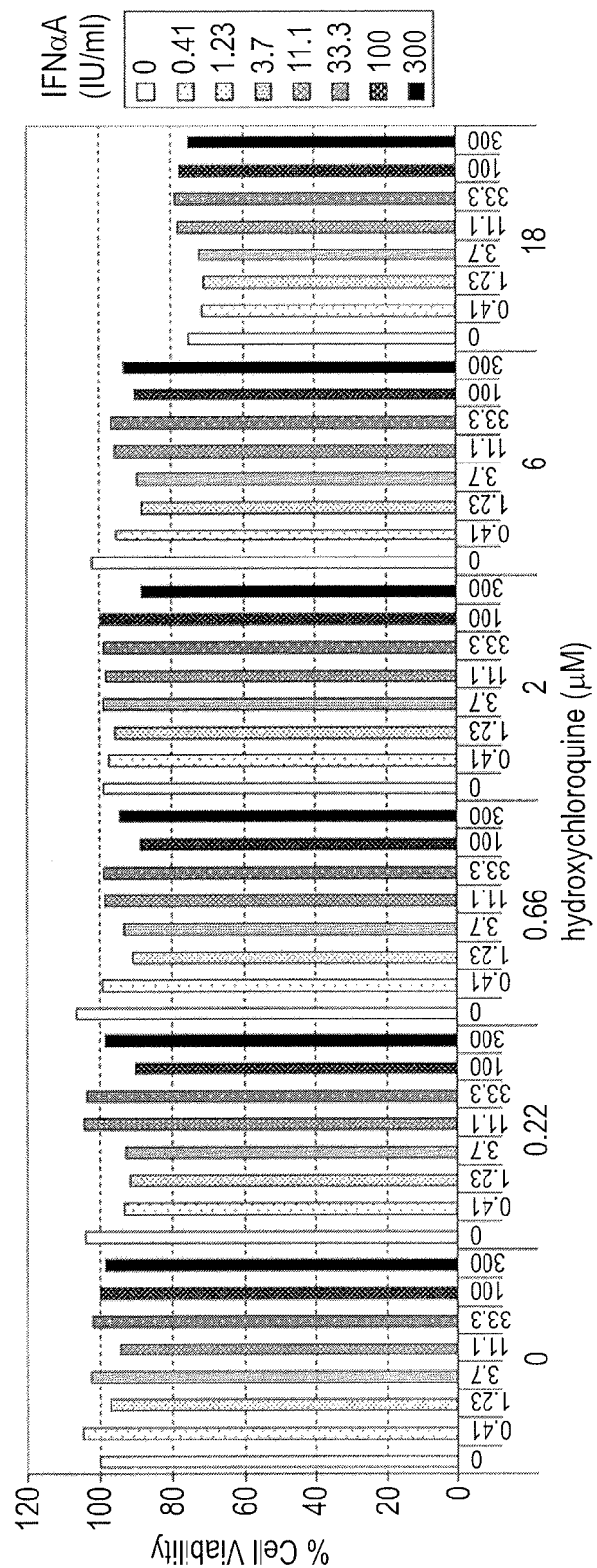
FIG. 5 is a graph showing the viability of HCV replicon cells following treatment for 72 hours with a combination of 0, 0.22, 0.66, 2, 6 or 18 µM hydroxychloroquine with 0, 0.41, 1.23, 3.7, 11.1, 33.3, 100 or 300 IU/ml interferon-α (IFNαA)

Thus, it is demonstrated herein that exemplary combinations of HCQ and IFNα exhibit a synergistic effect, as determined by various theoretical models (FIGS. 2-4 and Table 1). In addition, it is demonstrated that exemplary combinations of HCQ and IFNα exhibit an antiviral effect even at concentrations of HCQ and/or IFNα which do not exhibit an antiviral effect when administered alone (FIG. 2). Exemplary combinations which exhibited the aforementioned synergistic effects were non-toxic (FIG. 5). Furthermore, it was demonstrated that chloroquine does not exhibit the same synergistic effects as HCQ (FIG. 6), indicating that the aforementioned advantageous properties of HCQ are not a general property of chloroquine-related compounds.

Further it is demonstrated that exemplary combinations of HCQ and antiviral agents such as boceprevir (a protease inhibitor) and NM-107 (HCV polymerase inhibitor) exhibit a synergistic effect.

It has been shown that synergy was best achieved when cells were treated with HCQ at a concentration of about 6 μM (See, for example, FIGS. 3A-3B, and 13A-14B). This dose can be translated, using recognized conversion factors, into a dose of about 910 mg for an average human weighing 70 Kg.

While exploring the mechanism of action of HCQ, the present inventors have demonstrated that HCQ treatment effectively reduces the expression level of several HCV-induced NF-κB signaling, ER stress, autophagy and p53 signaling pathways. In addition, it has been demonstrated that IFN and HCQ have a similar repressive effect on these HCV-induced pathways. Without being bound by any particular theory, these findings suggest that the HCQ inhibitory modulations of the HCV-activated biological pathways reflect a consequence of an upstream antiviral event efficiently triggering the HCV eradication.

Figure 7:
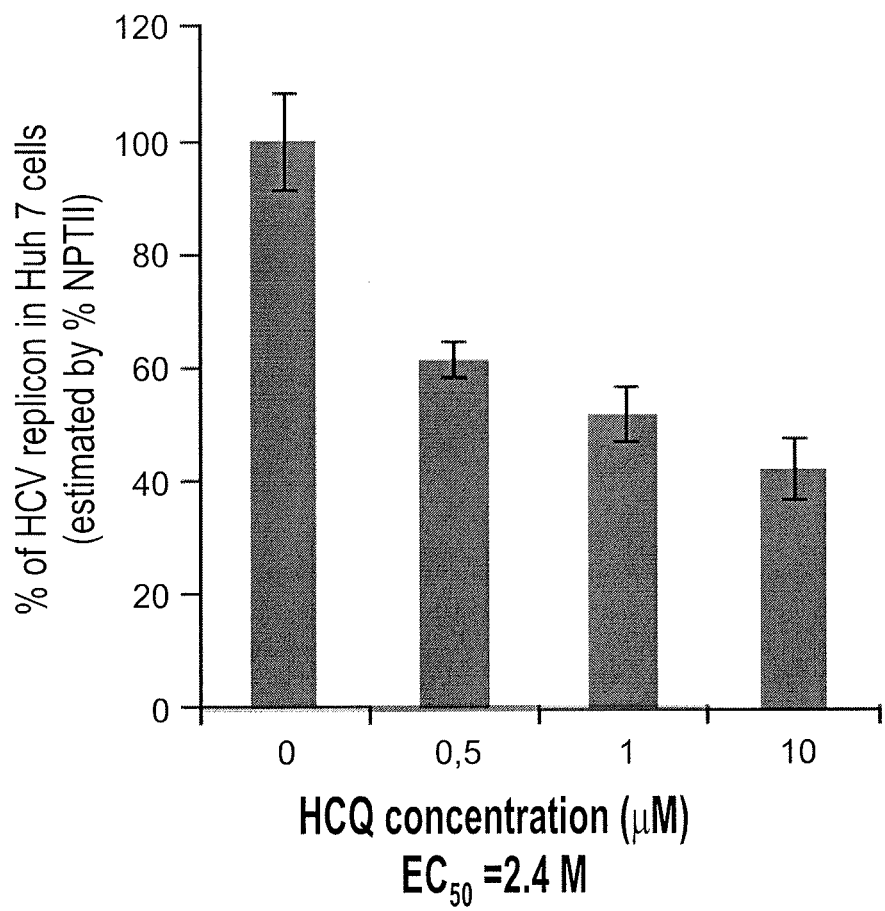
FIG. 7 is a bar graph showing the level of HCV RNA in replicon cells following treatment for 72 hours with a combination of 0, 0.5, 1 or 10 µM hydroxychloroquine (HCQ), as determined by quantification of a replicon-borne neomycin gene product (NPTII)
Figure 8:
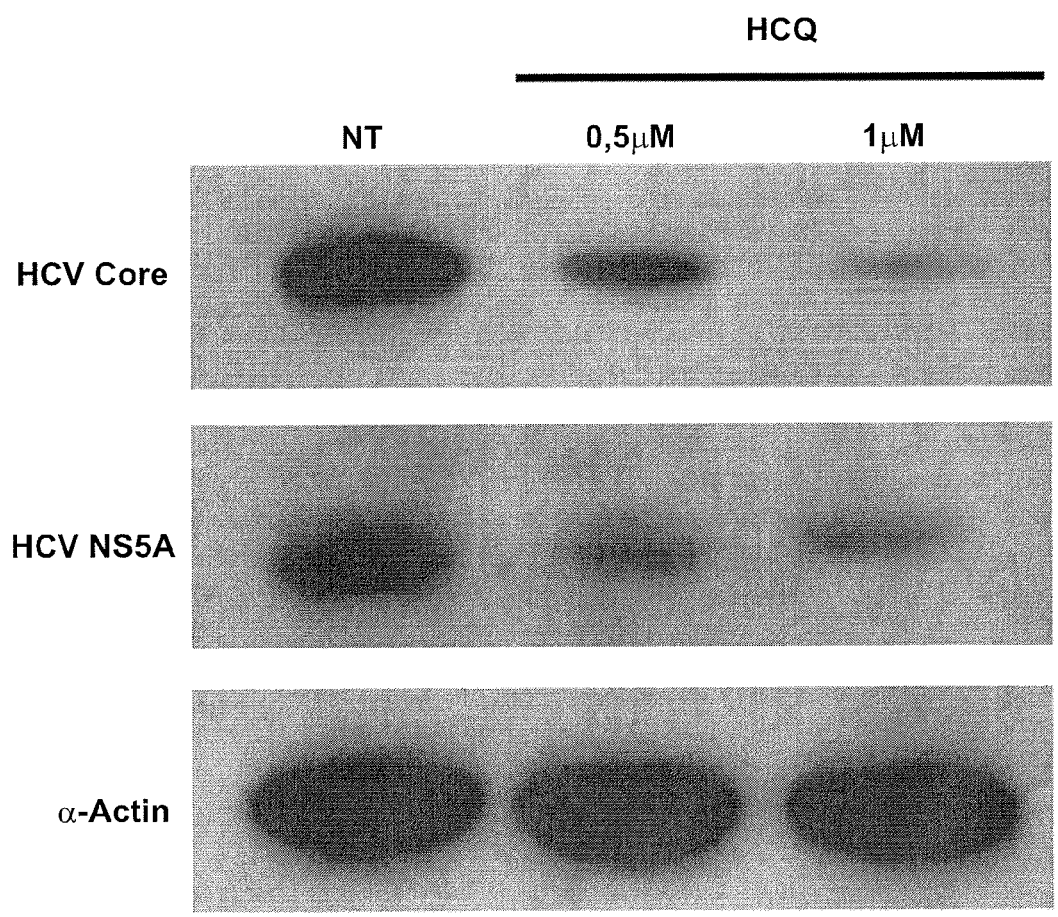
FIG. 8 is an image of a Western blot showing levels of HCV core protein and HCV NS5A protein following treatment of Huh7 replicon cells for 48 hours with 0.5 or 1 µM hydroxychloroquine (HCQ) or without treatment (NT) (α-actin served as a loading control)

Preliminary analysis demonstrated that HCQ treatment leads concomitantly to 1) a dose-dependent decrease in the number of HCV infected cells (FIG. 7), 2) a dose-dependent decrease of levels of HCV NS5A and core protein (FIG. 8), and 3) a decrease in the level of mRNA for several NF-κB related genes, particularly 24 hours after treatment initiation (Tables 2-3). The HCQ-induced reduction of the NS5A and the HCV core protein levels is in agreement with the decrease observed in expression of several NF-κB related genes (e.g. RELB, NFKB2, CXCL5 and CYR61).

Interestingly, it has been previously reported that the NS5A and the HCV core protein can lead to the activation of the NF-κB through distinct signaling pathways: Ca2+ disturbance resulting from an endoplasmic reticulum (ER) stress or through TNF signaling, respectively. Others studies have demonstrated several lines of evidence of the NF-κB pathway activation in HCV infection both in vitro and in vivo. Thus, constitutive activation of NF-κB by HCV might have implications in chronic liver disease including hepatocellular carcinoma associated with HCV infection.

Figure 9A:
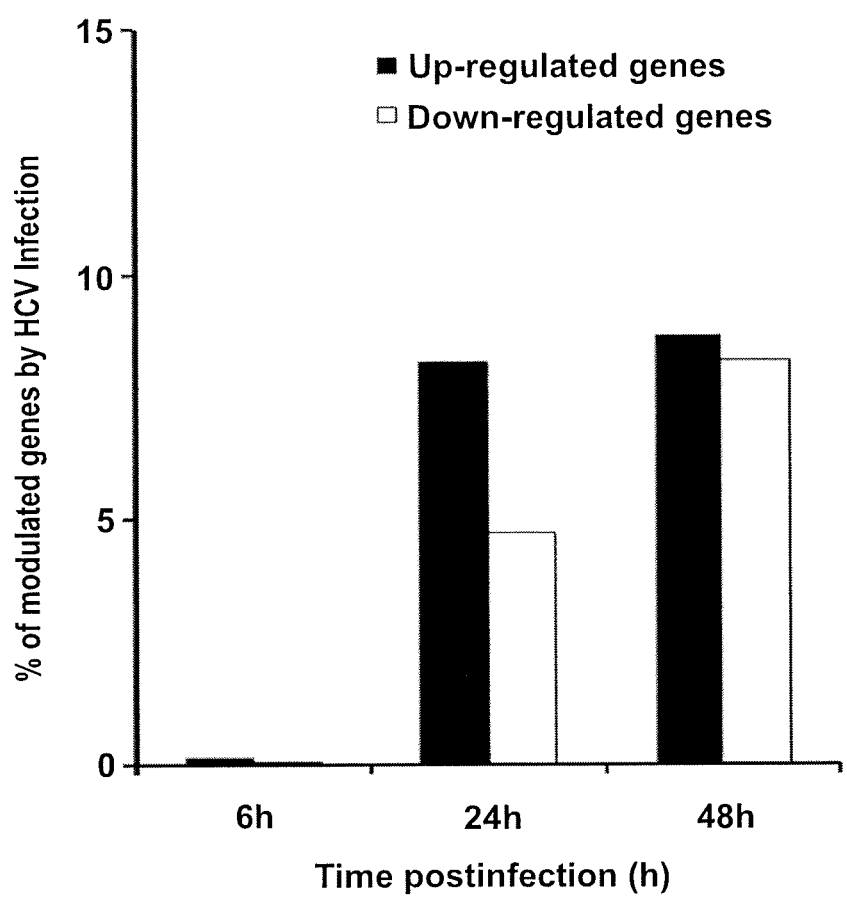
FIG. 9A is a bar graph showing the percentage of host genes (out of a total of 10238 significantly expressed genes) which are modulated (up-regulated or down-regulated) in Huh7 cells 6, 24 or 48 hours after HCV infection with JFH/CsN6A4 viral particles.
Figure 9B:
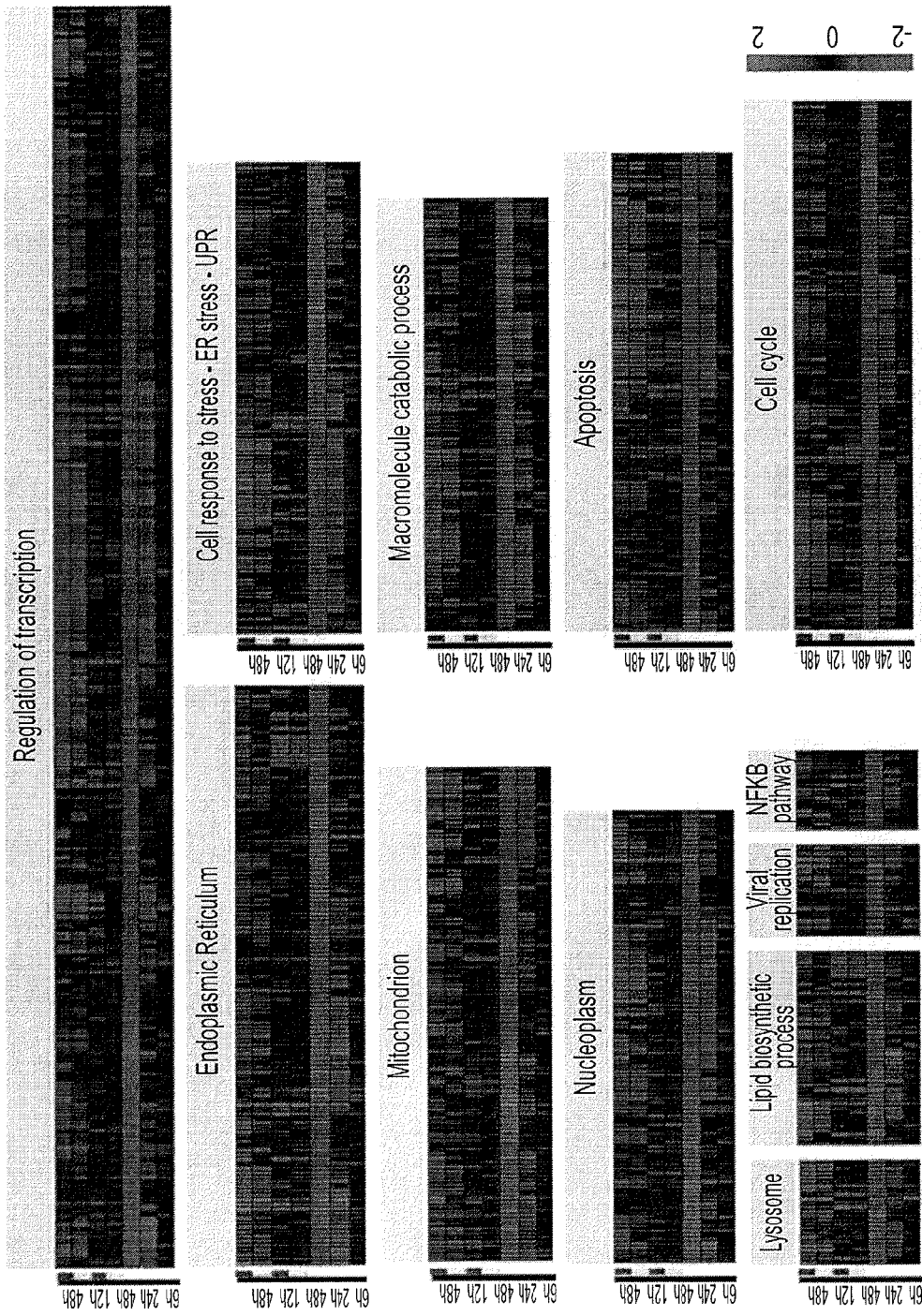
FIG. 9B shows the expression profiles of host genes modulated in Huh7 cells 6, 24 or 48 hours after HCV infection with JFH/CsN6A4 viral particles, or 12 or 48 hours after HCV infection with treatment with HCQ (yellow bar) or CQ (blue bar); red indicates up-regulation, green indicates down-regulation, and black indicates no modulation.
Figure 10:
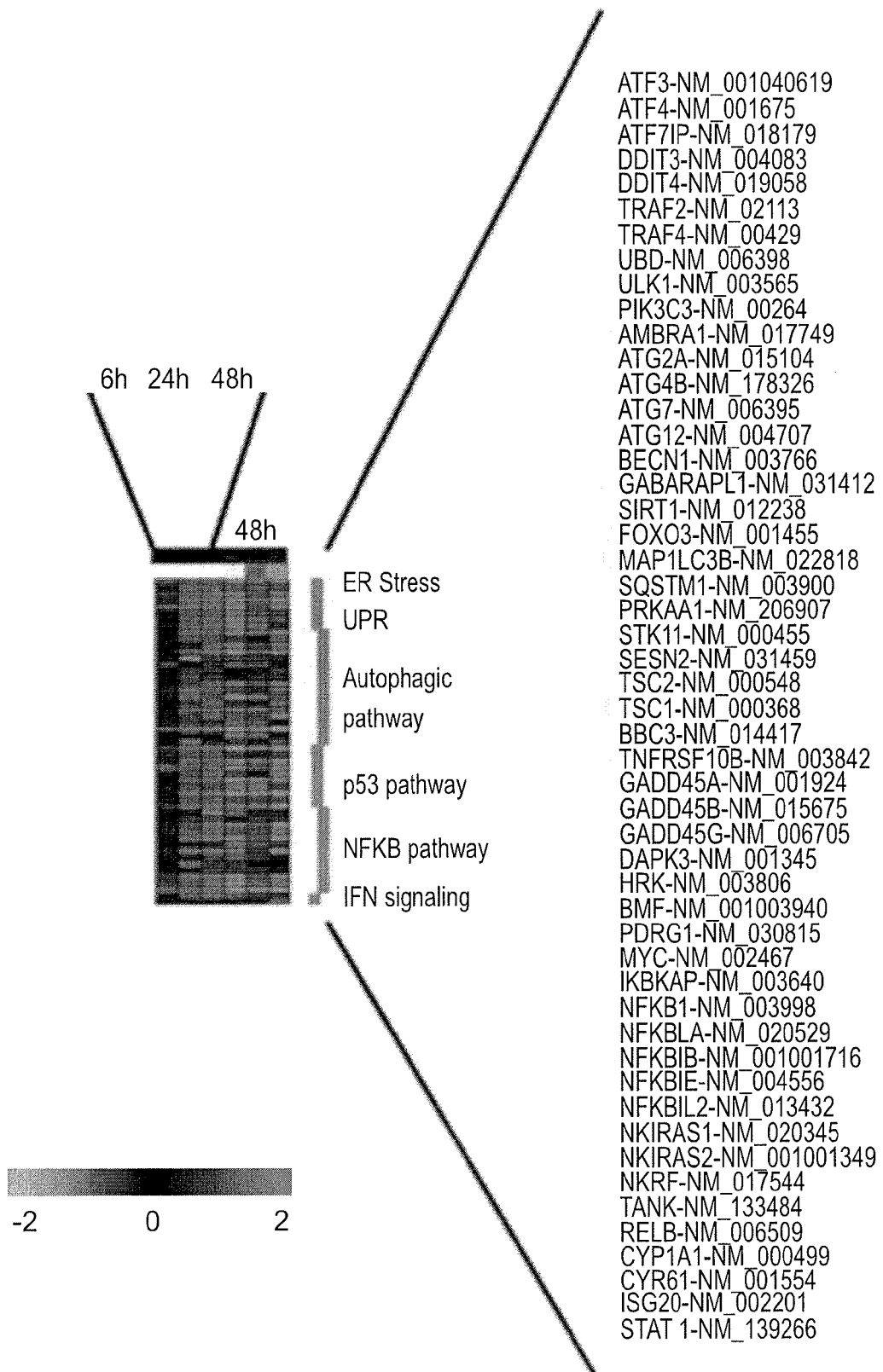
FIG. 10 shows a set of 57 genes involved in the gene regulatory network, and HCQ (blue bar) and CQ (yellow bar) repression in Huh7 cells 48 hours after infection with JFH/CsN6A4 viral particles (expression 6, 24 and 48 hours after infection, without HCQ or CQ treatment is shown for comparison; red bar indicates expression in infected cells treated with interferon-α)

Further gene expression analysis performed on the JFH1 HCVcc model, an accurate model of physiological HCV infection, revealed that HCV infection increases the expression of several NF-κB related genes, as expected. Moreover, in agreement with previous findings using a HCV replicon model, it was demonstrated that HCQ treatment severely reduces expression of these HCV-induced NF-κB related genes, such as RELB, CYR61, CXCL5 (previously found repressed by HCQ treatment of HCV replicon cells), BCL3, CY1PA1, NFKBIA,B,E and NKIRAS1 (FIGS. 9B and 10). Altogether, these findings demonstrate that HCQ counteracts the HCV-induced increase of expression levels of NF-κB related genes. Furthermore, comparison with expression ratios obtained following chloroquine treatment showed that HCQ is more effective than chloroquine at counteracting the HCV-induced increase.

Figure 9C:
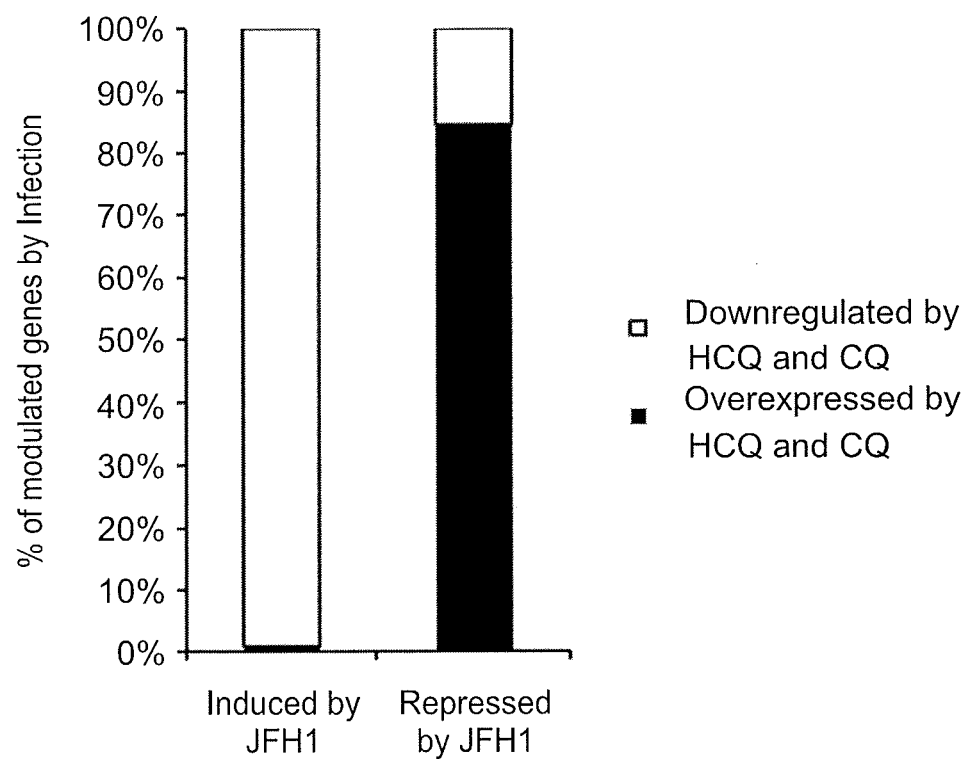
FIG. 9C is a bar graph showing the modulation of 118 genes, out of the 1736 modulated (induced or repressed) 48 hours after HCV infection with JFH/CsN6A4 viral particles, which were overexpressed or down-regulated (at least a 2-fold modulation in expression) 48 hours after HCQ and CQ treatment (each bar represents the proportion of genes modulated by treatment among the HCV-induced genes or among the HCV-repressed genes; white indicates the proportion of genes down-regulated by treatment, black indicates the proportion of genes up-regulated by treatment)

In addition, global gene expression profiling demonstrates that HCV infection induced several others pathways, including ER stress/UPR (unfolded protein response) and the p53 signaling apoptotic cell death, and also cell cycle and lipid metabolism pathways (FIG. 9B). Interestingly, similarly to NF-κB, for all these processes, HCQ treatment modulated the process in the opposite manner to which HCV infection modulated the process, particularly 48 hours post-infection and treatment (FIGS. 9A-9C).

118 genes were determined to undergo at least a twofold change under both of the following conditions: HCV infection, and HCQ and hydroxychloroquine treatment, after 48 hours. It was demonstrated that most of these genes are genes whose expression is up-regulated by HCV and down-regulated by HCQ treatment (FIG. 9C and Table 5). Results obtained using both HCV replicon (Table 2) and HCVcc (Tables 4-5) models were in agreement, indicating that HCQ acts primarily as a transcriptional repressor, with considerably more down-regulation being observed than up-regulation.

Of the abovementioned 118 genes, 57 genes were found to be particularly significant, in that they were differentially expressed in the aforementioned two study conditions, or found to be functionally related to significant genes according to the text-mining based analysis performed using Predict-Search™ (Table 6).

Figure 11:
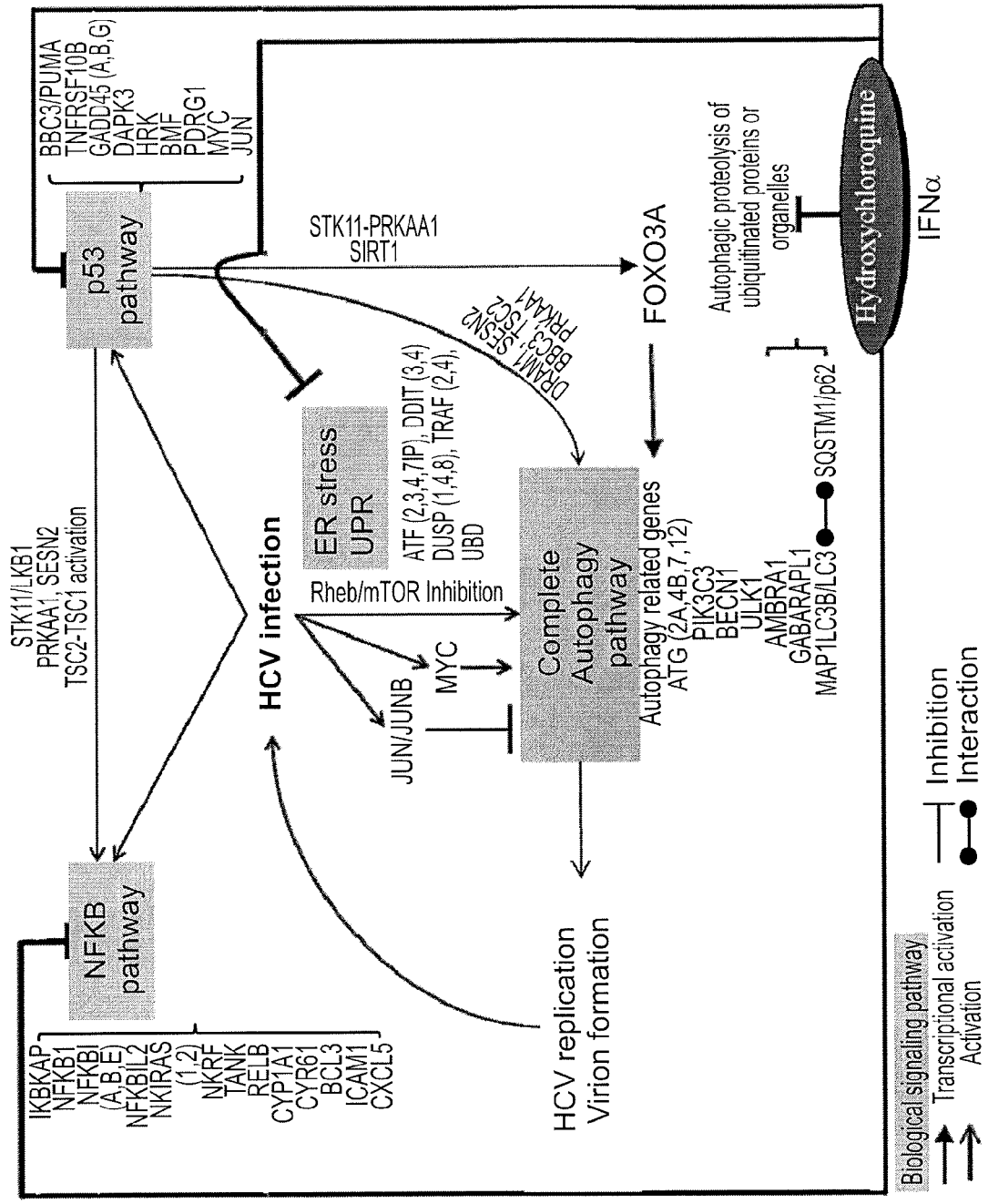
FIG. 11 is a gene network showing HCQ inhibition of HCV-induced pathways.
Figure 12:
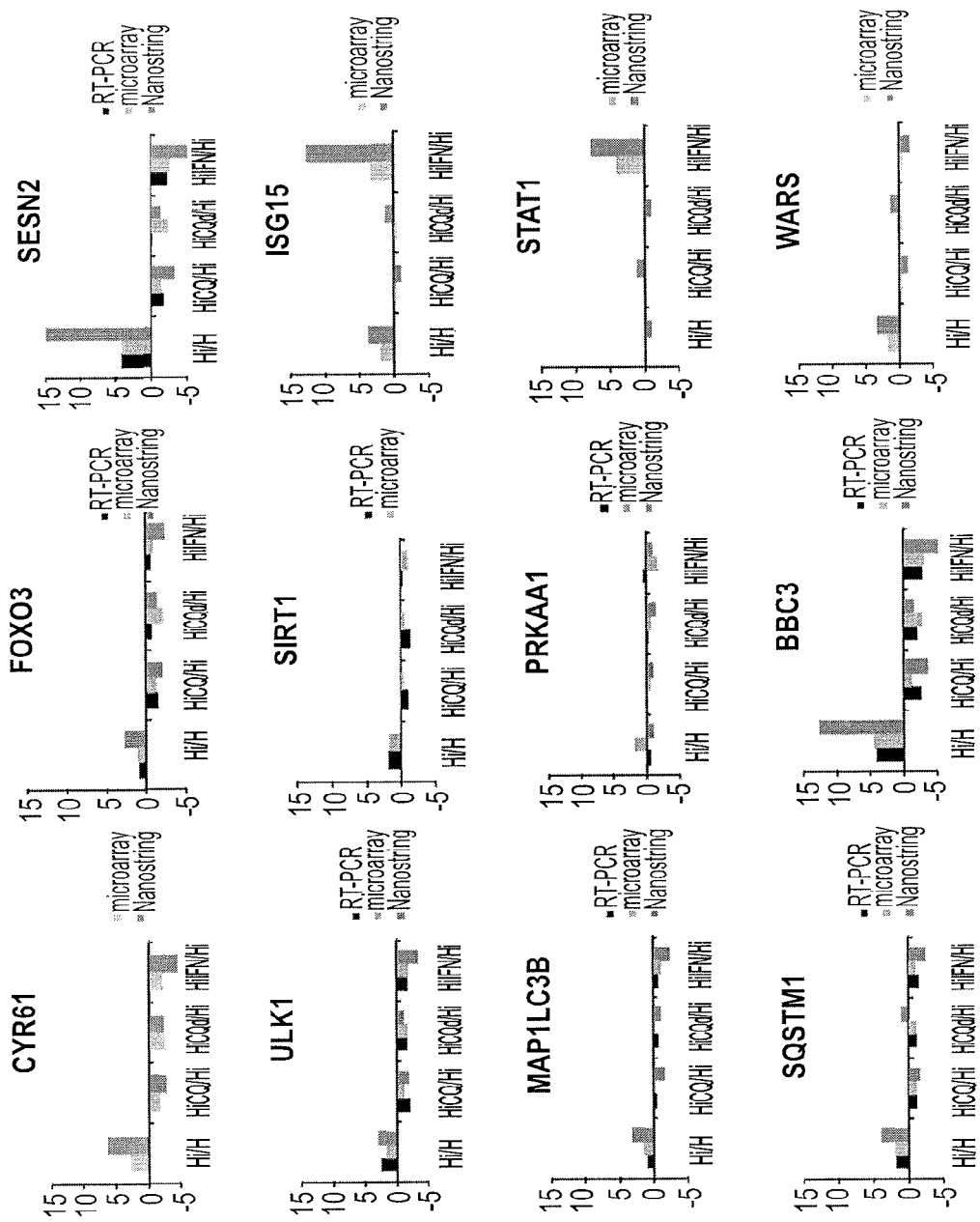
FIG. 12 shows expression of exemplary modulated genes in infected cells (Hi/H), and in infected cells treated with HCQ (HiCQd/Hi), CQ (HiCQ/Hi) or interferon-α (HiIFN/Hi), as determined by microarray analysis, SYBRGreen qRT-PCR, and Nanostring techniques.

Based on the obtained results, a gene regulatory network was constructed showing the inhibitory effect of HCQ treatment on JFH1-induced Huh7 gene expression modulations (FIG. 11). As shown in FIG. 11, a significant result of HCQ treatment is the inhibition of the autophagy pathway (as a result of inhibition of upstream NF-κB, p53 and ER stress/UPR signaling), which interferes with HCV replication.

The above-described findings suggest that treatment of an HCV related disease such as an HCV infection can be beneficially effected while utilizing HCQ in an amount sufficient to inhibit HCV-induced autophagy.

Since autophagy is a pathway which is unrelated to the HCV genotype, these findings further indicate a role of HCQ in the treatment of resistant HCV genotypes, which are otherwise characterized by low responsiveness to current therapy. Moreover, these findings suggest a role for HCQ in a combined HCV treatment with anti-viral agents, via an additive and even synergistic effect of the HCQ and the anti-viral agent(s) and/or via sensitizing the HCV to the antiviral agent, presumably by inhibiting HCV-induced pathways such as HCV-induced autophagy.

It was further shown in the Examples that co-administration of HCQ is capable of potentiating the activity of anti-HCV agents such as PEGylated interferon and ribavirin in the treatment of HCV-infected patients which failed to respond to a standard of care treatment.

It is further noted that HCQ is known as a less toxic derivative of chloroquine. Thus, higher doses of HCQ can be used, compared to chloroquine.

According to an aspect of some embodiments of the present invention there is provided a method of treating a hepatitis C virus (HCV) related disease in a subject in need thereof. The method, according to this aspect of the present invention, is effected by administering to the subject a therapeutically effective amount of hydroxychloroquine (HCQ) or a pharmaceutically acceptable salt thereof.

In some embodiments, the therapeutically effective amount of HCQ is an amount sufficient to inhibit HCV-induced autophagy in the subject, thereby treating the HCV related disease.

As used herein throughout, the term "hepatitis C virus", abbreviated HCV, describes an enveloped, positive-sense single-stranded RNA virus of the family Flaviviridae, which is the cause of hepatitis C in humans, and encompasses all genotypes of the virus, unless otherwise indicated.

Currently known HCV genotypes include genotypes 1, 2, 3, 4, 5 and 6, of which genotypes 1 and 4 are relatively non-responsive to existing treatments (e.g., interferon and ribavirin), whereas genotypes 2, 3, 5 and 6 are more responsive to treatment.

In some embodiments, the HCV related disease is an infection caused by HCV, including all genotypes of HCV, as defined herein.

In some embodiments, the infection caused by HCV is an acute infection, encompassing any acute phase of an HCV infection (e.g., the first 6 months after infection), also termed herein and in the art "acute HCV infection".

An "acute HCV infection" thus relates to an infection which has been eliminated, namely, to cases where viral replication has been eliminated and the virus is eradicated.

If viral replication is not successfully inhibited within the acute phase, the HCV infection is considered a chronic infection.

In some embodiments, the infection caused by HCV is a chronic infection, also termed herein and in the art "chronic HCV infection".

In some embodiments, treating an HCV infection encompasses treating an acute HCV infection, and preventing an acute HCV infection from being considered as a chronic HCV infection.

As used herein throughout, the phrase "HCV related disease" also encompasses any disease or disorder associated with an HCV infection, including symptoms associated with an acute HCV infection, such as decreased appetite, fatigue, abdominal pain, jaundice, itching and flu-like symptoms, as well as symptoms associated with a chronic HCV infection, such as fatigue, flu-like symptoms, joint pains, arthritis, polyarthralgia, cutaneous leukocytoclastic vasculitis, neuropathy, itching, sleep disturbances, appetite changes, nausea, depression, liver cirrhosis, ascites, a tendency towards bruising and/or bleeding, varices, jaundice, hepatic encephalopathy, porphyria cutanea cardia, cryoglobulinemia, glomerulonephritis (e.g., membranoproliferative glomerulonephritis), thrombocytopenia, lichen planus, diabetes mellitus, and lymphoproliferative disorders.

Some types of HCV related disease are inflammatory conditions (e.g., arthritis) which may be treated by a relatively simple anti-inflammatory therapy. However, other types of HCV related disease may be more difficult to treat.

In some embodiments, the phrase "HCV related disease" refers to an HCV disease other than such inflammatory conditions (e.g., other than arthritis).

In addition, disease caused by an HCV genotype resistant to an antiviral agent (antiviral-resistant) may be particularly difficult to treat successfully.

Currently known resistant HCV genotypes include genotype 1 HCV and genotype 4 HCV. These genotypes are known in the art to exhibit resistance to antiviral agents commonly used to treat HCV related disease.

In some embodiments, the HCV related disease is caused by an antiviral-resistant HCV genotype.

Resistance can be inherent to an organism or acquired (e.g., as a result of exposure to an antiviral agent resulting in selection for a mutant genotype resistant to the agent). When resistance is acquired upon exposure to an antiviral agent, the resistance may be specific to that antiviral agent (and in some cases highly similar antiviral agents), or the acquired resistance may to a variety of antiviral agents, including antiviral agents to which the organism was not exposed.

As used herein, a "subject" describes any mammal afflicted, or suspected as being afflicted, by an HCV related disease as described herein, and/or to whom the treatment methods described herein are desired, including human, bovine, equine, canine, murine and feline subjects. In some embodiments, the subject is a human.

In some embodiments, "a subject in need thereof" is a subject diagnosed as having an HCV-related disease. Determining an HCV-related disease can be made by blood tests for detecting antibodies to HCV, and molecular nucleic acid tests for detecting the presence of HCV (e.g., polymerase, chain reaction, transcription mediated amplification and/or branched DNA methods). Optionally, both antibody and nucleic acid tests are used, in order to confirm that an HCV infection is present. The particular HCV-related disease can be determined by a physician using standard methods (e.g., physical examination, liver function tests), depending on which symptoms are present in a subject.

In some embodiments "a subject in need thereof" is a subject who is afflicted by an HCV-related disease, such as chronic HCV infection, and who was treated with an antiviral agent or a combination of anti-viral agents, but was identified as non-responsive to the treatment or as non-tolerant to the treatment.

In some embodiments, the subject is an HCV-infected subject (i.e., a subject who is afflicted by an HCV infection), and who is identified as being non-responsive to an anti-HCV therapy. In some embodiments, the subject is identified as being non-responsive to an anti-HCV therapy which is a treatment with PEGylated interferon-α-2a or PEGylated interferon-α-2b, in combination with ribavirin.

As used herein, the term "non-responsive" refers to a failure of an antiviral therapy used in the art against HCV (e.g., a treatment with PEGylated interferon-α-2a or PEGylated interferon-α-2b, in combination with ribavirin), and optionally a failure of two such antiviral therapies, to abrogate, substantially inhibit, slow or reverse the progression of an HCV-related disease, or substantially ameliorating clinical symptoms of an HCV-related disease.

In some embodiments, an HCV-infected subject is identified as non-responsive to an anti-HCV therapy, when the subject is lacking a sustained virological response (SVR), as determined in the art, to the anti-HCV therapy.

In some embodiments, non-responsiveness to treatment is a result of an HCV (e.g., an HCV genotype) which is resistant to the therapy. Alternatively or additionally, non-responsiveness is due to the subject (e.g., physiology of the subject, poor compliance by the subject). In some embodiments, the reason(s) for non-responsiveness are not known.

In some embodiments, the HCV-infected subject is infected by genotype 1 HCV. In exemplary embodiments, the HCV-infected subject is infected by genotype 1b HCV.

As used herein, the term "non-tolerant" refers to the development of one or more adverse effects in a treated subject, which are judged by a physician to be due to the treatment, wherein the adverse effects are sufficiently severe such as to require ending or altering the treatment (e.g., by reducing the dosage of the anti-viral therapy and/or by replacing the anti-viral therapy).

It is to be appreciated that a subject may be non-responsive and non-tolerant to treatment. Thus, for example, a subject may be non-tolerant of relatively high dosages of an antiviral agent (e.g., dosages of PEGylated interferon-α and/or ribavirin) used in the art, while also being non-responsive to relatively low dosages of an antiviral agent used in the art, such that the subject is non-tolerant and/or non-responsive to all possible dosages of the antiviral agent.

As used herein and is known in the art, the term "autophagy" describes a process in cell biology (also known in the art as "autophagocytosis") involving degradation of a cell's own components via the lysosomal machinery.

The phrase "HCV-induced autophagy" describes autophagy in a cell which is due to infection of the cell by HCV.

As used herein, the phrases "an amount sufficient to inhibit HCV-induced autophagy" and "an amount that inhibits HCV-induced autophagy" are used interchangeably, and encompass an amount of HCQ or of a salt thereof which reduces HCV-induced autophagy by at least 20%, at least 30%, at least 40%, at least 50%, at least 60%, at least 70%, at least 80%, at least 90%, or even which completely abolishes HCV-induced autophagy (i.e., restores levels of autophagy to normal levels). Any integer between 10% and 100% is contemplated in this regard.

HCV-induced autophagy, as well as inhibition of HCV-induced autophagy, can be determined, for example, by identifying autophagy or an autophagy-related process which occurs in infected cells, but not in corresponding non-infected cells.

In some embodiments, HCV-induced autophagy is characterized by an increase in a level of one or more proteins associated with autophagy. Optionally, the increase is characterized by an increase of at least 100%, in expression of the one or more proteins, as determined using standard techniques (e.g., microarray analysis, RT-PCR, and/or NanoString™ gene expression analysis). Exemplary proteins associated with HCV-induced autophagy include, but are not limited to, ULK1, AMBRA1, ATG2A, GABARAPL1, FOX03, SQSTM1, PIK3C3 and MAP1LC3B, which were found to be upregulated in HCV-infected cells.

In some embodiments, HCV-induced autophagy is characterized by an increase (e.g., of at least 100%) of the levels of at least 1, optionally at least 2, optionally at least 3, optionally at least 4, optionally at least 5, optionally at least 6, optionally at least 7, and optionally all 8, of the aforementioned proteins.

In some embodiments, inhibition of HCV-induced autophagy (e.g., inhibition of between 10% and 100%) is characterized by a reduction in an increase (e.g., of at least 100%) of the levels of at least 1, optionally at least 2, optionally at least 3, optionally at least 4, optionally at least 5, optionally at least 6, optionally at least 7, and optionally all 8, of the aforementioned proteins. Thus, for example, a treatment-induced reduction by 90% of an HCV-induced 100% increase in a protein level results in a 10% increase relative to a level in non-infected and non-treated cells.

In some embodiments, autophagy is determined by measuring the arteriovenous amino acid exchange rate in peripheral tissues, as described in Klionsky et al. [Autophagy 2008, 4:151-175], which is incorporated by reference as if fully set forth herein.

As used herein, the term "hydroxychloroquine" includes the racemic hydroxychloroquine, which is 2-[[4-[(7-chloro-4-quinolinyl)amino]pentyl]ethylamino]ethanol as disclosed in U.S. Pat. No. 2,546,658, or any of the single enantiomers "(S)-(+) hydroxychloroquine" or "(R)-(−) hydroxychloroquine" as disclosed in U.S. Pat. No. 5,314,894. This term may relate either to the free form of hydroxychloroquine or to any pharmaceutically acceptable salt thereof, such as hydroxychloroquine sulfate.

Herein, the term "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. Examples, without limitation, of pharmaceutically acceptable salts include salts comprising an anion such as a carboxylate or sulfate anion, and/or a cation such as, but not limited to, ammonium, sodium, potassium and the like. Suitable salts are described in, e.g., Birge et al. [J Pharm Sci 1977, 66:1-19]. An example of pharmaceutically acceptable salt of hydroxychloroquine is hydroxychloroquine sulfate.

Hydroxychloroquine (HCQ) is currently used in treatments of malaria, lupus erythematosus, rheumatoid arthritis, post-Lyme disease arthritis, and Sjogren's syndrome, typically at a daily dose of 200 mg or 400 mg hydroxychloroquine sulfate.

In exemplary embodiments, the hydroxychloroquine is in a form of hydroxychloroquine sulfate (a pharmaceutically acceptable salt of hydroxychloroquine).

Herein, weight amounts of hydroxychloroquine or a pharmaceutically acceptable salt thereof refer to an amount of hydroxychloroquine sulfate which includes the intended amount of hydroxychloroquine per se, in accordance with the widespread use of the sulfate salt in the art. The skilled person will be readily capable of determining an amount of free-base HCQ, or a salt of HCQ other than HCQ sulfate, which will comprise the same amount of HCQ per se as in the recited amount of HCQ sulfate.

Due to its lower toxicity compared to chloroquine, high peak levels of HCQ are considered to be tolerable.

As demonstrated herein, it has been surprisingly found that HCQ inhibits HCV-induced processes associated with autophagy, and is more effective than chloroquine at inhibiting such processes, and is also effective in models of antiviral resistant HCV genotypes.

Without being bound by any particular theory, it is believed that hydroxychloroquine is particularly effective at inhibiting HCV replication by inhibiting HCV-induced autophagy which facilitates HCV replication, and that HCQ can thereby exhibit a strong antiviral effect in an HCV-infected subject.

As used herein, the term "therapeutically effective amount" describes an amount of a compound described herein (alone or in a combination of compounds described herein) which upon being administered will relieve to some extent one or more of the symptoms of the condition being treated.

In the context of some embodiments of the present invention, a "therapeutically effective amount" describes an amount which eradicates or reduces HCV replication. Such an amount can also be defined herein as an amount that prevents an acute HCV infection from turning into a chronic HCV infection.

As indicated herein, embodiments of this aspect of the present invention relate to an amount which inhibits HCV-induced autophagy. Such an amount can be determined, for example, by measuring autophagy in an HCV-infected subject (e.g., as described herein) before and after administration of an amount of HCQ, so as to determine whether a decrease (e.g., a decrease described herein) in HCV-induced autophagy is detected.

In some embodiments, the therapeutically effective amount of HCQ or a salt thereof ranges between 100 mg to 2000 mg per day, including any integer within this range. In some embodiments, the therapeutically effective amount of HCQ or a salt thereof ranges from about 400 mg to about 2000 mg per day. In some embodiments, the therapeutically effective amount of HCQ or a salt thereof ranges from about 500 mg to about 1000 mg per day.

In some embodiments, the therapeutically effective amount of HCQ or a salt thereof is 100 mg per day.

In some embodiments, the therapeutically effective amount of HCQ or a salt thereof is 200 mg per day.

In some embodiments, the therapeutically effective amount of HCQ or a salt thereof is 300 mg per day.

In some embodiments, the therapeutically effective amount of HCQ or a salt thereof is 400 mg per day.

In some embodiments, the therapeutically effective amount of HCQ or a salt thereof is 500 mg per day.

In some embodiments, the therapeutically effective amount of HCQ or a salt thereof is 600 mg per day.

In some embodiments, the therapeutically effective amount of HCQ or a salt thereof is 700 mg per day.

In some embodiments, the therapeutically effective amount of HCQ or a salt thereof is 800 mg per day.

In some embodiments, the therapeutically effective amount of HCQ or a salt thereof is 900 mg per day.

In some embodiments, the therapeutically effective amount of HCQ or a salt thereof is 1000 mg per day.

In some embodiments, the therapeutically effective amount of HCQ or a salt thereof is 1100 mg per day.

In some embodiments, the therapeutically effective amount of HCQ or a salt thereof is 1200 mg per day.

In some embodiments, the therapeutically effective amount of HCQ or a salt thereof is 1300 mg per day.

In some embodiments, the therapeutically effective amount of HCQ or a salt thereof is 1400 mg per day.

In some embodiments, the therapeutically effective amount of HCQ or a salt thereof is 1500 mg per day.

In some embodiments, the therapeutically effective amount of HCQ or a salt thereof is 1600 mg per day.

In some embodiments, the therapeutically effective amount of HCQ or a salt thereof is 1700 mg per day.

In some embodiments, the therapeutically effective amount of HCQ or a salt thereof is 1900 mg per day.

In some embodiments, the therapeutically effective amount of HCQ or a salt thereof is 2000 mg per day.

In some embodiments, the amount of HCQ sufficient to inhibit autophagy is higher than the amount of HCQ required to exert currently known therapeutic effects, including the amount known to date to be therapeutically effective in the treatment of malaria, lupus erythematosus, rheumatoid arthritis, post-Lyme disease arthritis and Sjogren's syndrome, and including an amount considered effective for treating HCV infections.

In some embodiments, the amount of HCQ sufficient to inhibit autophagy is higher than the amount of HCQ required to exert currently known therapeutic effects by at least 10%, and can be, for example, higher by from 10% to about 50% or from about 10% to about 100% or even 200%.

In some embodiments, the amount of HCQ sufficient to inhibit autophagy is higher than the amount of HCQ required for exerting currently known therapeutic effects by at 20%.

In some embodiments, the amount of HCQ sufficient to inhibit autophagy is higher than the amount of HCQ required to exert currently known therapeutic effects by 30%.

In some embodiments, the amount of HCQ sufficient to inhibit autophagy is higher than the amount of HCQ required for exerting currently known therapeutic effects by 40%.

In some embodiments, the amount of HCQ sufficient to inhibit autophagy is higher than the amount of HCQ required for exerting currently known therapeutic effects by 50%.

In some embodiments, the amount of HCQ sufficient to inhibit autophagy is higher than the amount of HCQ required for exerting currently known therapeutic effects by 60%.

In some embodiments, the amount of HCQ sufficient to inhibit autophagy is higher than the amount of HCQ required for exerting currently known therapeutic effects by 70%.

In some embodiments, the amount of HCQ sufficient to inhibit autophagy is higher than the amount of HCQ required for exerting currently known therapeutic effects by 80%.

In some embodiments, the amount of HCQ sufficient to inhibit autophagy is higher than the amount of HCQ required for exerting currently known therapeutic effects by 90%.

In some embodiments, the amount of HCQ sufficient to inhibit autophagy is higher than the amount of HCQ required for exerting currently known therapeutic effects by 100%.

In some embodiments, the amount of HCQ sufficient to inhibit autophagy is higher than the amount of HCQ required for exerting currently known therapeutic effects by 110%.

In some embodiments, the amount of HCQ sufficient to inhibit autophagy is higher than the amount of HCQ required for exerting currently known therapeutic effects by 120%.

In some embodiments, the amount of HCQ sufficient to inhibit autophagy is higher than the amount of HCQ required for exerting currently known therapeutic effects by 150%.

In some embodiments, the amount of HCQ sufficient to inhibit autophagy is higher than the amount of HCQ required for exerting currently known therapeutic effects by 200%.

In some embodiments, the amount of HCQ sufficient to inhibit autophagy is higher than the amount of HCQ required for exerting currently known therapeutic effects by 300%.

In some embodiments, the amount of HCQ sufficient to inhibit autophagy is higher than the amount of HCQ required for exerting currently known therapeutic effects by 400%.

In some embodiments, the amount of HCQ sufficient to inhibit autophagy is higher than the amount of HCQ required for exerting currently known therapeutic effects by 500%.

In some embodiments, the amount of HCQ sufficient to inhibit HCV-autophagy is at least 400 mg per day.

In some embodiments, the amount of HCQ sufficient to inhibit HCV-autophagy is at least 500 mg per day.

In some embodiments, the amount of HCQ sufficient to inhibit HCV-autophagy is at least 600 mg per day.

In some embodiments, the amount of HCQ sufficient to inhibit HCV-autophagy is at least 700 mg per day.

In some embodiments, the amount of HCQ sufficient to inhibit HCV-autophagy is at least 800 mg per day.

In some embodiments, the amount of HCQ sufficient to inhibit HCV-autophagy is at least 900 mg per day.

In some embodiments, the amount of HCQ sufficient to inhibit HCV-autophagy is at least 1000 mg per day.

In some embodiments, the amount of HCQ sufficient to inhibit HCV-autophagy ranges from 500 mg to 1500 mg per day.

In some embodiments, the amount of HCQ sufficient to inhibit HCV-autophagy ranges from 600 mg to 1200 mg per day.

In some embodiments, the amount of HCQ sufficient to inhibit HCV-autophagy ranges from 800 mg to 1200 mg per day.

In some embodiments, the amount of HCQ sufficient to inhibit HCV-autophagy ranges from 600 mg to 1000 mg per day.

In some embodiments, the amount of HCQ sufficient to inhibit HCV-autophagy ranges from 800 mg to 1000 mg per day.

In some embodiments, the amount of HCQ sufficient to inhibit HCV-autophagy ranges from 900 mg to 1100 mg per day.

In some embodiments, the amount of HCQ sufficient to inhibit HCV-autophagy ranges from 850 mg to 950 mg per day.

Any integer between the above-indicated ranges is contemplated.

Herein throughout, whenever an amount of HCQ is indicated, it encompasses the same amount of an HCQ pharmaceutically acceptable salt as described herein, or an equimolar amount of an HCQ pharmaceutically acceptable salt.

Herein throughout, whenever an amount of HCQ or of a salt thereof is indicated as an amount per day, it can be administered once, twice, thrice and even four-times a day.

In some embodiments, the method is effected by administering a therapeutically effective amount of HCQ or a salt thereof once a day.

In some embodiments, the method is effected by administering a therapeutically effective amount of HCQ or a salt thereof once a day.

When administered more than once a day (e.g., twice or thrice a day), the above-indicated amounts are divided to the respective administration times.

For example, in embodiments in which the method is effected by administering an amount of HCQ which is 900 mg per day, and comprises 2 daily administrations, 450 mg of HCQ are used in each administration. Alternatively, one administration is of 400 mg and another is of 500 mg. If such a daily dosage is to be administered 3 times a day, 300 mg of HCQ can be used, as an example, in each administration.

In embodiments in which the method is effected by administering an amount of HCQ which is 600 mg per day, 300 mg of HCQ are used in each of two daily administrations. Alternatively, one administration is of 200 mg and another is of 400 mg. Alternatively, 200 mg of HCQ are used in each of three daily administrations.

In embodiments in which the method is effected by administering an amount of HCQ which is 800 mg per day, and comprises 2 daily administrations, 400 mg of HCQ are used in each administration. Alternatively, one administration is of 200 mg and another is of 600 mg. Alternatively, 200 mg of HCQ are used in each of four daily administrations.

In embodiments in which the method is effected by administering an amount of HCQ which is 1000 mg per day, and comprises 2 daily administrations, 500 mg of HCQ are used in each administration. Alternatively, one administration is of 400 mg and another is of 600 mg. Alternatively, the method comprises 3 daily administrations, for example, two of 400 mg and one of 200 mg. Alternatively, the method comprises 4 daily administrations, for example, wherein each administration is of 250 mg.

The method described herein can be utilized for treating an HCV-related disease by administering HCQ or salt thereof, as described herein. However, either or both the therapeutic effect of HCQ in treating HCV-related diseases and the effect of HCQ in inhibiting HCV-induced autophagy can further be utilized in a combined therapy, where HCQ or the salt thereof is used in combination with one or more anti-viral agents.

As demonstrated herein, such a combined therapy provides for at least an additive therapeutic effect exhibited by both agents and in some embodiments provides for a synergistic therapeutic effect, as described in further detail hereinafter.

In some embodiments, such a combined therapy provides for enhancing the effect of the antiviral agent, via the inhibition of the HCV-induced autophagy.

Without being bound by any particular theory, it is suggested that the upregulated autophagy demonstrated herein in various HCV models reduces the therapeutic effect of the anti-viral agent, and therefore inhibiting the HCV-induced autophagy increases the therapeutic effect of the anti-viral agent and can even be regarded, at least in some cases, as sensitizing the HCV towards the anti-viral agent.

Thus, in some embodiments, the method described herein is further effected by co-administering to the subject (e.g., an HCV-infected subject) HCQ or a salt thereof in an amount as indicated hereinabove, and a therapeutically effective amount of at least one antiviral agent.

Herein, the term "antiviral agent" encompasses any active compound or mixture of active compounds which is active against viruses, in particular HCV, and includes, but is not limited to, ribavirin and derivatives and prodrugs thereof (e.g., viramidine); interferons (e.g., interferon-α); viral protease inhibitors (e.g., boceprevir, SCH 503034, telaprevir, ITMN B, BILN 2061, SCH 6); NS4A inhibitors (e.g., GS-9132); NS5A inhibitors; viral polymerase inhibitors, including nucleoside and non-nucleoside polymerase inhibitors (e.g., NM-107 and its prodrug valopicitabine (NM-283), R1626/R1479, HCV-796, BILB 1941, R7128/PS16130, GSK625433, A-848837, BCX-4678, GL59728, GL60667, NV-008, HCV-086, R803, JTK 003, XTL-2125); cyclophilin B inhibitors (e.g., alisporivir (DEBIO-025), NIM811); helicase inhibitors (e.g., QU665); glycosylation inhibitors (e.g., celgosivir (MX-3253)); an antiphospholipid antibody (e.g., bavituximab); and any combination thereof.

In some embodiments, the at least one anti-viral agent is selected from the group consisting of a ribavirin, a viral protease inhibitor, a viral polymerase inhibitor, an NS4A inhibitor, and a NS5A inhibitor.

The term "anti-viral agent" as used herein encompasses prodrugs, pharmaceutically acceptable salts, hydrates, solvates and pharmaceutically active derivatives of any of the exemplary agents described herein.

Examples of antiviral agents suitable for use according to embodiments of the invention include:

PEGylated interferon alfa-2a (e.g., PEGASYS®); Interferon alfacon-1 (e.g., INFERGEN®); Natural interferon (e.g., OMNIFERON®); ALBUFERON®; Interferon beta-1a (e.g., REBIF®); Omega interferon (available from BioMedicine); Oral interferon alpha (available from Amarillo Biosciences); Interferon gamma-1b (available from InterMune); IP-501 (available from Interneuron); Merimedodib VX-497 (Vertex); Amantadine; IDN-6556 (Idun Pharma.); XTL-002 (XTL); HCV/MF59 (Chiron); Civacir (NABI); Viramidine (ICN); thymosin alfa-1 (e.g., ZADAXIN) (Sci Clone); histamine dihydrochloride (CEPLENE) (Maxim); VX 950/LY 570310 (Vertex/Eli Lilly); ISIS 14803 (Isis); IDN-6556 (Idun Pharma.); JTK 003 (AKROS Pharma); tarvacin (Peregrine); HCV-796 (ViroPharma); CH-6 (Schering); ANA971 (ANADYS); ANA245 (ANADYS); CPG 10101 (ACTILON) (Coley); rituximab; valopicitabine; HepX™-C antibody (XTL); IC41 (Intercell); Medusa Interferon (Flamel Technologies); E-1 (Innogenetics); Multiferon (Viragen); and BILN 2061 (Boehringer-Mannheim).

In some embodiments, the antiviral agent is interferon-α, as defined herein, including a prodrug thereof.

In some embodiments, the antiviral agent is ribavirin or a prodrug thereof (e.g., viramidine).

In some embodiments, the antiviral agent is boceprevir or a prodrug thereof.

In some embodiments, the antiviral agent is telaprevir.

In some embodiments, the antiviral agent is alisporivir.

In some embodiments, the antiviral agent is NM-107 or a prodrug thereof.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo.

The term "solvate" refers to a complex of variable stoichiometry (e.g., di-, tri-, tetra-, penta-, hexa-, and so on), which is formed by a solute (the compound of present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As used herein, the term "co-administering" describes administering to the subject two agents during the treatment. This term encompasses administering the anti-viral agent prior to, concomitant with or subsequent to administering the HCQ or the salt thereof. This term also encompasses administering the two agents via the same route of administration or via different routes of administration. This term further encompasses administering the two agents within a single pharmaceutical composition or in two separate pharmaceutical compositions, each comprising a single agent, as is further detailed hereinbelow.

In some embodiments, co-administering is effected such that the efficacy window of the HCQ and the efficacy window of the antiviral agent substantially overlap.

As is well known in the art, an efficacy window of an agent depends on various factors such as systemic absorbance rate, the time required to reach a plasma peak concentration and/or clearance rate.

It is often desirable to treat subjects suffering from an HCV-related disease with two or more compounds which exhibit an antiviral effect, so as to simultaneously act on the virus via two or more antiviral mechanisms, when one compound sensitizes HCV to the second compound, and/or when the compounds act in synergy.

Simultaneous action of two or more agents can be achieved if the agents exhibit their effect within the same time frame.

As used herein, the phrase "efficacy window" describes a time frame during which an active agent exhibits a desired pharmacological effect, such as an antiviral effect, upon administration. In other words, this phrase describes that time period at which the plasma concentration of an active agent is equal to or higher than a minimal pharmacologically effective concentration thereof.

The phrase "substantially overlap" with respect to the efficacy windows of the active agents means that during a certain time period upon administration of two agents described herein (e.g., HCQ and an antiviral agent), both agents exhibit a desired pharmacological effect to some extent, namely, a plasma concentration of each agent is equal to or is higher than a minimum pharmacologically effective concentration of the agent. The efficacy windows of the active agents can overlap for, for example, 5 minutes, 10 minutes, 15 minutes, 20 minutes, 25 minutes, 30 minutes, 1 hour, 2 hours, 3 hours and even for longer time periods. The efficacy windows of the active agents can overlap such that during the overlapping period, both agents exhibit a maximal efficacy, such that one agent exhibits a maximal efficacy while the other agent exhibits a partial efficacy or such that both agents exhibit a partial efficacy.

In some embodiments, the anti-viral agent is an interferon.

In some embodiments, the antiviral agent comprises an interferon and at least one other antiviral agent described herein (e.g., an antiviral agent that does not inhibit HCV-induced autophagy). Optionally HCQ is co-administered with an interferon and ribavirin.

As used herein, the term "interferon" refers to a member of a family of highly homologous species-specific proteins that inhibit viral replication and cellular proliferation and modulate immune response. Herein, the term "interferon" encompasses derivatives of the naturally occurring proteins, including, without limitation, mutant forms of a naturally occurring interferon, and derivatives (e.g., conjugates) of a naturally occurring interferon, such as PEGylated interferon (polyethylene glycol modified conjugates of interferon) and interferon attached to another protein (e.g., as a fusion protein).

Human interferons are grouped into three classes based on their cellular origin and antigenicity: interferon-α (leukocytes), interferon-β (fibroblasts) and interferon-γ (B cells), each of which is encompassed herein by the term "interferon". Recombinant forms of each group have been developed and are commercially available. Subtypes in each group are based on antigenic/structural characteristics.

In exemplary embodiments, the interferon is an interferon-α.

As used herein, the term "interferon-α" refers to a class of interferons. At least 24 versions of interferon-α (grouped into subtypes A through H), having distinct amino acid sequences, have been identified by isolating and sequencing DNA encoding these peptides. Both naturally occurring and recombinant interferon-α, including consensus interferon, may be used in the practice of the invention. Suitable interferon-α for the present of embodiments of the invention described herein includes, but is not limited to, recombinant interferon alfa-2b such as INTRON®-A interferon and VIRAFERON®; recombinant interferon alfa-2a such as ROFERON® interferon; recombinant interferon alfa-2c such as BEROFOR® alfa 2 interferon; interferon alfa-n1, a purified blend of natural alfa interferons such as SUMIFERON® or WELLFERON® interferon alfa-n1 (INS); or a consensus alfa interferon such as those described in U.S. Pat. Nos. 4,897,471 and 4,695,623; or interferon alfa-n3, a mixture of natural alfa interferons such as ALFERON®. In some embodiments, the interferon-α is selected from the group consisting of interferon alfa-2a and interferon alfa 2b. The manufacture of interferon alfa 2b is described in U.S. Pat. No. 4,530,901.

The term "interferon-α" is further intended to include interferon derivatives such as PEGylated analogs of interferon-α, optionally interferon alfa-2a and -2b. PEGylated interferon-α that may be used in embodiments of the present invention are, e.g., PEGylated interferon alfa-2a, PEGylated interferon alfa-2b, PEGylated consensus interferon and PEGylated purified interferon alfa product. PEGylated interferon alfa-2a is described, e.g., in European Patent No. EP 0593868 and commercially-available, e.g., under the tradename PEGASYS® (Hoffmann-La Roche). PEGylated interferon alfa-2b is described, e.g., in U.S. Pat. No. 5,908,621 and WO 98/48840 and commercially-available, e.g., under the tradename PEGINTRON® A (Schering Plough). PEGylated consensus interferon is described in WO 96/11953. The term "interferon-α" further encompasses other interferon-α conjugates that can be prepared by coupling an interferon-α to a water-soluble polymer. A non-limiting list of such polymers includes other polyalkylene oxide homopolymers such as polyethylene glycol (PEG), polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon-α-polymer conjugates are described in U.S. Pat. No. 4,766,106, U.S. Pat. No. 4,917,888, European Patent Application No. 0236987, European Patent Application Nos. 0510356, 0593868 and 0809996 (PEGylated interferon alfa-2a) and International Publication No. WO 95/13090.

The term "interferon-α" further includes fusion proteins of an interferon-α, for example fusion proteins of interferon-α-2a, interferon-α-2b, consensus interferon or purified interferon-α product, each of which is fused with another protein. Certain preferred fusion proteins comprise an interferon (e.g., interferon-α-2b) and an albumin as described in U.S. Pat. No. 6,972,322 and international patent application publications WO2005/003296 and WO2005/077042. An optional interferon conjugated to a human albumin is ALBUFERON® which is a longer-acting form of interferon-α created using albumin fusion technology. ALBUFERON® results from the genetic fusion of human albumin and interferon-α. Also included are consensus interferons, such as INFERGEN®.

In exemplary embodiments, the interferon is PEGylated interferon α-2a.

As demonstrated in the Examples section that follows, it has been shown the HCQ and an interferon-α can act in synergy.

By "synergy" it is meant that the effect of the compounds when administered in combination is greater than an additive effect of the compounds when administered alone as a single agent.

As exemplified in the Examples below, synergy can be determined according to methods described, for example, by Prichard & Shipman [*Antiviral Res* 1990, 14:181-205], wherein the theoretical additive effect is calculated from dose-response curves of individual compounds by the equation $Z=X+Y(1-X)$, where X and Y represent the inhibition produced by the individual compounds and Z represents the effect produced by the combination of compounds. An effect of a combination of compounds which is higher than Z (optionally 20% higher, and optionally 30% higher) indicates synergism.

As further exemplified in the Examples below, synergy can be determined according to methods described by Chou & Talalay [*Trends Pharmacol Sci* 1983, 4:450-454; *Adv Enzyme Regul* 1984, 22:27] and/or using an isobologram, e.g., as described by Tallarida [*J Pharmacol Exp Therap* 2001, 298: 865-872].

In some embodiments, a synergistic effect is determined according to the abovementioned method of Prichard & Shipman. In exemplary some embodiments, a synergistic effect is determined according to each of the abovementioned methods.

Accordingly, in some embodiments, the method as described herein is effected by co-administering to the subject, as defined herein, an amount of HCQ as defined herein and a therapeutically effective amount of an interferon as defined herein.

In some embodiments, the therapeutically effective amount of the interferon (e.g., PEGylated interferon) ranges from 50 to 250 µg (optionally per week).

In some embodiments, the therapeutically effective amount of interferon is in a range of from 3,000-1,000,000 units, optionally, from 10,000-1,000,000 units, per administration (optionally per week).

The frequency of interferon administration may depend, at least in part, on the half-life of the interferon in a body. PEGylated interferons typically have a longer half-life, and are therefore administered less frequently than other interferons.

In some embodiments, an interferon (e.g., a non-PEGylated interferon) is administered from 2-4 times per week, optionally 3 times per week.

In some embodiments, a PEGylated interferon is administered once per week.

In some embodiments, the method is effected by co-administering to the subject an amount of HCQ as described herein and a therapeutically effective amount of ribavirin (or a prodrug thereof).

In some embodiments, the method is effected by co-administering to the subject an amount of HCQ as described herein and a therapeutically effective amount of boceprevir.

In some embodiments, the method is effected by co-administering to the subject an amount of HCQ as described herein and a therapeutically effective amount of telaprevir.

A current standard treatment of HCV-related diseases comprises co-administration of ribavirin with an interferon-$\alpha$ (e.g., a PEGylated interferon-$\alpha$).

Hence, in some embodiments, the method is effected by co-administering to the subject an amount of HCQ as described herein and a therapeutically effective amount of ribavirin and a therapeutically effective amount of an interferon-$\alpha$ (e.g., a PEGylated interferon-$\alpha$).

In some embodiments, the method is effected by co-administering to the subject an amount of HCQ as described herein and a therapeutically effective amount of ribavirin and a therapeutically effective amount of boceprevir.

In some embodiments, the method is effected by co-administering to the subject an amount of HCQ as described herein and a therapeutically effective amount of ribavirin and a therapeutically effective amount of telaprevir.

In some embodiments, the method is effected by co-administering to the subject an amount of HCQ as described herein and a therapeutically effective amount of ribavirin, a therapeutically effective amount of an interferon-$\alpha$, and a therapeutically effective amount of boceprevir.

In some embodiments, the method is effected by co-administering to the subject an amount of HCQ as described herein and a therapeutically effective amount of ribavirin, a therapeutically effective amount of an interferon-$\alpha$, and a therapeutically effective amount of telaprevir.

In some embodiments, the method is effected by co-administering to the subject an amount of HCQ as described herein and a therapeutically effective amount of ribavirin, a therapeutically effective amount of an interferon-$\alpha$, and a therapeutically effective amount of an NS5B inhibitor.

In some embodiments, the method is effected by co-administering to the subject an amount of HCQ as described herein and a therapeutically effective amount of ribavirin, a therapeutically effective amount of an interferon-$\alpha$, and a therapeutically effective amount of a cyclophilin inhibitor (e.g., a cyclophilin inhibitor described herein).

In some embodiments, the method is effected by co-administering to the subject an amount of HCQ as described herein and a therapeutically effective amount of ribavirin, a therapeutically effective amount of an interferon-$\alpha$, and a therapeutically effective amount of an NS5A inhibitor.

As described herein, it is often desirable to treat subjects suffering from an HCV-related disease with two or more compounds which exhibit complementary effects.

Hence, in some embodiments, HCQ, which inhibits HCV-induced autophagy, is co-administered with an antiviral agent which acts against HCV by a different mechanism, e.g., wherein the antiviral agent does not inhibit HCV-induced autophagy.

Examples of suitable anti-viral agent which do not inhibit HCV-induced autophagy include, without limitation, polymerase inhibitors (e.g., NM-107, valopicitabine), ribavirin, viramidine, boceprevir, telaprevir, and alisporivir. Ribavirin is an exemplary antiviral agent. In some embodiments, a prodrug of ribavirin (e.g., viramidine) is used.

Without being bound by any particular theory, it is believed that the inhibition of autophagy by HCQ disrupts the life cycle of HCV to an extent which renders the HCV considerably more susceptible to a second antiviral effect (e.g., an antiviral effect of a antiviral agent co-administered with HCQ), such that the HCQ may sensitize HCV to the antiviral agent, for example, HCV which is partially or fully resistant to the antiviral agent.

Further according to an aspect of some embodiments of the present invention there is provided hydroxychloroquine which is identified for use in the treatment of a hepatitis C virus (HCV) related disease in an amount sufficient to inhibit HCV-induced autophagy, as defined herein.

According to embodiments of this aspect of the present invention the HCQ is for use in the treatment of an HCV-related disease, as described herein, wherein the treatment is effected by administering to a subject in need thereof, as described herein, an amount of HCQ sufficient to inhibit HCV-induced autophagy, as defined herein.

Further according to an aspect of some embodiments of the present invention there is provided a use of a hydroxychloroquine in the manufacture of a medicament for use in the treatment of a hepatitis C virus (HCV) related disease. In some embodiments, the medicament is identified for use in treating HCV related disease by administering to a subject in need thereof hydroxychloroquine in an amount sufficient to inhibit HCV-induced autophagy, as defined herein.

In some embodiments of this aspect of the present invention, the medicament comprises a therapeutically effective amount of HCQ or a salt thereof, or, the medicament comprises instructions to administer to the subject an amount of HCQ, as indicated herein.

The amount of HCQ sufficient to inhibit HCV-induced autophagy is optionally any amount or range of amounts described elsewhere herein (e.g., from 400 to 2000 mg per day).

HCV-induced autophagy is optionally characterized as described elsewhere herein, and optionally by an increase in a level of protein selected from the group consisting of ULK1, AMBRA1, ATG2A, GABARAPL1, FOX03, SQSTM1, PIK3C3 and MAP1LC3B (e.g., as described herein).

In some embodiments, the disease is caused by an antiviral-resistant HCV (e.g., as described elsewhere herein), and optionally by genotype 1 HCV and/or genotype 4 HCV.

The abovementioned treatment may be effected in accordance with any of the methods described herein, and optionally further comprises co-administering a therapeutically effective amount of an antiviral agent (e.g., any individual antiviral agent or combination of antiviral agents described herein for co-administration with HCQ).

As discussed herein, it is believed that the inhibition of autophagy by HCQ disrupts the life cycle of HCV to an extent which renders the HCV considerably more susceptible to a different antiviral effect (e.g., an antiviral effect which does not involve inhibition of autophagy), such that the HCQ may sensitize HCV to a antiviral agent, particularly an antiviral agent which does not inhibit HCV-induced autophagy.

Hence, according to an aspect of some embodiments of the present invention there is provided a method of treating an hepatitis C virus (HCV) related disease, such as an HCV infection, as defined herein, in a subject in need thereof, which is effected by co-administering to the subject a therapeutically effective amount of hydroxychloroquine or a pharmaceutically acceptable salt thereof and a therapeutically effective amount of an antiviral agent, wherein the anti-viral agent does not inhibit HCV-induced autophagy, thereby treating the HCV infection.

In some embodiments, the therapeutically effective amount of hydroxychloroquine is sufficient to inhibit HCV-induced autophagy in the subject. Suitable amounts according to some embodiments of the invention are described elsewhere herein.

Examples of suitable anti-viral agent which do not inhibit HCV-induced autophagy include, without limitation, ribavirin, viramidine, boceprevir, telaprevir, and alisporivir. Ribavirin is an exemplary antiviral agent. In some embodiments, a prodrug of ribavirin (e.g., viramidine) is used.

In some embodiments, the method further comprises co-administering to the subject a therapeutically effective amount of an additional antiviral agent, such that at least 3 compounds are co-administered: HCQ and at least two antiviral agents, namely, the above-described anti-viral agent which does not inhibit HCV-induced autophagy, and the aforementioned additional antiviral agent.

The additional antiviral agent may be, for example, any antiviral agent described herein (with the proviso that it is not identical to the aforementioned anti-viral agent which does not inhibit HCV-induced autophagy), and it may or may not be capable of inhibiting HCV-induced autophagy. Thus, for example, the additional antiviral agent may be anyone of an interferon, a viral protease inhibitor, an NS4A inhibitor, an NS5A inhibitor, a viral polymerase inhibitor, a cyclophilin inhibitor, a helicase inhibitor, a glycosylation inhibitor, and an antiphospholipid antibody (e.g., as described elsewhere herein).

Co-administration of particular combinations of HCQ and two antiviral agents, wherein at least one antiviral agent does not inhibit HCV-induced autophagy, are described elsewhere herein, and are suitable for use according to some embodiments of this aspect of the invention.

In some embodiments, the additional antiviral agent is an interferon (e.g., an interferon described herein). Optionally, the interferon is an interferon-α, and optionally a PEGylated interferon-α (e.g., an interferon-α described herein).

In some embodiments, the aforementioned interferon is co-administered with ribavirin, such that the method comprises co-administering HCQ, the interferon and ribavirin. The therapeutically effective amount of ribavirin is optionally in a range of from 50 to 1200 mg per day (optionally from 50 to 150 mg per day; and optionally from 400 to 1200 mg per day).

Further according to an aspect of some embodiments of the present invention there is provided hydroxychloroquine which is identified for use in the treatment of a hepatitis C virus (HCV) related disease, as defined herein, in combination with an antiviral agent that does not inhibit HCV-induced autophagy, as defined herein.

According to embodiments of this aspect of the present invention the HCQ is for use in the treatment of an HCV-related disease, as described herein, wherein the treatment is effected by administering to a subject in need thereof, as described herein, HCQ in combination with an antiviral agent that does not inhibit HCV-induced autophagy, as defined herein.

The treatment can be effected by co-administering the two agents separately or co-formulated in a single pharmaceutical composition, as is further detailed hereinafter.

Further according to an aspect of some embodiments of the present invention there is provided a use of a hydroxychloroquine in the manufacture of a medicament for use in the treatment of a hepatitis C virus (HCV) related disease. In some embodiments, the medicament is identified for use in treating HCV related disease by administering to a subject in need thereof hydroxychloroquine in combination with an antiviral agent that does not inhibit HCV-induced autophagy, as defined herein.

In some embodiments of this aspect of the present invention, the medicament comprises a therapeutically effective amount of HCQ or a salt thereof, or, the medicament comprises instructions to administer to the subject an amount of HCQ, as indicated herein.

In some embodiments, the medicament further comprises a therapeutically effective amount of an antiviral agent that does not inhibit HCV-induced autophagy, or, the medicament comprises instructions to co-administer to the subject an amount of an antiviral agent that does not inhibit HCV-induced autophagy, as indicated herein.

In some embodiments, the medicament comprises HCQ and an anti-viral agent as described herein which are co-formulated in a single pharmaceutical composition, as is further detailed hereinbelow.

The therapeutically effective amount of HCQ according to some embodiments of this aspect of the invention is an amount of HCQ or range of amounts of HCQ described elsewhere herein (e.g., from 400 to 2000 mg per day).

In some embodiments of any of the aspects of the invention described herein which relate to co-administration of HCQ with one or more antiviral agents, the disease to be treated is caused by an antiviral-resistant HCV, and optionally by an HCV genotype that is resistant to an antiviral agent co-administered with the HCQ (e.g., an antiviral agent which does not inhibit HCV-induced autophagy, as defined herein). In some embodiments, the disease is caused by genotype 1 HCV and/or genotype 4 HCV.

The abovementioned treatment may be effected in accordance with any of the methods described herein, and optionally further comprises co-administering a therapeutically effective amount of an antiviral agent (e.g., any individual antiviral agent or combination of antiviral agents described herein for co-administration with HCQ).

As discussed hereinabove, HCQ exhibits effects (e.g., inhibition of HCV-induced autophagy) which can enhance the efficacy of an antiviral agent, including, for example, sensitizing an HCV towards an anti-viral agent to which the HCV is resistant in the absence of HCQ.

Hence, according to an aspect of some embodiments of the present invention there is provided a method of treating an hepatitis C virus (HCV) related disease in a subject in need thereof, wherein the disease is caused by an HCV genotype resistant to an antiviral agent. The method, according to this aspect of embodiments of the invention, is effected by co-administering to the subject a therapeutically effective amount of hydroxychloroquine or a pharmaceutically acceptable salt thereof and a therapeutically effective amount of the antiviral agent, to which the HCV genotype is resistant.

Herein, the phrase "HCV genotype resistant to an antiviral agent" and "hepatitis C virus (HCV) genotype resistant to an antiviral agent" refer to an HCV genotype in an infected subject which was determined to be resistant to a given antiviral agent by: a) prior treatment of the subject with the antiviral agent, wherein the subject was non-responsive to the treatment; and/or b) identification of the genotype of the HCV, wherein the genotype is identified as one wherein most (>50%) subjects infected with such an HCV genotype are non-responsive to treatment with the antiviral agent. The phrase "resistant to an antiviral agent" does not include resistance which can be overcome by simply raising a dosage of the antiviral agent to a higher dosage which is still tolerated by the subject.

In some embodiments, the disease is caused by genotype 1 HCV and/or genotype 4 HCV.

In some embodiments, subjects treatable by the method as described herein are subjects afflicted by HCV, which were identified as afflicted by a resistant genotype of HCV, and/or subjects afflicted by HCV which received one or more cycles of antiviral therapy but were found non-responsive to this therapy in terms of no or incomplete eradication of the viral infection and/or in terms of insufficient relief of symptoms associated with the viral infection.

The therapeutically effective amount of the antiviral agent which is co-administered according to this aspect of embodiments of the invention may optionally be an amount which is effective for treating a non-resistant HCV genotype. Alternatively or additionally, the therapeutically effective amount is an amount which exerts a desired therapeutic effect when co-administered with HCQ. Optionally, the therapeutically effective amount is selected to be tolerated by the subject.

It is to be appreciated that embodiments according to this aspect of the invention involve sensitization of an HCV genotype to an antiviral agent, such that the antiviral agent exerts a clinically significant antiviral effect on the HCV when co-administered with HCQ as described herein, whereas such an antiviral effect would not be exerted when administered without HCQ.

The therapeutically effective amount of HCQ can be regarded as a sensitizing effective amount.

Herein, "sensitizing effective amount" refers to an amount of HCQ which causes an HCV genotype resistant to an antiviral agent (as defined herein) to be susceptible (i.e., no longer resistant) to a co-administered amount of the antiviral agent.

In some embodiments, the therapeutically effective amount of hydroxychloroquine is sufficient to inhibit HCV-induced autophagy (as defined herein) in the subject, as described elsewhere herein.

Suitable therapeutically effective amounts according to some embodiments of the invention are described elsewhere herein.

In some embodiments, the antiviral agent does not inhibit HCV-induced autophagy. Suitable examples of such antiviral agents are described elsewhere herein.

In some embodiments, the antiviral agent is ribavirin. In some embodiments, the antiviral agent is a prodrug of ribavirin (e.g., viramidine).

In some embodiments, the method further comprises co-administering to the subject a therapeutically effective amount of an additional antiviral agent, such that at least 3 compounds are co-administered: HCQ and at least two antiviral agents, namely, the above-described anti-viral agent which does not inhibit HCV-induced autophagy, and the aforementioned additional antiviral agent, as described in more detail elsewhere herein.

Further according to an aspect of some embodiments of the present invention there is provided hydroxychloroquine which is identified for use in combination with an antiviral agent in the treatment of a hepatitis C virus (HCV) related disease caused by an HCV genotype resistant to the antiviral agent (as defined herein).

According to embodiments of this aspect of the present invention the HCQ is for use in the treatment of an HCV-related disease, as described herein, wherein the treatment is effected by administering to a subject in need thereof, as described herein, HCQ in combination with an antiviral agent, wherein the disease is caused by an HCV genotype resistant to the antiviral agent, as defined herein.

Further according to an aspect of some embodiments of the present invention there is provided a use of a hydroxychloroquine in the manufacture of a medicament for use in the treatment of a hepatitis C virus (HCV) related disease caused by an HCV genotype resistant to an antiviral agent, as defined herein. In some embodiments, the medicament is identified for use in treating an HCV related disease by administering to a subject in need thereof hydroxychloroquine in combination with the aforementioned antiviral agent.

The antiviral agent may optionally be any antiviral agent described herein, including combinations of antiviral agents described herein. In some embodiments, the antiviral agent is an interferon-$\alpha$ and/or ribavirin, such that the HCV genotype is resistant to interferon-$\alpha$ and/or ribavirin.

In some embodiments of this aspect of the present invention, the medicament comprises a therapeutically effective amount (e.g., a sensitizing effective amount, as defined herein) of HCQ or a salt thereof, or, the medicament comprises instructions to administer to the subject a therapeutically effective amount of HCQ, as indicated herein.

In some embodiments, the abovementioned treatment comprises administration of HCQ in an amount sufficient to inhibit HCV-induced autophagy, as described elsewhere herein.

The abovementioned treatment may be effected in accordance with methods described herein.

The therapeutically effective amount of HCQ according to some embodiments of this aspect of the invention is an amount of HCQ or range of amounts of HCQ described elsewhere herein (e.g., from 400 to 2000 mg per day).

Optionally, the antiviral agent is an antiviral agent that does not inhibit HCV-induced autophagy (e.g., ribavirin), as described elsewhere herein.

In some embodiments, the disease is caused by genotype I HCV and/or genotype 4 HCV.

As exemplified in the Examples section below, HCQ exhibits a synergistic antiviral effect when in combination with another antiviral agent, and such synergistic effects are surprisingly not exhibited by the structurally similar chloroquine. Such a synergistic effect enhances the therapeutic potential of both HCQ and the antiviral agent, and thereby allows for more effective antiviral treatment for any given drug dosage and/or treatment at lower dosages which results in better tolerance and fewer adverse effects.

Hence, according to another aspect of embodiments of the present invention, there is provided method of treating a hepatitis C virus (HCV) related disease in a subject in need thereof, the method comprising co-administering to the subject a therapeutically effective amount of hydroxychloroquine or a pharmaceutically acceptable salt thereof in combination with a therapeutically effective amount of an antiviral agent, wherein the therapeutically effective amount of hydroxychloroquine and the therapeutically effective amount of the antiviral agent are selected such that hydroxychloroquine and the anti-viral agent act in synergy, as defined herein.

Combinations which act in synergy are also referred to herein as synergistic combinations.

Therapeutically effective amounts which result in synergy may be selected by determining the effects of different combinations of HCQ and the antiviral agent (optionally including the effects of HCQ alone and/or the antiviral agent alone), as exemplified in the Examples section.

In some embodiments, synergy is effected using an amount of HCQ which is at least 400 mg per day (e.g., in a range of from 400 to 2000 mg per day), preferably at least 500 mg per day (e.g., from 500 to 1000 mg per day), optionally at least 600 mg per day, and optionally at least 800 mg per day (e.g., 800-1000 mg/day, 850-950 mg/day, 900 mg/day). Suitable ranges of at least 600 mg per day and at least 800 mg per day are described elsewhere herein.

The antiviral agent exhibiting synergy in combination with HCQ is optionally any antiviral agent or combination of antiviral agents described herein.

In some embodiments, the antiviral agent exhibiting synergy in combination with HCQ is a viral protease inhibitor (e.g., a protease inhibitor described herein).

In some embodiments, the antiviral agent exhibiting synergy in combination with HCQ is a viral polymerase inhibitor (e.g., a polymerase inhibitor described herein).

In some embodiments, the antiviral agent exhibiting synergy in combination with HCQ is an interferon. In exemplary embodiments, the interferon is an interferon-α (e.g., PEGylated interferon-α).

In some embodiments, the therapeutically effective amount of an interferon is in a range of from 50 to 250 μg per administration (optionally per week), as described elsewhere herein.

According to some embodiments, the method comprises co-administering from 400 to 2000 mg per day of HCQ (or a pharmaceutically acceptable salt thereof) in combination with from 50 to 250 μg of an interferon (e.g., as described herein).

In some embodiments, the therapeutically effective amount of hydroxychloroquine, in addition to exhibiting synergy, is sufficient to inhibit HCV-induced autophagy as described herein.

Optionally, the method further comprises co-administration of a therapeutically effective amount of an additional antiviral agent (e.g., an antiviral agent described herein), which may or may not exhibit synergy, such that at least 3 compounds are co-administered: HCQ, and at least two antiviral agents, at least one of which exhibits synergy in combination with HCQ, as described herein. Optionally, the additional antiviral agent is ribavirin (or a prodrug thereof).

Further according to an aspect of some embodiments of the present invention there is provided hydroxychloroquine which is identified for use in combination with an antiviral agent in the treatment of a hepatitis C virus (HCV) related disease, wherein the HCQ and the antiviral agent act in synergy (as defined herein) in treating the disease (e.g., when co-administered as described herein).

According to embodiments of this aspect of the present invention the HCQ is for use in the treatment of an HCV-related disease, as described herein, wherein the treatment is effected by administering to a subject in need thereof, as described herein, HCQ in combination with an antiviral agent, wherein the HCQ and the antiviral agent act in synergy in treating the disease, as described herein.

According to these embodiments, the treatment comprises a synergistic combination of HCQ and the anti-viral agent, as defined herein.

Further according to an aspect of some embodiments of the present invention there is provided a use of a hydroxychloroquine in the manufacture of a medicament for use in the treatment of a hepatitis C virus (HCV) related disease. In some embodiments, the medicament is identified for use in treating an HCV related disease by administering to a subject in need thereof hydroxychloroquine in combination with an antiviral agent that acts in synergy with HCQ (e.g., as described herein).

According to these embodiments, the treatment comprises a synergistic combination of HCQ and the anti-viral agent, as defined herein.

Suitable antiviral agents and dosages (of HCQ and the antiviral agent) for effecting synergy are described herein.

A therapeutically effective amount of an additional antiviral agent may optionally be co-administered with the HCQ and with the antiviral agent which acts in synergy with HCQ, as described elsewhere herein.

The methods and treatments described herein according to various aspects of the invention may comprise a step wherein one single pharmaceutical composition comprising hydroxychloroquine, or a pharmaceutically acceptable salt thereof, an antiviral agent, and optionally at least one pharmaceutically acceptable carrier, diluent, excipients and/or additive is administered. Alternatively, the methods of the invention may comprise a step wherein distinct compositions comprising at least one of the active ingredients cited above together with one or more acceptable carriers thereof are administered substantially simultaneously or sequentially.

The combination of the invention may be preferably administered orally. The active combined drug compounds employed in the instant therapy can be administered in various oral forms including, but not limited to, tablets, capsules, pills, powders, granules, elixirs, tinctures, suspensions, syrups, and emulsions. It is contemplated that the active drug compounds can be delivered by any pharmaceutically acceptable route and in any pharmaceutically acceptable dosage form. These include, but are not limited to the use of oral conventional rapid-release, time controlled-release, and delayed-release pharmaceutical dosage forms. The active drug components can be administered in a mixture with suitable pharmaceutical diluents, excipients or carriers (collectively referred to herein as "carrier" materials suitably selected to with respect to the intended form of administration. As indicated, it is contemplated that oral administration can be effectively employed. Thus, tablets, capsules, syrups, and the like as well as other modalities consistent with conventional pharmaceutical practices can be employed.

According to another embodiment, the active ingredients used by the invention or composition comprising a combination thereof, may be administered via any mode of administration. For example, oral, intravenous, intramuscular, subcutaneous, intraperitoneal, parenteral, transdermal, intravaginal, intranasal, mucosal, sublingual, topical, rectal or subcutaneous administration, or any combination thereof.

In instances in which oral administration is in the form of a tablet or capsule, the active drug components can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

Alternatively, the combination of this invention may also be administered in controlled release formulations such as a slow release or a fast release formulation. Such controlled release formulations of the combination of this invention may be prepared using methods well known to those skilled in the art. The method of administration will be determined by the attendant physician or other person skilled in the art after an evaluation of the subject's conditions and requirements.

The combined compounds of the present invention are generally administered in the form of a pharmaceutical composition comprising both compounds of this invention together with a pharmaceutically acceptable carrier or diluent. Thus, the compounds used by this invention can be administered either individually in a kit or together in any conventional oral, parenteral or transdermal dosage form.

More particularly, since the present invention relates to the treatment of diseases and conditions with a combination of active ingredients which may be administered separately, the invention also relates as a further aspect, to combining separate pharmaceutical compositions in kit form. The kit includes two separate pharmaceutical compositions: hydroxychloroquine, or a pharmaceutically acceptable salt thereof, and an interferon alfa. The kit includes container means for containing both separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The kit may be for effecting any of the methods of treatment described herein, optionally with instructions describing how to effect the method.

It should be appreciated that both components of the kit, the hydroxychloroquine in the first dosage form and the antiviral agent in the second dosage form may be administered simultaneously.

Alternatively, said first compound or dosage form and said second compound or dosage form are administered sequentially in either order.

In any of the methods and used described hereinabove, administration of HCQ and optionally another one or more antiviral agent(s) is effected for a time period that optionally ranges from 1 month to life, optionally from 24 weeks to life, and optionally from 24 weeks to 1 year, depending on the HCV-related disease to be treated.

Generally, administration is effected as long as virus is found in the subject and/or until at least one of the symptoms associated with the disease are alleviated.

In embodiments where the HCV-related is chronic, treatment is effected for at least 24 weeks, as described herein.

According to further aspects of some embodiments of the present invention there are provided pharmaceutical kits.

In some embodiments, there is provided a kit comprising HCQ and anti-viral agent, each being individually packaged within the kit, wherein the kit comprises instructions to use HCQ in an amount sufficient to inhibit HCV-induced autophagy, as defined herein.

In any of the methods, uses and kits described herein, the HCQ or a salt thereof and the anti-viral agent, if utilized, can be utilized either per se or can form a part of a pharmaceutical composition which further comprises a pharmaceutically acceptable carrier, as defined herein.

In any of the methods and uses described herein, whenever HCQ or a salt thereof is used in combination, or is co-administered, with an anti-viral agent, the HCQ and the anti-viral agent can be formulated into a single pharmaceutical composition.

According to further aspects of embodiments of the present invention there is provided a pharmaceutical composition comprising HCQ (or a pharmaceutically acceptable salt thereof, such as HCQ sulfate) and an anti-viral agent (e.g., an antiviral agent described herein as being useful when co-administered with HCQ), and a pharmaceutically acceptable carrier. In some embodiments, the anti-viral agent is ribavirin.

In some embodiments, the composition comprises more than one antiviral agent. Such compositions may be formulated so as to be suitable for effecting a method of treatment described herein which comprises co-administration of HCQ and at least two antiviral agents.

In some embodiments, the composition is formulated so as to combine the autophagy-inhibiting properties of HCQ with an antiviral agent which acts via a different mechanism, as discussed in more detail elsewhere herein. Thus, the antiviral agent in the composition is an antiviral agent that does not inhibit HCV-induced autophagy (e.g., as described herein). Optionally, the composition is identified for use (e.g., in or on a packaging material) for use in treating an HCV-related disease. In some embodiments, the composition is identified for use in the treatment of an HCV-related infection in an HCV-infected subject non-responsive to an anti-HCV therapy (e.g., as defined herein).

In some embodiments, the composition is formulated for treating an HCV-related disease caused by an HCV genotype resistant to an antiviral agent (e.g., by sensitizing HCV to the antiviral agent), as discussed in more detail elsewhere herein. Thus, the antiviral agent in the composition is an antiviral agent to which an HCV genotype is resistant (e.g., as described herein). Optionally, the composition is identified for use (e.g., in or on a packaging material) for use in treating an HCV-related disease caused by an HCV genotype resistant to an antiviral agent (e.g., as described herein).

In some embodiments, the composition is formulated so as to provide a synergistic effect between the HCQ and the antiviral agent, as discussed in more detail elsewhere herein. Thus, the antiviral agent in the composition is an antiviral agent which acts in synergy with HCQ (e.g., as described herein). Optionally, the composition is identified for use (e.g., in or on a packaging material) for use in treating an HCV-related disease.

The composition is preferably formulated for administration by a route suitable for both the HCQ and the antiviral agent.

As discussed herein, HCQ is suitable for oral administration. Furthermore, oral administration is a relatively convenient route of administration.

Hence, in some embodiments, the composition is formulated for oral administration. The antiviral agent is preferably selected so as to be suitable for oral administration.

For a given antiviral agent, suitable routes of administration will typically be known in the art. For example, ribavirin is known to be suitable for oral administration, whereas interferon is not considered suitable for oral administration.

In some embodiments, the antiviral agent is a small molecule (e.g., in contrast to interferon). Optionally, the small molecule is characterized by a molecular weight of less than 1,500 Da, optionally less than 1,000 Da, optionally less than 8,000 Da, optionally less than 600 Da, and optionally less than 400 Da. In general, small molecules are considerably more suitable for oral administration than larger molecules (e.g., polymers).

In some embodiments, the composition is identified for use with an additional antiviral agent. Optionally, co-administration of the composition and an additional antiviral agent is for effecting a method of treatment comprising co-administration of HCQ and at least two antiviral agents (e.g., as described herein).

In some embodiments, the additional antiviral agent is unsuitable for inclusion in the composition, and as therefore administered separately. The additional antiviral agent may optionally be unsuitable for the route of administration of the composition, for example, wherein the composition is formulated for oral administration, and the additional antiviral agent is unsuitable for oral administration (e.g., an interferon). Alternatively or additionally, additional antiviral agent may optionally be unsuitable for the frequency of administration of the composition, for example, wherein the composition is formulated for administration once per day, and the additional antiviral agent is more suitable for administration once per week (e.g., a PEGylated interferon-$\alpha$).

The composition may be, for example, in the form of a liquid, a semi-solid (e.g., gel), or solid.

In some embodiments, the composition is in a solid form. Examples of solid forms for a composition include, without limitation, a tablet, a capsule (e.g., comprising an encapsulated solid), a caplet, a powder, microspheroids, and granules.

The composition is preferably formulated in accordance with the intended frequency of administration of the composition. This, in turn, will depend on the properties of the active agents. As discussed herein, HCQ may be administered, for example, once per day, but also at other frequencies (e.g., twice or thrice a day). Thus, the intended frequency of administration will depend on the properties of the antiviral agent co-formulated with the HCQ.

Thus, for example, in embodiments wherein the antiviral agent is suitable for administration once per day, the composition is optionally formulated for administration once per day, in embodiments wherein the antiviral agent is suitable for administration twice per day, the composition is optionally formulated for administration twice per day, and so forth.

In some embodiments, the antiviral agent may be administered effectively at various frequencies (e.g., once per day, twice per day, and thrice per day). Typically, when other factors are equal, it will be more convenient for a subject to be administered a composition once per day than twice per day, more convenient to be administered a composition twice per day than more than twice per day, and more convenient to be administered a composition a constant number of times per day than different numbers of times on different days.

For any given antiviral agent, optimal (e.g., most therapeutically effective and/or most convenient) frequencies of administration of the agent will typically be known to those skilled in the art.

It is to be appreciated that an active agent can be made more suitable for less frequent administration (e.g., once per day, as is particularly convenient, instead of twice or more per day) by formulating a composition appropriately, for example, by formulating the composition for slow release of the active agents therein.

Slow release preparations typically include slow release biodegradable carriers. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/dissolve in body fluids and release the active compound(s) therein. The particles are preferably nanoparticles (i.e., in the nanometer range, e.g., in the range of about 1 to about 500 nm in diameter, preferably about 50-200 nm in diameter, most preferably about 100 nm in diameter).

The rate at which a drug is released is generally dependent on the rate at which the dosage form disintegrates or dissolves. Disintegration greatly increases the drug's surface area in contact with GI fluids, thereby promoting drug dissolution and absorption. Disintegrants and other excipients (e.g., diluents, lubricants, surfactants, binders, dispersants) are often added during manufacture to facilitate these processes. Surfactants increase the dissolution rate by increasing the wettability, solubility, and dispersibility of the drug. Disintegration of solid forms may be retarded by excessive pressure applied during the tableting procedure or by special coatings applied to protect the tablet from the digestive processes of the gut. Hydrophobic lubricants (e.g., magnesium stearate) may bind to the active drug and reduce its bioavailability.

Dissolution rate determines the availability of the drug for absorption. When slower than absorption, dissolution becomes the rate-limiting step. Overall absorption can be controlled by manipulating the formulation. For example, reducing the particle size increases the drug's surface area, thus increasing the rate and extent of GI absorption of a drug whose absorption is normally limited by slow dissolution. Dissolution rate is affected by whether the drug is in salt, crystal, or hydrate form.

Oral slow-release forms are often designed to maintain therapeutic drug concentrations for greater than 12 hours. The absorption rate can be controlled by coating drug particles with wax or other water-insoluble material, by embedding the drug in a matrix from which it is released slowly during transit through the GI tract, or by complexing the drug with ion-exchange resins.

Thus, for example, a slow-release formulation in tablet form, may be based on the use of a hydrophilic polymer which swells in contact with gastrointestinal fluids, to form a gel, which creates a barrier that enrobes the tablet. The barrier limits physical exchanges between the inside of the tablet and the surrounding medium. As a consequence, intrusion of water towards the tablet matrix and diffusion of drug are slowed down, allowing a controlled slow release of the drug.

Various types of polymers may be used as a matrix for the slow-release of drugs, such as polyvinyl chloride, polyethylene polyamides, ethylcellulose, silicone, poly (hydroxyethyl methacrylate), other acrylic co-polymers, and polyvinylacetate-polyvinyl chloride copolymers.

In some embodiments, the composition is a unit dosage form (e.g., a unit dosage form formulated for oral administration).

The term "unit dosage form"; as used herein, describes physically discrete units (e.g., in solid form), each unit containing a predetermined quantity of HCQ and antiviral agent calculated to produce the desired therapeutic effect, in association with at least one pharmaceutically acceptable carrier, diluent, excipient, or combination thereof (e.g., as described herein).

The amount of HCQ and the antiviral agent in the composition are optionally adjusted so as to provide an appropriate amount of each active agent per day (e.g., as described elsewhere herein). Optionally, the amount of HCQ is sufficient to inhibit HCV-induced autophagy (e.g., as described elsewhere herein) and/or sufficient to sensitize HCV (e.g., as described elsewhere herein) to the antiviral agent included in the composition.

Optionally, each unit dosage form comprising a therapeutically effective amount of HCQ, as described hereinabove, suitable for 1 day (e.g., from 400 to 2000 mg, from 500 to 1000 mg, etc.). Optionally, such a pharmaceutical composition is further identified for administration once per day.

Alternatively, each unit dosage form comprises one half of a therapeutically effective amount of HCQ, as described hereinabove, suitable for 1 day (e.g., from 200 to 1000 mg, from 250 to 500 mg, etc.). Optionally, such a pharmaceutical composition is further identified for administration twice per day.

The unit dosage forms described herein may be provided together in a kit which comprises discrete unit dosage forms described herein, packaged together in a packaging material.

Techniques for formulation and administration of drugs may be found in "Remington's Pharmaceutical Sciences" Mack Publishing Co., Easton, Pa., latest edition, which is incorporated herein by reference.

Pharmaceutical compositions of embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the present invention thus may be formulated in conventional manner using one or more pharmaceutically acceptable carriers comprising excipients and auxiliaries, which facilitate processing of the active ingredients (HCQ and antiviral agents described herein) into preparations which, can be used pharmaceutically. Proper formulation is dependent upon the route of administration chosen.

For injection, the active ingredient(s) of embodiments of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the active ingredients can be formulated readily by combining the active ingredients described herein with pharmaceutically acceptable carriers well known in the art. Such carriers enable the active ingredient(s) to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredients.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients described herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredient(s for use according to embodiments of the present invention are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient(s and a suitable powder base such as, but not limited to, lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredients. Additionally, suspensions of the active ingredients may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredients may be in powder form for constitution with a suitable vehicle, e.g., sterile, pyrogen-free water, before use.

The active ingredients of embodiments of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Compositions comprising HCQ and an antiviral agent, as described herein, formulated in a compatible pharmaceutical carrier may also be prepared, packaged in a packaging material, and identified in or on the packaging material, for treatment of an HCV-related disease, as is detailed herein.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials:

Chloroquine diphosphate was obtained from Sigma; hydroxychloroquine sulfate was obtained from Sigma;

interferon-α (human, PEGylated) (Peginterferon alfa-2b) was obtained from Schering Plough;

ribavirin was obtained from Sigma-Aldrich.

Boceprevir and NM-107 were synthesized as described in the literature.

In Vitro HCV Replicon Model:

Studies on hepatitis C virus (HCV) replication have been greatly advanced by the development of cell culture models known as replicon systems.

The hepatoma cell line Huh7 is a subclone derived from cell line 9-13. A Huh7 cell line which expresses an HCV genotype 1b replicon 1377/NS3-3' (accession no. AJ242652) was created by Lohmann et al. [Lohmann et al., Science 1999, 285:110-113]. A replicon-containing cell culture, designated GS4.3, was obtained from Dr. Christoph Seeger (Institute for Cancer Research, Fox Chase Cancer Center, Philadelphia, Pa.), and was prepared as described in Zhu et al. [*J Virol* 2003, 77:9204-9210].

Figure 1:
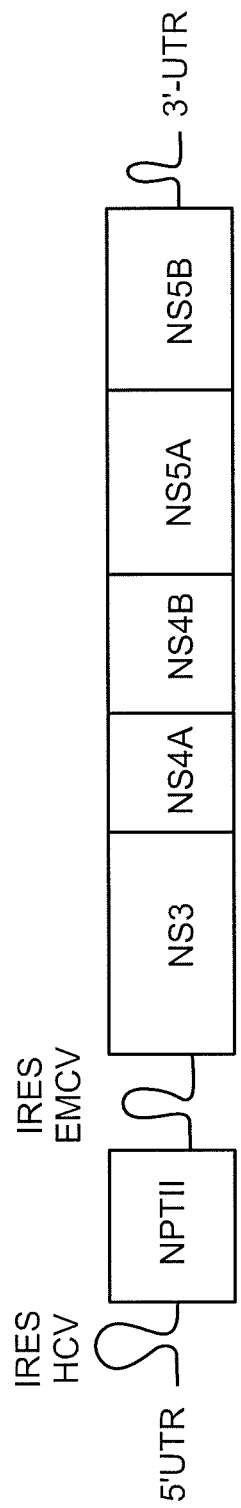
FIG. 1 is a drawing showing the structure of the HCV RNA replicon of cell line Huh 7.

As shown in FIG. 1, the replicon consists of a subgenomic HCV sequence in which the gene unit encoding the HCV structural proteins is replaced by the gene encoding the neomycin phosphotransferase II (NPTII). NPTII expression is under the control of the HCV internal ribosome entry site (IRES), whereas the translation of the region that produces HCV proteins NS3 to NS5 (up to the authentic 3'-UTR) is controlled by the encephalomyocarditis virus (EMCV) internal ribosome entry site (IRES). The NS3 protein cleaves the HCV polyprotein to release mature NS3, NS4A, NS4B, NS5A and NS5B proteins that are required for HCV replication.

This construct is similar to the replicon present in the cell line 9-13 and provides stable NPTII expression for the screening of antiviral agents.

Culture and Treatment of Huh 7 Cells:

Huh7 cells were maintained at 37° C., in an atmosphere of 5% $CO_2$, in DMEM (Dulbecco's modified Eagle medium) supplemented with 2 mM L-glutamine, non-essential amino acids (NEAA), 10% fetal bovine serum (FBS) and 500 mg/ml geneticin. Cells were sub-divided at a 1:3 or 1:4 ratio every 2-3 days. 24 hours prior to the assay, Huh7 cells were collected, counted, plated in 96-well plates at 7,500 cells/well in 100 ml standard maintenance medium, and incubated in the conditions above. To initiate the assay, culture medium was removed, and cells were washed once with PBS (phosphate buffer saline). For control compounds only, 90 ml assay medium (DMEM with L-glutamine, NEAA, and 10% FBS) was added.

Test compounds were prepared as a 10× stock in assay medium. Serial dilutions of compounds in assay medium were added in a total volume of 10 µl, and the plates were then rocked to mix, and incubated as described above for 72 hours.

Human interferon-α (Peginterferon alfa-2b) and ribavirin are hepatitis C virus inhibitors that reduce RNA replication, and were included in each run as positive control compounds. Positive control compounds were added in duplicate at two different concentrations, 1 pM and 1 nM for interferon, and 100 µM and 200 µM for ribavirin, in order to provide low and high control values.

Quantification of HCV Levels:

HCV RNA levels were measured using TaqMan® RT-PCR. Total cellular RNA was isolated and amplified by using a RealTime HCV assay (m1000TM Automated Sample Preparation System and m2000rtTM instrument for reverse transcription, PCR amplification, and detection/quantitation, Abbott Molecular Inc.), which detects and quantitates HCV genotypes 1-6. The molecular genotyping method targets the 5'-untranslated (UTR) region of the virus genome (see FIG. 1) and is based on an amplification of the viral genome. An internal control, simultaneously amplified by RT-PCR, served to demonstrate that the process proceeded correctly for each sample. A negative control, low positive control and high positive control were also introduced. Results are reported in International Units per ml (IU/ml), and 1 IU/ml=4.3 copies/ml. The lower limit of detection was 12 IU/ml with ≥95% probability. The dynamic range of the assay extended from 12 to 100,000,000 IU/ml. The $EC_{50}$ was defined as the concentration of compound at which the HCV RNA level in the replicon cells was reduced by 50%.

Quantification of Cytotoxicity:

In order to measure any cytotoxic effect, the viabilities of the replicon cells following 72 hours of treatment with compound were determined using an MTS (3-[4,5-dimethylthiazol-2-yl]-5-[3-carboxymethoxyphenyl]-2-[4-sulfophenyl]-2H tetrazolium inner salt) assay (CellTiter 96® AQueous One Solution Cell Proliferation Assay; Promega). The $CC_{50}$ was defined as the concentration of the compound at which cell viability was reduced by 50%.

Analysis of Antiviral Drug Combinations:

Antiviral assays were performed by treating Huh7 cells with a combination of two compounds, as described hereinabove for Huh7 cells. Each combination of drugs was assayed in triplicate.

The effects of drug combinations were evaluated according to the method described by Prichard & Shipman [*Antiviral Res* 1990, 14:181-205]. The theoretical additive effect was calculated from the dose-response curves of individual compounds by the equation $Z=X+Y(1-X)$ (an equation referred to in the art as a Bliss independence model), where X and Y represent the inhibition produced by the individual compounds and Z represents the theoretical effect produced by the combination of compounds. The experimental results were normalized to the theoretical results expected for an additive effect (i.e., "Z"), and the theoretical additive surface was then subtracted from the actual experimental surface, to obtain a horizontal surface which represents synergy between the drugs. Thus, when the surface equals the zero plane, the combination is additive rather than synergistic. A surface that lies above the zero plane (e.g., at least 20%) indicates a synergistic effect of the combination and a surface lower than the zero plane (e.g., below minus 20%) indicates antagonism between the drugs.

The effects of drug combinations were also evaluated by calculating a Combination Index (CI) for three different drug ratios in a Loewe additivity model, using CalcuSyn software based on the method described by Chou & Talalay [*Trends Pharmacol Sci* 1983, 4:450-454]. CI values of <1, 1, and >1 indicate synergy, an additive effect, and antagonism, respectively.

The effects of drug combinations were also evaluated by standard isobologram analysis, using CalcuSyn software.

Example 1

Effect of Hydroxychloroquine in Combination with Interferon-α on HCV RNA Replication Huh7 cells were treated with various concentrations (0, 0.22, 0.66, 2, 8 and 18 µM) of hydroxychloroquine sulfate (HCQ) in combination with various concentrations (0, 0.41, 1.23, 3.7, 11.1, 33.3, 100 and 300 IU/ml) of PEGylated human interferon-α (Peginterferon alfa-2b), as described hereinabove. The levels of HCV RNA were measured by RT-PCR, and the results were analyzed according to Prichard-Shipman, Chou-Talalay and isobologram models, as described hereinabove. In addition, cytotoxicity of the tested combinations of HCQ and interferon-α (IFNα) was determined as described hereinabove.

As shown in FIG. 2, HCQ and IFNα each inhibited HCV RNA replication in a dose dependent manner, both alone and in combination.

As shown in FIGS. 3A and 3B, HCQ and IFNα exhibited a synergistic effect in combination, as determined according to a Prichard-Shipman model. The synergistic effect was particularly strong for a combination of 3.7 IU/ml IFNα and 6 µM HCQ, for which the inhibition of HCV was 30% more than expected for an additive effect.

Table 1 presents the Combination Index (CI) values for combinations of hydroxychloroquine (HCQ) and interferon-α (IFNα) calculated according to a Chou-Talalay model.

As shown in Table 1, HCQ and IFNα exhibited a synergistic effect in combination, with the calculated combination index values all being considerably lower than 1.

TABLE 1

| IFNα (IU/ml):HCQ (µM) | Combination Index | | |
|---|---|---|---|
| ratio | $ED_{50}$ | $ED_{75}$ | $ED_{90}$ |
| 6:1 | 0.69 | 0.73 | 0.77 |
| 2:1 | 0.45 | 0.47 | 0.49 |
| 1:2 | 0.56 | 0.56 | 0.56 |

$ED_{50}$, $ED_{75}$ and $ED_{90}$ represent amount of drug which result in 50%, 75% and 90% inhibition of viral activity.

As shown in FIG. 4, HCQ and IFNα exhibited a synergistic effect in combination, as determined by an isobologram.

The agreement between the various models indicates that hydroxychloroquine and interferon-α exhibit a considerable synergistic effect when administered in combination.

As shown in FIG. 5, cell viability was not affected by the tested doses of IFNα, and was only slightly reduced by the highest tested dose (18 µM) of HCQ.

These results indicate that most of the tested combinations of HCQ and IFNα, including combinations which exhibited a particularly strong synergy, are substantially non-toxic.

For comparison, chloroquine diphosphate was tested in combination with IFNα, using the same procedures as described for HCQ. Chloroquine and IFNα each inhibited HCV RNA replication (data not shown).

Figure 6:
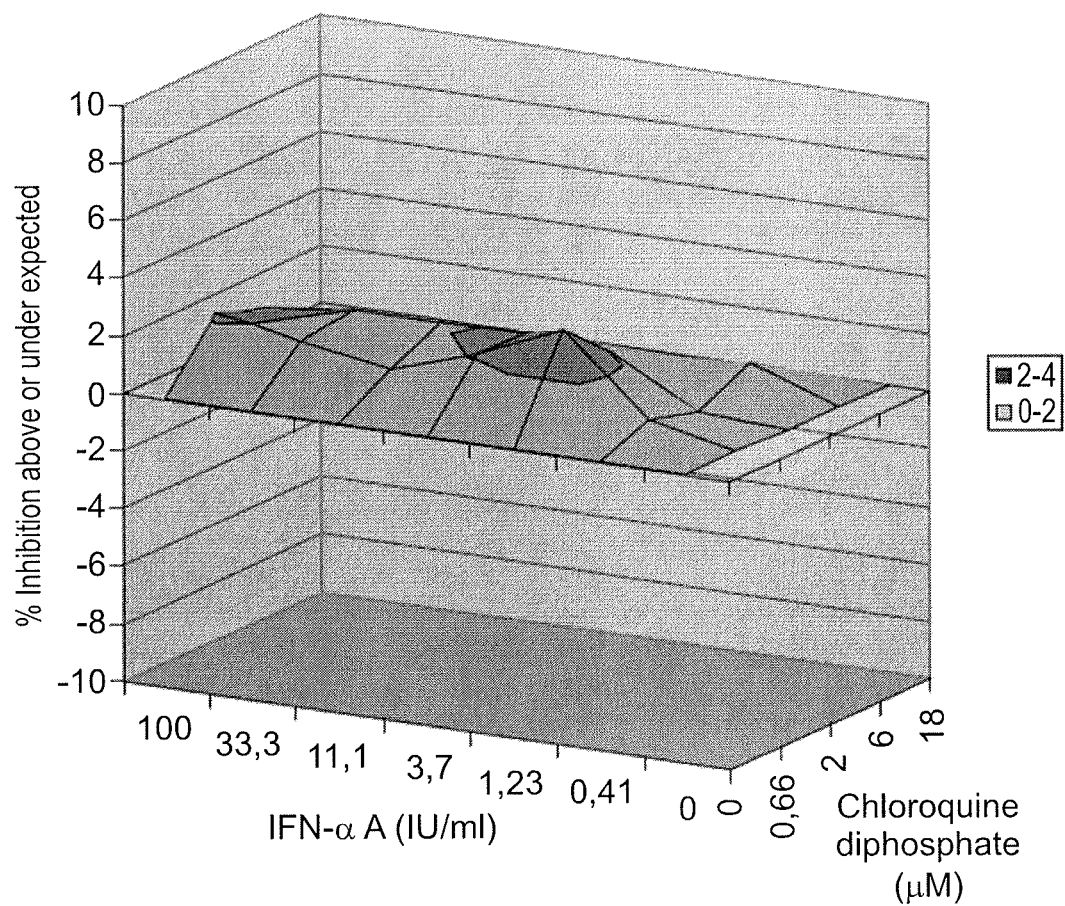
FIG. 6 is a graph showing the difference between a measured antiviral effect of a combination of 0, 0.66, 2, 6 or 18 µM chloroquine with 0, 0.41, 1.23, 3.7, 11.1, 33.3, or 100 IU/ml interferon-α (IFN-a A) and the theoretical antiviral effect expected according to a Prichard-Shipman model of an additive effect (positive values indicate synergy, negative values indicate antagonism)

As shown in FIG. 6, chloroquine did not exhibit any appreciable synergistic effect in combination with IFNα, as determined according to a Prichard-Shipman model.

Example 2

Mechanistic Insights

Effect of Hydroxychloroquine on NF-κB Signaling in HCV Replicon Cells:

The Huh7 harboring replicon model was used to assess the effect of hydroxychloroquine (HCQ) on HCV infection.

In one set of experiments, HCV replicon-Huh-7/neo cells were seeded in 96-well plate for 16 hours. Then cells were incubated with several concentrations of HCQ for 72 hours. Replication levels of HCV replicon were determined by quantification of a replicon-borne neomycin gene product (NPT II, % NPTII). Data is presented in FIG. 7. Bars represent the mean of duplicate wells expressed as percentages compared to the control cells, errors indicate standard deviation (SD). Differences were compared for the HCQ-treated conditions to the corresponding untreated one using a Student t-test. Basically p-values less than 0.05 were considered as statistically significant and are represented by an asterisk (*).

In another set of experiments, Huh7 cells harboring HCV replicon were treated during 48 hours with 0.5 µM and 1 µM of HCQ. Immunoblot assay, performed to detect NS5A and HCV core proteins, showed that similarly to HCQ is able to decrease both HCV core and NS5a protein level in a dose-dependent manner, in comparison to the untreated condition, as presented in FIG. 8. Western blotting of α-actin showed equal loading of the samples.

Since NS5A and HCV core proteins have been shown to regulate the expression and/or the activation of cellular genes, the effect of HCQ on global gene expression was evaluated. Huh7 harboring replicon cells were treated for 6, 12 and 24 hours with 10 µM of HCQ. Each condition was performed in duplicate. Total RNA extracted from cells was hybridized to Whole Human Genome Agilent 4×44K for gene expression analysis.

After normalization, annotated genes in each duplicate whose relative intensity values were higher than background were selected. The number of modulated genes was determined using filtering according to a Fold Change (FC) based selection: at least a 2 FC at 6 hours, 12 hours and 24 hours.

Fold changes were calculated as follows: gene expression normalized value measured in Huh7 harboring replicon cells treated with 10 µM of HCQ (performed in duplicate) divided by the corresponding value in untreated cells, at each time point of kinetic 6 hours, 12 hours and 24 hours. Fold Changes (FC) cut-off were fixed at 12 hours and 24 hours as FC≥2 for an up-regulation and FC≤0.5 for down-regulation. Data is presented in Tables 2 and 3.

As shown in Table 2, most of the modulated genes were down-regulated, and the effect was more pronounced at 24 hours of treatment.

As shown in Table 3, among the 23 modulated genes, only 3 are found to be up-regulated (FC≥2; in bold) while 20 are significantly repressed (FC≤0.5, in italic).

TABLE 2

Number of genes transcriptionally modulated by HCQ treatment

| | Up-regulated | Down-regulated |
|---|---|---|
| 6 hours | / | 5 |
| 12 hours | 7 | 30 |
| 24 hours | 23 | 63 |

TABLE 3

| Agilent Probe Name | Official Gene Symbol | RefSeq mRNA ID | Mean value of Fold Change (replicate) | | |
|---|---|---|---|---|---|
| | | | HCQ 6 h | HCQ 12 h | HCQ 24 h |
| A_23_P161218 | ANKRD1 | NM_014391 | 0.8 | 0.3 | 0.2 |
| A_23_P259071 | AREG | NM_001657 | 1.0 | 0.5 | 0.3 |
| A_23_P253350 | C8orf4 | NM_020130 | 0.7 | 0.3 | 0.2 |
| A_24_P135319 | CGNL1 | NM_032866 | 0.9 | 0.4 | 0.4 |
| A_23_P19663 | CTGF | NM_001901 | 0.8 | 0.4 | 0.4 |
| A_23_P7144 | CXCL1 | NM_001511 | 0.7 | 0.2 | 0.2 |
| A_23_P110204 | CXCL5 | NM_002994 | 0.8 | 0.4 | 0.3 |
| A_23_P163402 | CYP1A1 | NM_000499 | 1.1 | 0.2 | 0.3 |
| A_23_P46429 | CYR61 | NM_001554 | 0.7 | 0.4 | 0.3 |
| A_23_P108751 | FHL2 | NM_201555 | 0.8 | 0.3 | 0.2 |
| A_23_P64721 | GPR109B | NM_006018 | 0.9 | 0.4 | 0.4 |
| A_24_P300394 | GSTA2 | NM_000846 | 0.9 | 0.5 | 0.4 |
| A_23_P153320 | ICAM1 | NM_000201 | 0.7 | 0.4 | 0.4 |
| A_23_P27584 | MYADM | NM_001020818 | 1.0 | 0.4 | 0.4 |
| A_23_P202156 | NFKB2 | NM_002502 | 0.8 | 0.4 | 0.4 |
| A_23_P127584 | NNMT | NM_006169 | 0.8 | 0.5 | 0.1 |
| A_23_P315815 | NRG1 | NM_013961 | 0.7 | 0.4 | 0.2 |
| A_23_P338912 | PHLDA1 | NM_007350 | 0.7 | 0.5 | 0.4 |
| A_23_P55706 | RELB | NM_006509 | 0.9 | 0.3 | 0.3 |
| A_23_P51136 | RHOB | NM_004040 | 0.8 | 0.4 | 0.3 |
| A_23_P367899 | EPOR | NM_000121 | 1.2 | 2.2 | 2.2 |
| A_24_P20327 | KLF15 | NM_014079 | 0.8 | 2.3 | 3.0 |
| A_24_P406664 | RAD23B | NM_002874 | 0.8 | 2.6 | 3.3 |

Interestingly, two down-regulated genes encode for RELB and NFKB2 transcription factors. Furthermore, several known target genes of the NF-κB pathway were concomitantly found down-regulated: ICAM1, CXCL1, CXCL5 and CYR61/CCN1. Other down-regulated genes such as C8orf4, GPR109B, NRG1, PHLDA1 and RHOB are functionally linked to the apoptotic process GO term.

Since NS5A and HCV core protein are known to activate NF-κB, the down regulation of genes encoding related transcriptional factors by the HCQ might reflect a consequence of an inhibition of the viral protein expression.

Effect of HCQ treatment on gene expression modulations induced by HCV:

Although the HCV replicon model permits to study the intracellular modulations occurring during the HCV replication steps, this model is limited by the inability to support HCV infectious particles production, due to an incomplete viral life cycle, and hence does not permit to study molecular events occurring during the HCV entry step. In addition, this model does not allow studying the intracellular modifications resulting from acute infection.

Thus, in order to the global impact of HCQ on HCV infection, gene expression profiling of an infectious HCV cell culture (HCVcc) system, which is closer to the natural infection than the replicon model, was performed. Gene expression analysis was performed on HCV infected and uninfected cells to study the global impact of infection; and on HCV infected cells treated with HCQ, to identify the HCQ effect on host gene expression previously modulated by HCV.

First, gene expression modulations occurring during infection were analyzed by comparing uninfected Huh7 cells and JFH1/CsN6A4 infected Huh7 cells at 6 hours, 24 hours and 48 hours kinetic time points post-infection. It is noted that this model is a model for antiviral-resistant HCV genotype.

Genes whose expression is modulated by infection were selected according to data filtering on the basis of at least a twofold change of expression compared to the uninfected control condition. Percentages of modulated genes were calculated in comparison with 10238 genes, the total number of meaningful genes (significantly expressed genes above the background and annotated by a RefSeq mRNA ID).

The proportion of genes significantly regulated by infection for each kinetic time point is illustrated in FIG. 9A. At 6 hours, less than 1% of the total number of genes was found modulated (6 down-regulated and 15 up-regulated). At 24 hours, about 13% of genes (1319 genes) are regulated, among which about 8% are upregulated and about 5% are down-regulated. At 48 hours, about 17% of genes (1736 genes) are modulated by HCV infection, among which about 9% are up-regulated and about 8% are down-repressed.

Functional analysis of the transcriptional modulations induced by HCV infection was conducted in parallel by two complementary approaches: a global approach using the Functional Annotation Clustering (FAC) from DAVID database and a text-mining basis approach using the Predict-Search Software™

Global Analysis Using FAC David Tool:

For the global approach performed using DAVID FAC tool, analysis was focused on the 1736 genes regulated after 48 hours of infection, among which 895 are up-regulated and 842 are down-regulated. The FAC showed that several functional annotations are significantly over-represented in this dataset. The most representative functional clusters are presented on the heatmap represented in FIG. 9B.

Among these enriched functional annotations, focus was made on the following Gene Ontology annotations: NF-κB, viral replication, endoplasmic reticulum (ER), cell response to stress/ER stress/UPR, lysosome and macromolecule catabolic process.

Gene expression analysis was performed on JFH1/CsN6A4 infected Huh7 cells treated or untreated, for 12 hours up to 48 hours, with 40 μM of HCQ. For comparison, and in order to reduce the signal-to-noise ratio, gene expression analysis was also performed on chloroquine (CQ) treated cells, using the same procedures as for HCQ.

Table 4 presents the total number of genes whose expression is modulated from 12 hours up to 48 hours by treatment of both HCQ and CQ, in JFH 1 infected Huh7 cells. The number of modulated genes was determined according to a Fold Change (FC) based selection. A 2 FC cut-off was fixed for HCQ and CQ treated conditions, at 12 hours and 48 hours. FC≥2 corresponds to an up-regulated gene, FC≤0.5 for a down-regulated gene.

As shown in Table 4, and while considering the gene expression modulations in common with HCQ and CQ, it was observed that less than 1% (62 genes) and about 3% (271 genes) of the total number of genes are significantly up-regulated and down-modulated, respectively, after either 12 hours or 48 hours of treatment.

TABLE 4

Number of genes modulated in JFH1 infected Huh7 cells treated by both HCQ and CQ

|  | Up-regulated | Down-regulated |
| --- | --- | --- |
| 12 h | 38 | 9 |
| 48 h | 24 | 262 |

Expression data corresponding to the 1736 modulated genes by infection have also been included in the FAC and the corresponding expression profiles are presented on the heatmaps shown in FIG. 9B.

The expression profiles of host genes differentially expressed (at least a 2 Fold Change, FC, modulation) following 6 hours, 24 hours and up to 48 hours post infection of Huh7 cells with JFH1/CsN6A4 viral particles were characterized using Agilent 4×44K microarray analysis. Expression profiles obtained in other conditions tested were also included: after a 12 hours up to 48 hours treatment with HCQ and CQ. Hierarchical clustering (HCL) of each cluster of selected genes was performed using TMev free software. FC in gene expression were calculated by comparing gene expression in JFH1-infected Huh7 to that in uninfected Huh7 cells at each time point postinfection. FC of these genes were also calculated by comparing HCQ and CQ treated infected cells to that in untreated infected cells at 12 hours and 48 hours kinetic time points post-treatment.

Expression profiles are represented in FIG. 9B on a 2FC scale since FC were log base 2 transformed. Genes shown in red were upregulated, genes shown in green were down-regulated and genes in black were not modulated.

Each sample expression profiles is represented in column, and annotated by a color code horizontal bar figuring on the top of each heatmap. Black bar corresponds to infected conditions, blue bar corresponds to CQ treated condition and yellow bar to HCQ treated cells.

Functional annotations of selected genes regulated by JFH1/CsN6A4 infection performed using DAVID FAC tool showed several GO annotations enriched such as: transcriptional regulation, cell response to stress included ER stress, apoptosis, cell cycle. Several other annotations were found significantly enriched in the set of HCV modulated genes such as viral replication, NF-κB pathway or lipid biosynthetic process. HCQ treatment was shown to counteract most of the expression modulations induced in response to HCV infection.

According to the opposite gene expression profiles observed between HCV infected conditions and either HCQ or CQ treated conditions, it is suggested that HCQ counteracts gene expression modulations occurring during infection.

Because of the highest number of modulations of gene expression has occurred at the 48 hours kinetic time point post-infection, further analysis was performed at this time point.

Thus, to establish the gene regulatory network illustrating the effect of HCQ on HCV infected cells, further analysis was focused on the HCV regulated genes whose expression is modulated at least by a twofold change by a 48 hours treatment of both HCQ and CQ. 118 HCV modulated genes were selected, among which 12 are up-regulated (FC≥2) and 106 are down-regulated (FC≤0.5) by both compounds, as shown in Table 5 and in FIG. 9C.

TABLE 5

| | | Number of genes modulated by both JFH1 infection and HCQ or CQ treatment at 48 h | |
|---|---|---|---|
| | | Up-regulated | Down-regulated |
| JFH1 Infection | Induced | 1 | 104 |
| | Repressed | 11 | 2 |

The obtained data suggest that HCQ mainly acts as a transcriptional inhibitor (in accordance with the data presented in Table 2). Further, it is shown that most of genes whose expression is down-regulated by the HCQ treatment, are found up-regulated by HCV infection and vice versa, genes up-regulated by the HCQ treatment, are found down-regulated by HCV infection. This finding is in agreement with previous results obtained with the global FAC approach.

PredictSearch:

The list of 118 genes whose expression discriminate both infection and HCQ treatment conditions, was submitted to PredictSearch™ software. PredictSearch™ allows identifying correlations between these genes, functional related genes and biological concepts using a text-mining approach. The text-mining algorithm extracts pertinent data related to the selection submitted, among all concepts referenced in the bibliographic data available in the NCBI database. In most cases these additional genes are not found significantly transcriptionally modulated in the microarray data, presumably due to (i) gene may not be modulated in every biological condition considered (herein, in infection and treatment); (ii) gene may have a delay response comparing to the kinetic time point studied; and/or (iii) expression modulations occur at post-transcriptional or post-translational level, which could not be observed in transcriptomic analysis.

The expression profile of the 57 genes selected on the basis of PredictSearch analysis is presented in FIG. 10. Expression profiles of genes obtained in each condition tested were included: at each time point post-infection and after a 48 hours treatment of infected cells with either HCQ or CQ or IFN. These genes were found to be involved in pathways such as ER stress response, autophagy signaling, NF-κB and p53 signaling pathways.

Each sample expression profiles is represented in column, and annotated by a color code horizontal bar figuring on the top of each heatmap. Black bar corresponds to infected conditions, blue bar to CQ treated condition, the yellow bar to HCQ treated cells and the orange one corresponds to IFN treated cells.

These results are in agreement with the global FAC analysis described hereinabove.

Table 6 summarizes the FC measured for these 57 genes in each condition of interest. A schematic representation of this functional biological network is shown in FIG. 11. This network highlights the pathways which are over-expressed in HCV infected cells while repressed by the HCQ treatment.

TABLE 6

| Official Gene Symbol | RefSeq mRNA ID | JFH1 Infection | | | 48 h of antiviral treatment | | |
|---|---|---|---|---|---|---|---|
| | | 6 h | 24 h | 48 h | CQ | HCQ | IFN |
| ATF2 | NM_001880 | 1.0 | 1.6 | 2.5 | 0.8 | 0.7 | 0.4 |
| ATF3 | NM_001040619 | 2.0 | 20.5 | 65.7 | 0.4 | 0.1 | 0.2 |
| ATF4 | NM_001675 | 0.9 | 2.8 | 2.1 | 0.5 | 0.6 | 0.5 |
| ATF7IP | NM_018179 | 0.8 | 2.9 | 3.4 | 0.6 | 0.3 | 0.4 |
| DDIT3 | NM_004083 | 0.9 | 7.5 | 13.9 | 0.4 | 0.3 | 0.1 |
| DDIT4 | NM_019058 | 1.8 | 8.1 | 5.1 | 0.5 | 0.3 | 0.3 |
| DUSP1 | NM_004417 | 1.9 | 6.1 | 20.6 | 0.3 | 0.1 | 0.1 |
| DUSP4 | NM_001394 | 1.1 | 2.4 | 10.8 | 0.4 | 0.2 | 0.2 |
| DUSP8 | NM_004420 | 1.4 | 5.8 | 17.3 | 0.3 | 0.1 | 0.1 |
| TRAF2 | NM_021138 | 1.0 | 1.8 | 2.4 | 0.6 | 0.4 | 0.7 |
| TRAF4 | NM_004295 | 1.0 | 1.9 | 2.8 | 0.4 | 0.3 | 0.7 |
| UBD | NM_006398 | 1.1 | 2.5 | 13.9 | 0.4 | 0.3 | 0.8 |
| AMBRA1 | NM_017749 | 1.0 | 1.2 | 2.6 | 0.7 | 0.4 | 0.4 |
| ATG12 | NM_004707 | 1.0 | 1.4 | 1.3 | 1.2 | 1.1 | 0.8 |
| ATG2A | NM_015104 | 0.9 | 1.8 | 4.0 | 0.5 | 0.2 | 0.3 |
| ATG4B | NM_178326 | 1.1 | 0.4 | 0.8 | 1.5 | 1.6 | 1.3 |
| ATG7 | NM_006395 | 0.8 | 0.9 | 1.3 | 0.7 | 0.7 | 0.9 |
| BECN1 | NM_003766 | 1.1 | 1.6 | 0.8 | 0.8 | 0.9 | 1.4 |
| FOXO3 | NM_001455 | 1.2 | 3.9 | 2.0 | 0.4 | 0.2 | 0.5 |
| GABARAPL1 | NM_031412 | 1.0 | 1.5 | 2.5 | 0.7 | 0.4 | 0.4 |
| MAP1LC3B | NM_022818 | 1.1 | 1.4 | 2.7 | 0.9 | 0.8 | 0.4 |
| PIK3C3 | NM_002647 | 1.0 | 1.8 | 1.8 | 1.0 | 0.7 | 0.5 |
| SQSTM1 | NM_003900 | 1.0 | 2.2 | 4.0 | 0.5 | 0.5 | 0.5 |
| ULK1 | NM_003565 | 1.1 | 3.3 | 3.2 | 0.5 | 0.3 | 0.3 |
| BBC3 | NM_014417 | 1.3 | 7.4 | 19.8 | 0.5 | 0.1 | 0.1 |
| BMF | NM_001003940 | 1.1 | 3.6 | 4.4 | 0.3 | 0.1 | 0.2 |
| DAPK3 | NM_001348 | 1.0 | 2.0 | 4.8 | 0.4 | 0.2 | 0.3 |
| GADD45A | NM_001924 | 1.2 | 4.7 | 7.5 | 0.5 | 0.2 | 0.2 |
| GADD45B | NM_015675 | 1.8 | 2.4 | 11.5 | 0.6 | 0.2 | 0.1 |
| GADD45G | NM_006705 | 0.9 | 1.7 | 5.2 | 1.2 | 0.7 | 0.3 |
| HRK | NM_003806 | 1.1 | 0.7 | 1.7 | 0.4 | 0.4 | 0.7 |
| JUN | NM_002228 | 1.4 | 3.6 | 7.7 | 0.4 | 0.2 | 0.2 |
| MYC | NM_002467 | 1.2 | 2.5 | 9.7 | 0.5 | 0.4 | 0.3 |
| PDRG1 | NM_030815 | 0.9 | 1.7 | 2.2 | 0.7 | 0.7 | 0.6 |
| PRKAA1 | NM_206907 | 0.9 | 1.5 | 3.5 | 0.7 | 0.6 | 0.3 |
| SESN2 | NM_031459 | 1.4 | 9.9 | 17.3 | 0.4 | 0.2 | 0.2 |
| SIRT1 | NM_012238 | 1.2 | 4.2 | 2.9 | 0.8 | 0.7 | 0.5 |
| STK11 | NM_000455 | 0.9 | 1.4 | 1.3 | 0.6 | 0.5 | 0.9 |
| TNFRSF10B | NM_003842 | 1.2 | 1.8 | 2.1 | 0.8 | 0.7 | 0.6 |
| TSC1 | NM_000368 | 1.0 | 0.5 | 1.2 | 1.2 | 1.5 | 0.6 |
| TSC2 | NM_000548 | 1.0 | 1.2 | 1.1 | 0.6 | 0.4 | 0.9 |
| BCL3 | NM_005178 | 1.3 | 2.3 | 5.4 | 0.6 | 0.5 | 0.4 |
| CXCL5 | NM_002994 | 1.1 | 1.6 | 3.7 | 0.8 | 0.7 | 1.3 |
| CYP1A1 | NM_000499 | 1.4 | 1.8 | 4.0 | 0.5 | 0.1 | 0.4 |
| CYR61 | NM_001554 | 1.8 | 2.5 | 6.7 | 0.3 | 0.2 | 0.2 |
| ICAM1 | NM_000201 | 0.9 | 1.2 | 2.7 | 0.7 | 1.2 | 2.0 |
| IKBKAP | NM_003640 | 1.1 | 1.0 | 0.3 | 1.2 | 2.0 | 1.3 |
| NFKB1 | NM_003998 | 1.0 | 1.3 | 1.7 | 0.8 | 1.0 | 0.8 |
| NFKBIA | NM_020529 | 1.1 | 1.6 | 8.7 | 0.6 | 0.5 | 0.3 |
| NFKBIB | NM_001001716 | 0.9 | 1.9 | 3.4 | 0.6 | 0.6 | 0.4 |
| NFKBIE | NM_004556 | 1.1 | 2.1 | 8.1 | 0.6 | 0.4 | 0.3 |
| NFKBIL2 | NM_013432 | 1.0 | 1.1 | 0.9 | 0.7 | 0.4 | 1.5 |
| NKIRAS1 | NM_020345 | 1.1 | 2.2 | 3.4 | 0.8 | 0.4 | 0.4 |
| NKIRAS2 | NM_001001349 | 0.9 | 1.1 | 1.5 | 0.8 | 0.6 | 1.0 |
| NKRF | NM_017544 | 1.0 | 2.0 | 1.3 | 1.1 | 1.3 | 1.0 |
| RELB | NM_006509 | 1.3 | 3.1 | 13.6 | 0.7 | 0.3 | 0.4 |
| TANK | NM_133484 | 1.0 | 0.9 | 0.8 | 1.3 | 1.3 | 1.2 |

Effect of Hydroxychloroquine on HCV-Induced NF-κB Signaling:

Among the 57 genes selected, 16 genes that are functionally related to the NF-κB activation or downstream signaling were found: IKBKAP, NFKB1, NFKBIA, NFKBIB, NFKBIE, NFKBIL2, NKIRAS1, NKIRAS2, NKRF, TANK, RELB, CYP1A1 and CYR61. Most of these genes are found up-regulated by HCV infection.

Among these 16 genes, expression of several genes was found up-regulated by HCV while clearly repressed (FC≤0.5) by both HCQ and CQ (CYP1A1 and CYR61). Most of the other genes are differentially expressed by infection and after 48 hours of treatment by HCQ while slightly modulated by CQ (0.6≤FC≤0.8): NFKBIA, NFKBIB, NFKBIE, NKIRAS1 and RELB. Several other genes that were not found significantly modulated according to their expression ratios were included in the network because they belong to this pathway: NFKB1, NFKBIL2, NKIRAS2, NKRF and TANK. In addition, IKBKAP was included according to its expression profile: down-regulated by infection while increased by HCQ treatment. BBC3 and MYC which are related to the p53 and the NF-κB signaling were also found significantly modulated by both conditions: highly induced by infection while severely repressed by both compounds. Moreover, BBC3, MYC, CYR61 and other genes such as CXCL5, ICAM1 and BCL3, are direct transcriptional targets of the NF-κB transcription factor genes (see, for example, wwwdotbioinfodotlifldotfr/NF-KB/). CXCL5, ICAM1 and BCL3 mRNA expression is increased during infection while slightly repressed (CXCL5 and BCL3) or unchanged (ICAM1) by the HCQ treatment.

Previous studies suggested that HCV infection increases the expression level of several NF-κB related genes. It is demonstrated herein that HCQ treatment counteracts this HCV-induced NF-κB pathway, in accordance with the results on HCV replicon described hereinabove.

Effect of Hydroxychloroquine on HCV-Induced ER Stress Response and the Autophagic Pathway:

Among the initial set of 57 genes, 12 other genes which were found to be positively modulated by infection while significantly repressed by the HCQ treatment, are functionally related to the ER stress response and the subsequent UPR activation: ATF2, ATF3, ATF4, ATF71P, DDIT3, DDIT4, DUSP1, DUSP4, DUSP8, TRAF2, TRAF4, UBD (see, Table 6 and FIGS. 10 and 11).

ATF2, ATF3, ATF4 and ATF71P are members of mammalian activation transcription factor/cAMP responsive element-binding (CREB) protein family. Transcription and translation of these ATFs genes is inducible in stress conditions such as ER stress. ATF2 encoded protein, with c-Jun, stimulates the CRE-dependent transcription and directly induces activation of DUSP1, 4, and 8 to limit the activities of stress kinases JNK and p38. In addition, ATF3 is known to be involved in several pathways such as p53-dependant apoptosis, and T helper cell type (Th)1 differentiation activation. ATF4 is the main transcriptional regulator of the cellular hypoxic response to the Unfolded Protein Response (UPR) and has a key role in the regulation of autophagy in response to ER stress. ATF4 provides a direct mechanistic link between the UPR and the autophagic machinery, probably through DDIT4. Indeed, an increased ATF4 expression has been shown to be required and sufficient to upregulate DDIT4.

DDIT4 and DDIT3 are DNA-damage inducible transcripts, activated and also up-regulated by ER stress and involved in regulation of autophagy. DDIT3/CHOP, a member of the C/EBP family of transcription factors, is also involved in apoptosis promotion and in the proinflammatory NF-κB.

DUSP1, 4 and 8 are dual specificity protein phosphatases, which play an important role in the human cellular response to environmental stress as well as in the negative regulation of cellular proliferation. These genes negatively regulate members of the mitogen-activated protein (MAP) kinase superfamily (MAPK/ERK, SAPK/JNK, p38), which are associated with cellular proliferation and differentiation. The DUSP4/MPK-2 gene product inactivates ERK 1, ERK2 and JNK gene product. The DUSP8/MPK-1 gene product inactivates SAPK/JNK and p38.

TRAF2 and TRAF4 genes encode proteins members of the TNF receptor associated factor (TRAF) family. TRAF2 is required for TNF-alpha-mediated activation of MAPK8/JNK and NF-kappa, functions as a mediator of the anti-apoptotic signals from TNF receptors and is involved in autophagy. TRAF4 is thought to be involved in the oxidative activation of MAPK8/JNK in addition to its role in the regulation of cell death and NF-kappa B activation. UBD/FAT10 is a TNF-alpha-inducible ubiquitin-like protein with a putative role in immune response. It was shown to mediate TNF-alpha-induced NF-kappaB activation.

Twelve (12) others genes involved in the autophagic pathway were included in the network (see, Table 6 and FIGS. 10 and 11). Among them, expression of 6 genes is clearly positively regulated by HCV while repressed by both HCQ and CQ: ULK1, AMBRA1, ATG2A, GABARAPL1, FOXO3 and SQSTM1. Two other genes among the 18 are less strongly repressed by HCQ treatment: PIK3C3 and MAP1LC3B. The four other genes were also included in the network according to their known implication in the autophagic pathway, although no significant transcriptional modulation was measured in both studied conditions: ATG4B, ATG7, ATG12 and BECN1. ATG2A, ATG4B, ATG7 and ATG12 belong to the autophagy related genes (ATGs) family and are involved in the sequential events leading to the activation of autophagic process. The key genes involved in this process are: ULK1 and KIAA0652/ATG13 for the early phase; UVRAG, MAP1LC3B and SQSTM1/P62 for the vesicle nucleation step and, ATG12 and GABARAPL1 for the later vesicle expansion and completion step.

MAP1LC3B/LC3B is a marker of the autophagic process activation because its expression is induced in several stress conditions such as ER stress and the protein MAP1LC3B is highly expressed on the autophagosome surface. SQSTM1, a cargo adaptator, interacts with MAP1LC3B to recruit cargo protein which would be digested in the autophagolysosome.

PredictSearch software also permitted to identify FOXO3, a member of the forkhead family of transcription factors, which functions as a trigger not only of apoptosis but also of autophagy. The autophagic role of FOXO3 in transcriptional induction of genes such as ULK1, ATG13, BECN1, UVRAG/VPS38, PIK3C3, ATG12, GABARAPL1, ATG4B and MAP1LC3B, is known in another pathological condition. FOXO3 transcription level itself is indirectly regulated by the p53 downstream signaling through the SESN2, STK11, PRKAA1 and SIRT1. According to the level of acetylated SIRT1, FOXO3 expression would be increased.

Previous studies have shown that HCV infection induces an ER stress and a subsequent activation of the UPR, which triggers the activation of the autophagic pathway. Notably, it is demonstrated herein that HCQ treatment counteracts the HCV-induced ER stress response, the UPR and the autophagic pathway.

Effect of Hydroxychloroquine on HCV-Induced p53 Signaling Pathway:

Among the initial set of 57 genes, 17 p53-target genes were identified: BBC3, TNFRSF10B, GADD45A, GADD45B, GADD45G, DAPK3, HRK, BMF, PDRG1, MYC, SIRT1, SESN2, PRKAA1, STK11, TSC2, TSC1 and JUN (see, Table 6, and FIGS. 10 and 11). Expression of all these genes, except for HRK, STK11, TSC2 and TSC1 is up-regulated by HCV infection.

All of these genes, except SIRT1, PRKAA1, TSC1, TNFRSF10B, GADD45G and PDRG1 were also found to be down-regulated by the HCQ treatment. 3 genes transcriptionally regulated by p53 (TSC2, PRKAA1 and SESN2) are closely related to the activation of the NF-κB pathway, to the inhibition of the Rheb/mTOR signaling and to the transcriptional activation of FOXO3. STK11, TSC2 and TSC1 were also included in the network according to their known implication in the p53 pathway, although no significant transcriptional modulation was measured in both conditions. It is noteworthy that expression of the p53 transcription factor itself was not shown to be modulated by both. However, it is well known that the transcriptional activity of p53 is mostly regulated by its localization in nucleus or in cytoplasm.

While previous studies have shown that HCV infection induces p53 signaling pathway, it is demonstrated herein that HCQ treatment counteracts the HCV-induced p53 pathway.

In summary, the gene regulatory network demonstrated herein illustrates the molecular events modulated both by HCV infection and by the HCQ treatment. Gene expression analysis of these transcriptional modulations revealed that HCQ treatment strongly decreases the HCV-induced NF-κB signaling, the ER stress, UPR, autophagic signaling and the p53-signaling pathways, suggesting that the HCQ antiviral effect is mediated through the repression of these HCV-induced pathways.

Effect of HCQ on HCV-Induced ER Stress Response, Autophagy, NF-κB and p53 Signaling Pathways:

To determine whether these HCQ inhibitory effects on the HCV-induced signaling pathways result from a HCQ direct targeting or are a consequence of the viral eradication induced by the HCQ effect on the lysosomal pH, further analysis was performed to study the gene expression modulations induced after a 48 hours treatment with Interferon α (IFN). IFN is an antiviral agent currently used in combination with ribavirin (RBV) as standard therapy against chronic HCV infection. The molecular mechanisms involved in the antiviral effect induced by exogenous IFN administration have been well described.

Gene expression profiling was performed on JFH1/CsN6A4 huh7 cells treated with 100 IU IFN during 48 hours.

As expected, it was shown that exogenous IFN stimulation of HCV infected cells significantly increased expression of genes involved in the IFN signaling: CXCL1, CXCL5, EIF2AK2, ICAM1, ICAM2, IFI35, IFIT1, IFITM2, IFITM3, ISG20, 15 PML, STAT1, ISG15 and WARS. None of the genes regulated by IFN were found to be modulated by a 48 hours treatment with HCQ, except IFIT1.

On the basis of the selected 57 genes, the gene expression profiles obtained after IFNα treatment were compared to those previously obtained after the HCQ treatment, at the 48 hours kinetic time point. For each gene of the list, the FC was calculated. The results are presented in Table 6. The expression data corresponding to the IFN treated condition were included in the hierarchical clustering presented in FIG. 10.

Similarly to HCQ (and CQ), IFN was shown to repress expression of the HCV-induced genes involved in the following pathways: NF-κB signaling (NFKBIA, NFKBIB, NFKBIE, NKIRAS1, RELB, CY1PA1, CYR61 and BCL3), the ER/UPR stress response signaling (ATF2,3,4,7IP, DDIT3,4, DUSP1,4,8), the autophagic pathway (ULK1, AMBRA1, ATG2A, GABARAPL1, FOXO3 and SQSTM1) and the p53 signaling (BBC3, GADD45A, GADD45B, DAPK3, BMF, MYC, JUN, and SESN2).

Several other genes that belong to the set of 57 selected genes were found differently modulated by IFN and HCQ treatment. These include, for example, genes involved in the ER/UPR signaling (TRAF2, TRAF4 and UBD), in the autophagy pathway (PIK3C3 and MAP1LC3B), and in the p53 signaling (SIRT1, PRKAA1, STK11, TSC2, GADD45G and HRK). Interestingly, the slightly HCV-induced expression of PIK3C3 (FC: 1.8) is repressed by IFN (FC: 0.5) although it is not considerably modulated by the HCQ or CQ treatment (FC—CQ: 1, HCQ: 0.7). In addition, the HCV-induced expression of PRKAA1 and MAP1LC3B is clearly reduced by IFN (FC=0.3 and 0.4 respectively) while CQ (FC=0.7 and 0.9) and HCQ (FC=0.6 and 0.8) more slightly reduced them. It can be noted that on the basis of the calculated expression ratios, HCQ and IFN have a similar greater repressive effect than CQ.

In conclusion, it is shown herein that the IFN and the HCQ treatment of HCV infected cells have a similar repressive effect on the HCV-induced pathways (ER stress, UPR, NFKB, autophagy, p53 signalings), demonstrating that the HCQ inhibitory effect observed on these HCV-induced biological pathways is a consequence of the viral reduction occurring in response to an upstream antiviral direct effect of HCQ (or IFN).

qRT-PCR and Nanostring Validation of Selected Host Gene Expression:

An mRNA quantification using a SYBR-Green qRT-PCR approach and using NanoString technology was performed in order to validate the data obtained through microarray analysis. The expression level for several key genes of the network (see, FIG. 10) was investigated in the RNA extracted at the 48 hours kinetic point and at each following conditions: infected cells (Hi/H), cells treated with CQ (HiCQ/Hi) or with HCQ (HiCQd/Hi) or with IFN(HiIFN/Hi).

SYBRGreen qRT-PCR and Nanostring quantification were performed according to common procedures. Ratios were calculated on the basis of relative signal of a given gene normalized to RPL19 and RPL0 in case of RT-PCR. Nanostring signal normalization was performed using expression measured for additional 3 other genes (CLTC, POLR1B and RPL19). Expression ratios were log base2 transformed therefore a positive value corresponds to an induction ratio while a negative value to a repression ratio.

The obtained data is presented in FIG. 14, and further supports that the microarrays, the RT-qPCR and the Nanostring experiments demonstrated reproducible gene expression patterns, although higher FC values were obtained with Nanostring for most of the genes tested.

The microarray expression of the HCV induced NF-κB related gene CYR61 was confirmed by Nanostring. In addition, RT-PCR and NanoString analyses confirmed microarray relative expression ratios measured for autophagic markers such as ULK1, and MAP1LC3B/LC3. Expression of key genes that trigger autophagy (FOXO3 and SIRT1) was also validated, except for PRKAA1.

While there is a discordance between the microarray result and both RT-PCR and Nanostring ratios determined for the PRKAA1 mRNA in the infected condition, IT can be suggested that PRKAA1 expression is rather repressed than induced by infection.

The HCQ inhibitory effect on the HCV induced genes involved in the p53 signaling (BBC3 and SESN2) was also confirmed. Finally, the microarray expression ratios of genes involved in the IFN signaling (ISG15, STAT1, and WARS) were also confirmed by Nanostring technology.

Example 3

Effect of Hydroxychloroquine in Combination with Polymerase and Protease Inhibitors on HCV RNA Replication Huh7 cells were treated with various concentrations (0, 0.22, 0.66, 2, 6 and 18 μM) of hydroxychloroquine sulfate (HCQ) in combination with various concentrations of the antiviral agents NM-107 and boceprevir, in order to determine whether the combinations exhibit synergy. The procedures were similar to those described in Example 1 for HCQ+IFN combinations.

NM-107 is a viral polymerase inhibitor. It is more commonly utilized in a prodrug form (valopicitabine is a prodrug of NM-107) than as a drug. Boceprevir is a viral protease inhibitor. Thus, these two compounds represent different families of antiviral agents, both in respect to one another and in respect to IFN.

0, 0.11, 0.33, 1, 3 and 9 µM NM-107 was combined with HCQ, as was 0, 0.041, 0.123, 0.37, 1.1, 3.3 and 10 µM boceprevir. HCV RNA were measured by RT-PCR, and the results were analyzed according to a Prichard-Shipman model, as described hereinabove.

Figure 13A:
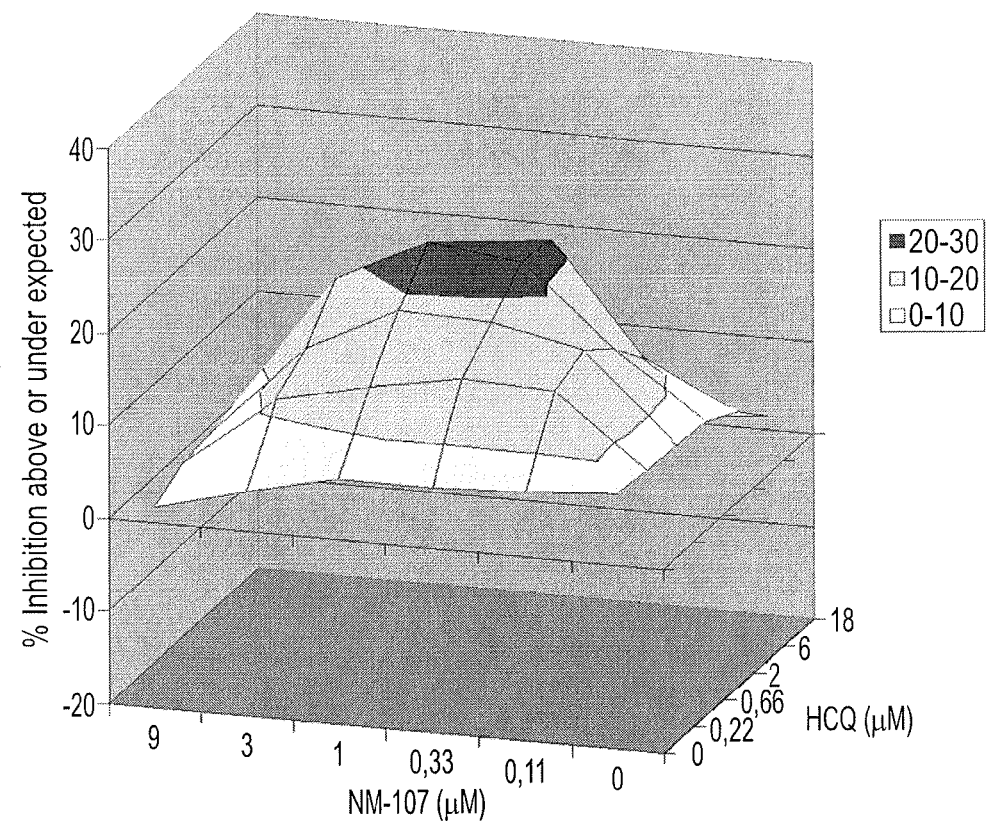
FIGS. 13A and 13B are graphs showing the difference between a measured antiviral effect of a combination of 0, 0.22, 0.66, 2, 6 or 18 μM hydroxychloroquine with 0, 0.11, 0.33, 1, 3.3 or 10 μM NM-107 and the theoretical antiviral effect expected according to a Prichard-Shipman model of an additive effect (positive values indicate synergy, negative values indicate antagonism); the data is presented in 3-dimensional (FIG. 13A) and 2-dimensional (FIG. 13B) schemes.
Figure 13B:
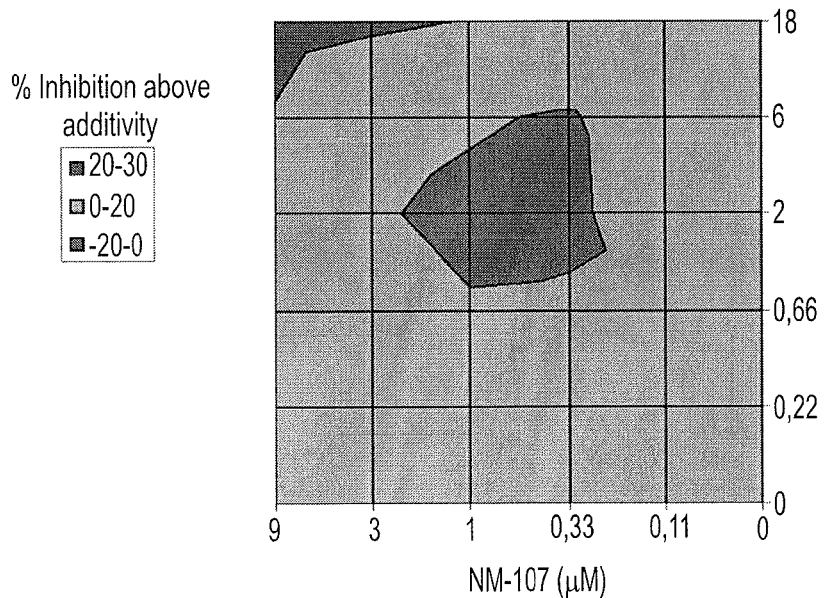

As shown in FIGS. 13A and 13B, HCQ and NM-107 exhibited a synergistic effect in combination. The synergistic effect was strongest for combinations of approximately 0.33 to 1 µM NM-107 and approximately 2 to 6 µM HCQ, for which the inhibition of HCV was over 20% more than expected for an additive effect.

Figure 14A:
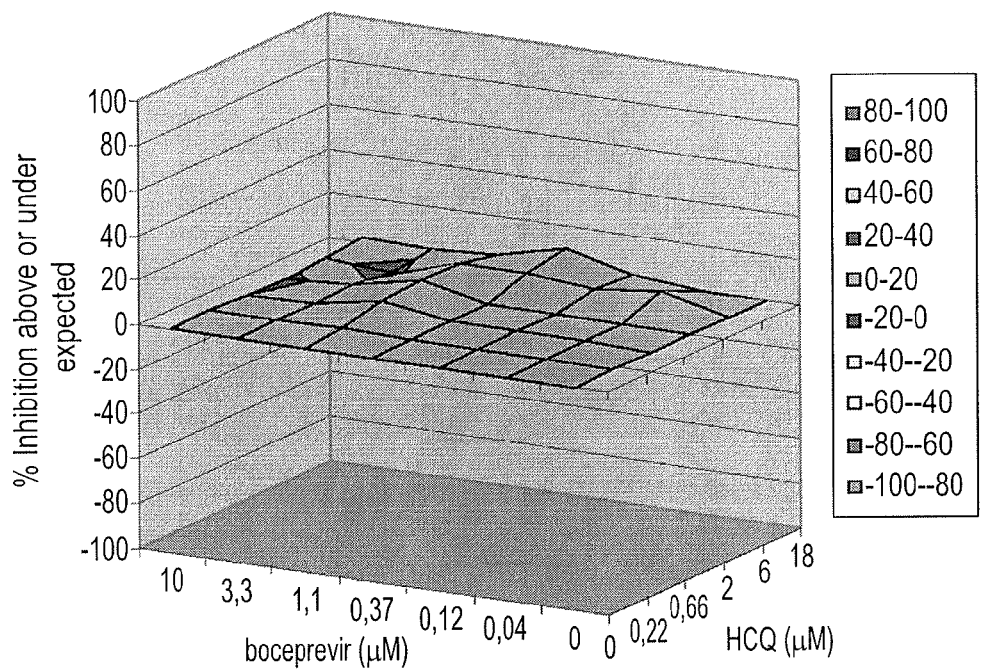
FIGS. 14A and 14B are graphs showing the difference between a measured antiviral effect of a combination of 0, 0.22, 0.66, 2, 6 or 18 μM hydroxychloroquine with 0, 0.041, 0.123, 0.37, 1.1, 3.3 or 10 μM boceprevir and the theoretical antiviral effect expected according to a Prichard-Shipman model of an additive effect (positive values indicate synergy, negative values indicate antagonism); the data is presented in 3-dimensional (FIG. 14A) and 2-dimensional (FIG. 14B) schemes.
Figure 14B:
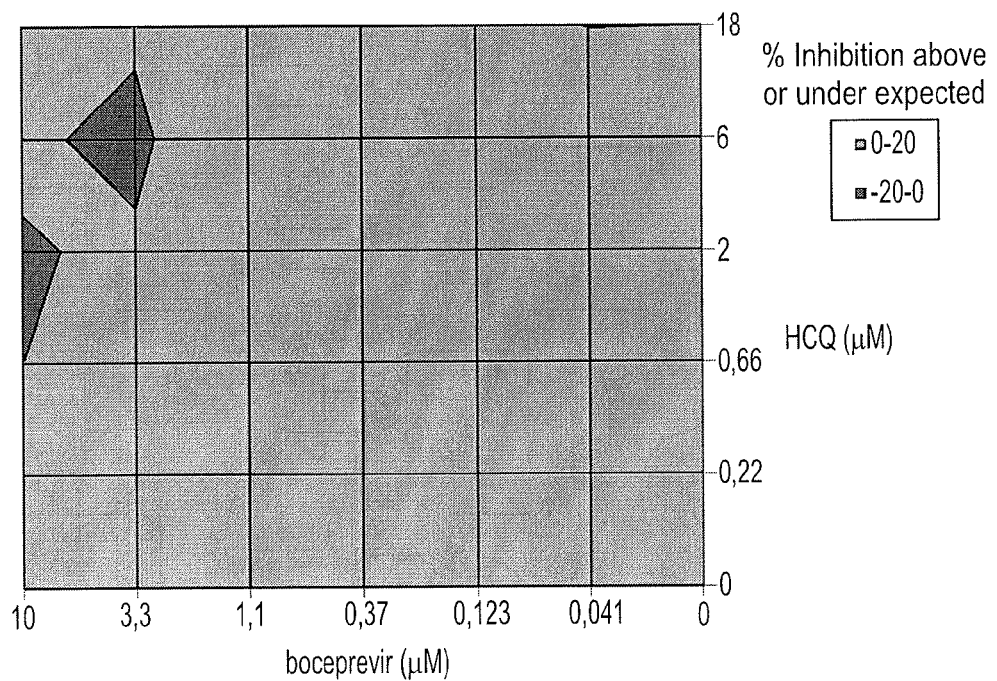

As shown in FIGS. 14A and 14B, HCQ and boceprevir exhibited a modest synergistic effect for a portion of the tested concentration ranges, and an additive effect for other concentration ranges. The synergistic effect was strongest for combinations of approximately 0.37 to 1.1 µM boceprevir and approximately 6 µM HCQ.

Taken in combination with the results presented in Example 1, these results indicate that HCQ exhibits a synergistic antiviral effect with a broad variety of antiviral agents. The results further indicate that synergistic effects with different antiviral agents are strongest at similar HCQ concentrations (e.g., approximately 6 µM HCQ).

Example 4

The Effect of Administering HCQ Combined with PEG-IFN/RBV to HCV Patients Being Non-Responsive to Prior Treatment with PEG-IFN/RBV The backbone of HCV treatment (Standard of Care; SoC) is PEGylated interferon-α-2a (PEG-IFN) and ribavirin (RBV) [M. Stefan et al., 2012. Short Guide to Hepatitis C, 12th Ed., Flying Publisher]. A clinical trial was performed in order to assess the add-on effect of hydroxychloroquine sulfate (HCQ) when combined with SoC on chronic HCV patients being non-responsive to a previous SoC treatment.

Patient Enrolment Criteria:

Chronic genotype 1b HCV infected patients being non-responsive to SoC (i.e., patients who failed to achieve a sustained virological response (SVR) after treatment with PEG-IFN/RBV) were enrolled.

Responsiveness to prior treatment was determined by documentation of prior response. Non-responsive patients were categorized into two groups: (i) patients having less than 2 $\log_{10}$ unit reduction in HCV RNA level (IU/mL), compared to baseline at week 12 of the previous PEG-IFN/RBV treatment, were considered as "null responders"; (ii) patients having at least 2 $\log_{10}$ unit reduction in HCV RNA level (IU/mL), compared to baseline at week 12 of the previous PEG-IFN/RBV treatment, but not achieving an undetectable HCV RNA level (<50 IU/mL) at the end of the previous PEG-IFN/RBV treatment (i.e., not achieving a Sustained Virological Response), were considered as "partial responders".

Exclusion criteria included hypersensitivity to any one of the three drugs (HCQ, PEG-IFN, RBV); anaemia, thrombocytopenia, elevated bilirubin levels (>2.5 mg/dL), elevated ALT and/or AST (>10× upper limit of normal), or elevated creatinine (>1.5 mg/dL) and INR greater than 1.5; concomitant liver disease other than hepatitis C; decompensated cirrhosis; hepatocellular carcinoma (e.g., as determined by suggestive imaging study or alpha-fetoprotein (AFP) levels of >50 ng/ml); human immunodeficiency virus co-infection; major uncontrolled psychiatric illness; active illicit drug or alcohol abuse; serious co-morbid conditions; immunosuppressive treatment including corticosteroids; untreated or uncontrolled thyroid disease; solid transplant organ (renal, heart, or lung); and pregnancy or unwillingness to practice double contraception or abstinence.

Liver Disease Severity Assessment:

Liver disease severity was determined on liver biopsy using FibroTest. Fibrosis was scored on a 5-point scale from 0 to 4, as follows: F0=no fibrosis; F1=portal fibrosis without septa; F2=portal fibrosis with few septa; F3=numerous septa without cirrhosis; F4=cirrhosis. Activity of inflammation was scored on a 4-point scale from A0 to A3, as follows: A0=no activity; A1=mild activity; A2=moderate activity; A3=severe activity.

HCV RNA Level Measurement:

Plasma HCV RNA level (IU/mL) was measured using standard quantitative RT-PCR as described hereinabove. HCV RNA measurements were taken on the day of treatment initiation (baseline), four weeks after treatment initiation and twelve weeks after treatment initiation.

Treatment Regimen:

HCQ was administered as an oral tablet containing 200 mg hydroxychloroquine sulfate (Plaquenil®; Sanofi-Aventis, USA Ltd.) twice per day (400 mg in total per day).

PEG-IFN (Pegasys®; Hoffmann-La Roche Ltd.) was injected subcutaneously once weekly at a dose of 180 µg (0.5 ml).

RBV (Copegus®; Hoffmann-La Roche Ltd.) was administered as an oral tablet containing 200 mg ribavirin at a daily dose of 1000-1200 mg based on body weight. If body weight was <75 kg, the total daily dose of RBV was 1,000 mg, administered as 400 mg (2 tablets of 200 mg, morning intake) and 600 mg (3 tablets of 200 mg, evening intake). If body weight was ≥75 kg, the total daily dose was 1,200 mg administered as twice 600 mg (3 tablets of 200 mg per intake, morning and evening).

Data Collection and Analysis:

HCV RNA level (IU/ml) was measured at treatment initiation (baseline), at week 4 after treatment initiation and at week 12 after treatment initiation.

Efficacy Assessment:

The efficacy of the treatment (HCQ combined with PEG-IFN/RBV on chronic HCV patients who failed to respond to previous PEG-IFN/RBV treatment was determined by the changes (log decline) in HCV RNA levels.

Results:

As shown in Table 7 below, three out of five non-responsive patients (HCV-infected patients who did not achieve a Sustained Virological Response (SVR) from previous standard-of-care treatment) that were treated with HCQ combined with PEG-IFN/RBV exhibited a greater than 2 $\log_{10}$ reduction in HCV RNA level from the baseline after 12 weeks of treatment (i.e., achieved an Early Virological Response; EVR), which is a positive predictor of a cure.

TABLE 7

Effect of HCQ combined with PEG-IFN and RBV on reducing the HCV level in chronic genotype 1 HCV patients being non-responsive to a previous PEG-IFN/RBV treatment

| Patient Age | Patient Gender | Patient Liver Disease Severity | Patient Response to Previous SoC[1] Treatment | HCV RNA Level | | |
|---|---|---|---|---|---|---|
| | | | | Baseline (IU/ml) | Week 12 (IU/ml) | Change in HCV RNA level at Week 12 ($\log_{10}$ reduction) |
| 29 | F | F1; A0 | Null[2] | 1,281,085 | 284,329 | 0.65 |
| 46 | M | F4; A3 | Partial[3] | 5,539,535 | 4,721 | <u>3.07</u>* |
| 60 | F | F2; A2 | Null[2] | 734,270 | 46 | <u>4.20</u>* |
| 34 | M | F4 | Null[2] | 654,724 | 790 | <u>2.92</u>* |
| 70 | M | F4 | Null[2] | 1,558,394 | 26,608 | 1.77 |

*$\log_{10}$ reduction of ≥2 compared to baseline.
[1]SoC = Standard-of-Care; PEG-IFN/RBV.
[2]Null response: having less than 2 $\log_{10}$ reduction in HCV RNA level (IU/mL) compared to baseline at week 12 of the previous PEG-IFN/RBV treatment. [Patients who are null responders to SoC PEG-IFN/RBV combination therapy have demonstrated sustained virological response (SVRs) ranging between 5% and 16% with an optimized PEG-IFN/RBV retreatment (M. Stefan et al., 2012. Short Guide to Hepatitis C. 12$^{th}$ Edition. Flying Publisher)].
[3]Partial response: having at least 2 $\log_{10}$ reduction in HCV RNA level (IU/mL) compared to baseline at week 12 of the previous PEG-IFN/RBV treatment, but not achieving an undetectable HCV RNA level (<50 IU/mL) at the end of treatment. (Patients who are partial-responders to SoC PEG-IFN/RBV combination therapy have demonstrated SVRs ranging between 7% and 15% with a standard PEG-IFN/RBV retreatment [M. Stefan et al., 2012. Short Guide to Hepatitis C. 12th Edition. Flying Publisher]).

These results indicate that HCQ is capable of potentiating the activity of anti-HCV agents in the treatment of HCV-infected patients which failed to respond to a standard of care treatment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating an HCV infection, the method comprising:
   (a) identifying an HCV-infected subject non-responsive to an anti-HCV therapy; and
   (b) administering to said HCV-infected subject a therapeutically effective amount of hydroxychloroquine or a pharmaceutically acceptable salt thereof, wherein said therapeutically effective amount of hydroxychloroquine or a pharmaceutically acceptable salt thereof is in a range of from about 500 to about 2000 mg per day, thereby treating the HCV infection.

2. The method of claim 1, wherein said anti-HCV therapy comprises a treatment with PEGylated interferon α-2a or PEGylated interferon α-2b, in combination with ribavirin.

3. The method of claim 1, wherein said HCV-infected subject is lacking a sustained virological response (SVR).

4. The method of claim 1, wherein said pharmaceutically acceptable salt is hydroxychloroquine sulfate.

5. The method of claim 1, wherein said therapeutically effective amount of hydroxychloroquine or a pharmaceutically acceptable salt thereof is in a range of from about 500 to about 1000 mg per day.

6. The method of claim 1, further comprising administering to said HCV-infected subject a therapeutically effective amount of at least one antiviral agent.

7. The method of claim 6, wherein said at least one antiviral agent is selected from the group consisting of ribavirin, a viral protease inhibitor, a viral polymerase inhibitor, an NS4A inhibitor and an NS5A inhibitor.

8. The method of claim 7, further comprising administering to said HCV-infected subject a therapeutically effective amount of an interferon.

9. The method of claim 8, wherein said interferon is PEGylated interferon α-2a.

10. The method of claim 1, wherein said HCV-infected subject is infected by genotype 1 HCV.

11. The method of claim 10, wherein said HCV-infected subject is infected by genotype 1b HCV.

12. A method of treating an HCV infection, the method comprising:
   (a) identifying an HCV-infected subject non-responsive to an anti-HCV therapy, wherein said anti-HCV therapy comprises a treatment with PEGylated interferon α-2a or PEGylated interferon α-2b, in combination with ribavirin; and
   (b) administering to said HCV-infected subject a therapeutically effective amount of hydroxychloroquine or a pharmaceutically acceptable salt thereof, wherein said therapeutically effective amount of hydroxychloroquine or a pharmaceutically acceptable salt thereof is in a range of from about 500 to about 2000 mg per day, thereby treating the HCV infection.

* * * * *